(12) United States Patent
Shelton, IV et al.

(10) Patent No.: US 8,632,535 B2
(45) Date of Patent: *Jan. 21, 2014

(54) INTERLOCK AND SURGICAL INSTRUMENT INCLUDING SAME

(75) Inventors: Frederick E. Shelton, IV, Hillsboro, OH (US); James R. Giordano, Milford, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 763 days.

This patent is subject to a terminal disclaimer.

(21) Appl. No.: 12/793,599

(22) Filed: Jun. 3, 2010

(65) Prior Publication Data
US 2010/0301095 A1 Dec. 2, 2010

Related U.S. Application Data

(63) Continuation of application No. 11/651,715, filed on Jan. 10, 2007.

(51) Int. Cl.
*A61B 17/068* (2006.01)

(52) U.S. Cl.
USPC .................................. 606/41; 606/1; 128/898

(58) Field of Classification Search
USPC .............. 606/1; 227/19, 176.1, 179.1; 361/23
See application file for complete search history.

(56) References Cited

U.S. PATENT DOCUMENTS

| | | | |
|---|---|---|---|
| 3,490,675 A | 1/1970 | Green et al. | |
| 3,643,851 A | 2/1972 | Green et al. | |
| 3,662,939 A | 5/1972 | Bryan | |
| 3,717,294 A | 2/1973 | Green | |
| 3,819,100 A | 6/1974 | Noiles et al. | |
| 4,331,277 A | 5/1982 | Green | |
| 4,353,371 A | 10/1982 | Cosman | |
| 4,383,634 A | 5/1983 | Green | |
| 4,396,139 A | 8/1983 | Hall et al. | |
| 4,402,445 A | 9/1983 | Green | |
| 4,415,112 A | 11/1983 | Green | |
| 4,429,695 A | 2/1984 | Green | |
| 4,475,679 A | 10/1984 | Fleury, Jr. | |
| 4,489,875 A | 12/1984 | Crawford et al. | |
| 4,500,024 A | 2/1985 | DiGiovanni et al. | |
| 4,505,273 A | 3/1985 | Braun et al. | |
| 4,505,414 A | 3/1985 | Filipi | |
| 4,506,671 A | 3/1985 | Green | |

(Continued)

FOREIGN PATENT DOCUMENTS

| | | |
|---|---|---|
| CA | 2458946 A1 | 3/2003 |
| CA | 2512960 A1 | 1/2006 |

(Continued)

OTHER PUBLICATIONS

European Search Report, Application No. 08250093.5, dated Nov. 4, 2009 (7 pages).

(Continued)

*Primary Examiner* — Aaron Roane

(57) ABSTRACT

A surgical instrument is disclosed. The instrument includes an end effector comprising a moveable cutting instrument to cut an object and a motor coupled to the end effector. The motor actuates the cutting instrument in response to a current therethrough, causing the cutting instrument to move between a proximal-most position and a distal-most position. The instrument includes an interlock coupled to the end effector and to the motor to prevent actuation of the cutting instrument based on the current through the motor.

6 Claims, 41 Drawing Sheets

(56) References Cited

U.S. PATENT DOCUMENTS

| | | |
|---|---|---|
| 4,522,327 A | 6/1985 | Korthoff et al. |
| 4,530,453 A | 7/1985 | Green |
| 4,566,620 A | 1/1986 | Green et al. |
| 4,573,622 A | 3/1986 | Green et al. |
| 4,580,712 A | 4/1986 | Green |
| 4,610,383 A | 9/1986 | Rothfuss et al. |
| 4,629,107 A | 12/1986 | Fedotov et al. |
| 4,641,076 A | 2/1987 | Linden |
| 4,655,222 A | 4/1987 | Florez et al. |
| 4,664,305 A | 5/1987 | Blake, III et al. |
| 4,671,445 A | 6/1987 | Barker et al. |
| 4,715,520 A | 12/1987 | Roehr, Jr. et al. |
| 4,728,020 A | 3/1988 | Green et al. |
| 4,752,024 A | 6/1988 | Green et al. |
| 4,754,909 A | 7/1988 | Barker et al. |
| 4,767,044 A | 8/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,869,414 A | 9/1989 | Green et al. |
| 4,869,415 A | 9/1989 | Fox |
| 4,941,623 A | 7/1990 | Pruitt |
| 4,944,443 A | 7/1990 | Oddsen et al. |
| 5,065,929 A | 11/1991 | Schulze et al. |
| 5,071,430 A | 12/1991 | de Salis et al. |
| 5,129,570 A | 7/1992 | Schulze et al. |
| 5,137,198 A | 8/1992 | Nobis et al. |
| 5,139,513 A | 8/1992 | Segato |
| 5,158,567 A | 10/1992 | Green |
| 5,211,649 A | 5/1993 | Kohler et al. |
| 5,221,036 A | 6/1993 | Takase |
| 5,222,975 A | 6/1993 | Crainich |
| 5,258,009 A | 11/1993 | Conners |
| 5,282,806 A | 2/1994 | Haber et al. |
| 5,282,829 A | 2/1994 | Hermes |
| 5,304,204 A | 4/1994 | Bregen |
| 5,342,395 A | 8/1994 | Jarrett et al. |
| 5,342,396 A | 8/1994 | Cook |
| 5,350,400 A | 9/1994 | Esposito et al. |
| 5,356,006 A | 10/1994 | Alpern et al. |
| 5,366,479 A | 11/1994 | McGarry et al. |
| 5,368,015 A | 11/1994 | Wilk |
| 5,383,880 A | 1/1995 | Hooven |
| 5,395,033 A | 3/1995 | Byrne et al. |
| 5,397,324 A | 3/1995 | Carroll et al. |
| 5,413,272 A | 5/1995 | Green et al. |
| 5,417,361 A | 5/1995 | Williamson, IV |
| 5,425,745 A | 6/1995 | Green et al. |
| 5,433,721 A | 7/1995 | Hooven et al. |
| 5,465,895 A | 11/1995 | Knodel et al. |
| 5,474,566 A | 12/1995 | Alesi et al. |
| 5,478,354 A | 12/1995 | Tovey et al. |
| 5,480,089 A | 1/1996 | Blewett |
| 5,484,095 A | 1/1996 | Green et al. |
| 5,484,451 A | 1/1996 | Akopov et al. |
| 5,485,947 A | 1/1996 | Olson et al. |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,503,320 A | 4/1996 | Webster et al. |
| 5,509,596 A | 4/1996 | Green et al. |
| 5,518,163 A | 5/1996 | Hooven |
| 5,518,164 A | 5/1996 | Hooven |
| 5,529,235 A | 6/1996 | Boiarski et al. |
| 5,535,934 A | 7/1996 | Boiarski et al. |
| 5,535,937 A | 7/1996 | Boiarski et al. |
| 5,543,119 A | 8/1996 | Sutter et al. |
| 5,553,765 A | 9/1996 | Knodel et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,564,615 A | 10/1996 | Bishop et al. |
| 5,571,116 A | 11/1996 | Bolanos et al. |
| 5,575,799 A | 11/1996 | Bolanos et al. |
| 5,577,654 A | 11/1996 | Bishop |
| 5,579,978 A | 12/1996 | Green et al. |
| 5,580,067 A | 12/1996 | Hamblin et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,601,224 A | 2/1997 | Bishop et al. |
| 5,605,273 A | 2/1997 | Hamblin et al. |
| 5,607,094 A | 3/1997 | Clark et al. |
| 5,609,285 A | 3/1997 | Grant et al. |
| 5,624,452 A | 4/1997 | Yates |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,780 A | 6/1997 | Green et al. |
| 5,639,008 A | 6/1997 | Gallagher et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,260 A | 9/1997 | Yoon |
| 5,667,517 A | 9/1997 | Hooven |
| 5,667,527 A | 9/1997 | Cook |
| 5,669,544 A | 9/1997 | Schulze et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,680,983 A | 10/1997 | Plyley et al. |
| 5,685,474 A | 11/1997 | Seeber |
| 5,688,270 A | 11/1997 | Yates et al. |
| 5,690,269 A | 11/1997 | Bolanos et al. |
| 5,692,668 A | 12/1997 | Schulze et al. |
| 5,693,042 A | 12/1997 | Boiarski et al. |
| 5,697,543 A | 12/1997 | Burdorff |
| 5,702,408 A | 12/1997 | Wales et al. |
| 5,704,087 A | 1/1998 | Strub |
| 5,704,534 A | 1/1998 | Huitema et al. |
| 5,706,998 A | 1/1998 | Plyley et al. |
| 5,709,334 A | 1/1998 | Sorrentino et al. |
| 5,709,680 A | 1/1998 | Yates et al. |
| 5,711,472 A | 1/1998 | Bryan |
| 5,713,505 A | 2/1998 | Huitema |
| 5,715,987 A | 2/1998 | Kelley et al. |
| 5,716,366 A | 2/1998 | Yates |
| 5,718,360 A | 2/1998 | Green et al. |
| 5,725,536 A | 3/1998 | Oberlin et al. |
| 5,725,554 A | 3/1998 | Simon et al. |
| 5,730,758 A | 3/1998 | Allgeyer |
| 5,732,871 A | 3/1998 | Clark et al. |
| 5,732,872 A | 3/1998 | Bolduc et al. |
| 5,743,456 A | 4/1998 | Jones et al. |
| 5,752,644 A | 5/1998 | Bolanos et al. |
| 5,758,814 A | 6/1998 | Gallagher et al. |
| 5,762,256 A | 6/1998 | Mastri et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,799,857 A | 9/1998 | Robertson et al. |

(56) References Cited

U.S. PATENT DOCUMENTS

| | | | |
|---|---|---|---|
| 5,807,393 | A | 9/1998 | Williamson, IV et al. |
| 5,817,093 | A | 10/1998 | Williamson, IV et al. |
| 5,820,009 | A | 10/1998 | Melling et al. |
| 5,826,776 | A | 10/1998 | Schulze et al. |
| 5,833,695 | A | 11/1998 | Yoon |
| 5,836,503 | A | 11/1998 | Ehrenfels et al. |
| 5,839,639 | A | 11/1998 | Sauer et al. |
| 5,855,311 | A | 1/1999 | Hamblin et al. |
| 5,865,361 | A | 2/1999 | Milliman et al. |
| 5,868,760 | A | 2/1999 | McGuckin, Jr. |
| 5,876,401 | A | 3/1999 | Schulze et al. |
| 5,893,506 | A | 4/1999 | Powell |
| 5,897,562 | A | 4/1999 | Bolanos et al. |
| 5,901,895 | A | 5/1999 | Heaton et al. |
| 5,908,427 | A | 6/1999 | McKean et al. |
| 5,911,353 | A | 6/1999 | Bolanos et al. |
| 5,915,616 | A | 6/1999 | Viola et al. |
| 5,918,791 | A | 7/1999 | Sorrentino et al. |
| 5,919,198 | A | 7/1999 | Graves, Jr. et al. |
| 5,941,442 | A | 8/1999 | Geiste et al. |
| 5,954,259 | A | 9/1999 | Viola et al. |
| 6,010,054 | A | 1/2000 | Johnson et al. |
| 6,024,741 | A | 2/2000 | Williamson, IV et al. |
| 6,032,849 | A | 3/2000 | Mastri et al. |
| 6,039,734 | A | 3/2000 | Goble |
| 6,045,560 | A | 4/2000 | McKean et al. |
| 6,083,242 | A | 7/2000 | Cook |
| 6,086,600 | A | 7/2000 | Kortenbach |
| 6,099,551 | A | 8/2000 | Gabbay |
| 6,102,271 | A | 8/2000 | Longo et al. |
| 6,119,913 | A | 9/2000 | Adams et al. |
| 6,126,058 | A | 10/2000 | Adams et al. |
| 6,171,330 | B1 | 1/2001 | Benchetrit |
| 6,181,105 | B1 | 1/2001 | Cutolo et al. |
| 6,202,914 | B1 | 3/2001 | Geiste et al. |
| 6,241,139 | B1 | 6/2001 | Milliman et al. |
| 6,250,532 | B1 | 6/2001 | Green et al. |
| 6,264,086 | B1 | 7/2001 | McGuckin, Jr. |
| 6,264,087 | B1 | 7/2001 | Whitman |
| 6,273,897 | B1 | 8/2001 | Dalessandro et al. |
| 6,302,311 | B1 | 10/2001 | Adams et al. |
| 6,315,184 | B1 | 11/2001 | Whitman |
| 6,330,965 | B1 | 12/2001 | Milliman et al. |
| 6,331,181 | B1 | 12/2001 | Tierney et al. |
| 6,346,077 | B1 | 2/2002 | Taylor et al. |
| 6,387,113 | B1 | 5/2002 | Hawkins et al. |
| RE37,814 | E | 8/2002 | Allgeyer |
| 6,436,107 | B1 | 8/2002 | Wang et al. |
| 6,443,973 | B1 | 9/2002 | Whitman |
| 6,488,197 | B1 | 12/2002 | Whitman |
| 6,491,201 | B1 | 12/2002 | Whitman |
| 6,491,701 | B2 | 12/2002 | Tierney et al. |
| 6,505,768 | B2 | 1/2003 | Whitman |
| 6,517,565 | B1 | 2/2003 | Whitman et al. |
| 6,578,751 | B2 | 6/2003 | Hartwick |
| 6,588,643 | B2 | 7/2003 | Bolduc et al. |
| 6,596,432 | B2 | 7/2003 | Kawakami et al. |
| 6,601,749 | B2 | 8/2003 | Sullivan et al. |
| 6,616,686 | B2 | 9/2003 | Coleman et al. |
| 6,619,529 | B2 | 9/2003 | Green et al. |
| 6,629,988 | B2 | 10/2003 | Weadock |
| 6,644,532 | B2 | 11/2003 | Green et al. |
| 6,648,816 | B2 | 11/2003 | Irion et al. |
| 6,666,875 | B1 | 12/2003 | Sakurai et al. |
| 6,679,410 | B2 | 1/2004 | Würsch et al. |
| 6,681,978 | B2 | 1/2004 | Geiste et al. |
| 6,681,979 | B2 | 1/2004 | Whitman |
| 6,695,199 | B2 | 2/2004 | Whitman |
| 6,698,643 | B2 | 3/2004 | Whitman |
| 6,716,233 | B1 | 4/2004 | Whitman |
| 6,755,338 | B2 | 6/2004 | Hahnen et al. |
| 6,769,594 | B2 | 8/2004 | Orban, III |
| 6,773,438 | B1 | 8/2004 | Knodel et al. |
| 6,783,524 | B2 | 8/2004 | Anderson et al. |
| 6,793,652 | B1 | 9/2004 | Whitman et al. |
| 6,805,273 | B2 | 10/2004 | Bilotti et al. |
| 6,817,508 | B1 | 11/2004 | Racenet et al. |
| 6,817,509 | B2 | 11/2004 | Geiste et al. |
| 6,830,174 | B2 | 12/2004 | Hillstead et al. |
| 6,843,403 | B2 | 1/2005 | Whitman |
| 6,846,307 | B2 | 1/2005 | Whitman et al. |
| 6,846,308 | B2 | 1/2005 | Whitman et al. |
| 6,846,309 | B2 | 1/2005 | Whitman et al. |
| 6,849,071 | B2 | 2/2005 | Whitman et al. |
| RE38,708 | E | 3/2005 | Bolanos et al. |
| 6,866,671 | B2 | 3/2005 | Tierney et al. |
| 6,874,669 | B2 | 4/2005 | Adams et al. |
| 6,877,647 | B2 | 4/2005 | Green et al. |
| 6,889,116 | B2 | 5/2005 | Jinno |
| 6,905,057 | B2 | 6/2005 | Swayze et al. |
| 6,945,444 | B2 | 9/2005 | Gresham et al. |
| 6,953,138 | B1 | 10/2005 | Dworak et al. |
| 6,953,139 | B2 | 10/2005 | Milliman et al. |
| 6,959,852 | B2 | 11/2005 | Shelton, IV et al. |
| 6,964,363 | B2 | 11/2005 | Wales et al. |
| 6,972,199 | B2 | 12/2005 | Lebouitz et al. |
| 6,978,921 | B2 | 12/2005 | Shelton, IV et al. |
| 6,978,922 | B2 | 12/2005 | Bilotti et al. |
| 6,981,628 | B2 | 1/2006 | Wales |
| 6,981,941 | B2 | 1/2006 | Whitman et al. |
| 6,986,451 | B1 | 1/2006 | Mastri et al. |
| 6,988,649 | B2 | 1/2006 | Shelton, IV et al. |
| 6,988,650 | B2 | 1/2006 | Schwemberger et al. |
| 7,000,818 | B2 | 2/2006 | Shelton, IV et al. |
| 7,000,819 | B2 | 2/2006 | Swayze et al. |
| 7,008,435 | B2 | 3/2006 | Cummins |
| 7,025,743 | B2 | 4/2006 | Mann et al. |
| 7,032,798 | B2 | 4/2006 | Whitman et al. |
| 7,032,799 | B2 | 4/2006 | Viola et al. |
| 7,044,352 | B2 | 5/2006 | Shelton, IV et al. |
| 7,044,353 | B2 | 5/2006 | Mastri et al. |
| 7,055,731 | B2 | 6/2006 | Shelton, IV et al. |
| 7,056,330 | B2 | 6/2006 | Gayton |
| 7,070,083 | B2 | 7/2006 | Jankowski |
| 7,077,856 | B2 | 7/2006 | Whitman |
| 7,080,769 | B2 | 7/2006 | Vresh et al. |
| 7,083,075 | B2 | 8/2006 | Swayze et al. |
| 7,083,571 | B2 | 8/2006 | Wang et al. |
| 7,083,615 | B2 | 8/2006 | Peterson et al. |
| 7,090,684 | B2 | 8/2006 | McGuckin, Jr. et al. |
| 7,108,695 | B2 | 9/2006 | Witt et al. |
| 7,108,709 | B2 | 9/2006 | Cummins |
| 7,111,769 | B2 | 9/2006 | Wales et al. |
| 7,114,642 | B2 | 10/2006 | Whitman |
| 7,118,582 | B1 | 10/2006 | Wang et al. |
| 7,121,446 | B2 | 10/2006 | Arad et al. |
| 7,128,253 | B2 | 10/2006 | Mastri et al. |
| 7,128,254 | B2 | 10/2006 | Shelton, IV et al. |
| 7,140,527 | B2 | 11/2006 | Ehrenfels et al. |
| 7,147,138 | B2 | 12/2006 | Shelton, IV |
| 7,156,863 | B2 | 1/2007 | Sonnenschein et al. |
| 7,159,750 | B2 | 1/2007 | Racenet et al. |
| 7,168,604 | B2 | 1/2007 | Milliman et al. |
| 7,188,758 | B2 | 3/2007 | Viola et al. |
| 7,207,471 | B2 | 4/2007 | Heinrich et al. |
| 7,207,472 | B2 | 4/2007 | Wukusick et al. |
| 7,210,609 | B2 | 5/2007 | Leiboff et al. |
| 7,213,736 | B2 | 5/2007 | Wales et al. |
| 7,220,272 | B2 | 5/2007 | Weadock |
| 7,225,964 | B2 | 6/2007 | Mastri et al. |
| 7,238,195 | B2 | 7/2007 | Viola |
| 7,246,734 | B2 | 7/2007 | Shelton, IV |
| 7,256,695 | B2 | 8/2007 | Hamel et al. |
| 7,258,262 | B2 | 8/2007 | Mastri et al. |
| 7,260,431 | B2 | 8/2007 | Libbus et al. |
| 7,273,483 | B2 | 9/2007 | Wiener et al. |
| 7,278,562 | B2 | 10/2007 | Mastri et al. |
| 7,278,563 | B1 | 10/2007 | Green |
| 7,296,724 | B2 | 11/2007 | Green et al. |
| 7,303,106 | B2 | 12/2007 | Milliman et al. |
| 7,303,107 | B2 | 12/2007 | Milliman et al. |
| 7,303,108 | B2 | 12/2007 | Shelton, IV |
| 7,303,556 | B2 | 12/2007 | Metzger |
| 7,328,828 | B2 | 2/2008 | Ortiz et al. |

(56) References Cited

U.S. PATENT DOCUMENTS

| | | |
|---|---|---|
| 7,328,829 B2 | 2/2008 | Arad et al. |
| 7,354,447 B2 | 4/2008 | Shelton, IV et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,397,364 B2 | 7/2008 | Govari |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,730 B2 | 10/2008 | Viola |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,481,347 B2 | 1/2009 | Roy |
| 7,490,749 B2 | 2/2009 | Schall et al. |
| 7,494,039 B2 | 2/2009 | Racenet et al. |
| 7,500,979 B2 | 3/2009 | Hueil et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,546,940 B2 | 6/2009 | Milliman et al. |
| 7,549,563 B2 | 6/2009 | Mather et al. |
| 7,549,564 B2 | 6/2009 | Boudreaux |
| 7,568,603 B2 | 8/2009 | Shelton, IV et al. |
| 7,568,619 B2 | 8/2009 | Todd et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,631,793 B2 | 12/2009 | Rethy et al. |
| 7,644,848 B2 | 1/2010 | Swayze et al. |
| 7,658,311 B2 | 2/2010 | Boudreaux |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,717,312 B2 | 5/2010 | Beetel |
| 7,721,931 B2 | 5/2010 | Shelton, IV et al. |
| 7,721,934 B2 | 5/2010 | Shelton, IV et al. |
| 7,721,936 B2 | 5/2010 | Shalton, IV et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,766,210 B2 | 8/2010 | Shelton, IV et al. |
| 7,770,775 B2 | 8/2010 | Shelton, IV et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,954,682 B2 | 6/2011 | Giordano et al. |
| 8,241,271 B2 | 8/2012 | Millman et al. |
| 8,479,969 B2 | 7/2013 | Shelton, IV |
| 2002/0117534 A1 | 8/2002 | Green et al. |
| 2003/0093103 A1 | 5/2003 | Malackowski et al. |
| 2003/0105478 A1 | 6/2003 | Whitman et al. |
| 2003/0130677 A1 | 7/2003 | Whitman et al. |
| 2004/0006372 A1 | 1/2004 | Racenet et al. |
| 2004/0034369 A1 | 2/2004 | Sauer et al. |
| 2004/0094597 A1 | 5/2004 | Whitman et al. |
| 2004/0108357 A1 | 6/2004 | Milliman et al. |
| 2004/0116952 A1 | 6/2004 | Sakurai et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2004/0243151 A1 | 12/2004 | Demmy et al. |
| 2004/0254608 A1 | 12/2004 | Huitema et al. |
| 2005/0032511 A1 | 2/2005 | Malone et al. |
| 2005/0059997 A1 | 3/2005 | Bauman et al. |
| 2005/0103819 A1 | 5/2005 | Racenet et al. |
| 2005/0119669 A1 | 6/2005 | Demmy |
| 2005/0125009 A1 | 6/2005 | Perry et al. |
| 2005/0131390 A1 | 6/2005 | Heinrich et al. |
| 2005/0143759 A1 | 6/2005 | Kelly |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0240222 A1 | 10/2005 | Shipp |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0025812 A1 | 2/2006 | Shelton, IV |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0085033 A1 | 4/2006 | Criscuolo et al. |
| 2006/0100643 A1 | 5/2006 | Laufer et al. |
| 2006/0108393 A1 | 5/2006 | Heinrich et al. |
| 2006/0180634 A1 | 8/2006 | Shelton, IV et al. |
| 2006/0212069 A1 | 9/2006 | Shelton, IV |
| 2006/0226196 A1 | 10/2006 | Hueil et al. |
| 2006/0235469 A1 | 10/2006 | Viola |
| 2006/0241692 A1 | 10/2006 | McGuckin, Jr. et al. |
| 2006/0278680 A1 | 12/2006 | Viola et al. |
| 2006/0278681 A1 | 12/2006 | Viola et al. |
| 2006/0284730 A1 | 12/2006 | Schmid et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0034668 A1 | 2/2007 | Holsten et al. |
| 2007/0073341 A1 | 3/2007 | Smith et al. |
| 2007/0084897 A1 | 4/2007 | Shelton, IV et al. |
| 2007/0102472 A1 | 5/2007 | Shelton, IV |
| 2007/0106317 A1 | 5/2007 | Shelton, IV et al. |
| 2007/0114261 A1 | 5/2007 | Ortiz et al. |
| 2007/0170225 A1 | 7/2007 | Shelton, IV et al. |
| 2007/0173806 A1 | 7/2007 | Orszulak et al. |
| 2007/0173813 A1 | 7/2007 | Odom |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175964 A1 | 8/2007 | Shelton, IV et al. |
| 2007/0181632 A1 | 8/2007 | Milliman |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0246505 A1 | 10/2007 | Pace-Floridia et al. |
| 2007/0295780 A1 | 12/2007 | Shelton et al. |
| 2007/0299427 A1 | 12/2007 | Yeung et al. |
| 2008/0029570 A1 | 2/2008 | Shelton et al. |

(56) References Cited

U.S. PATENT DOCUMENTS

| | | |
|---|---|---|
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0035701 A1 | 2/2008 | Racenet et al. |
| 2008/0041917 A1 | 2/2008 | Racenet et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0140115 A1 | 6/2008 | Stopek |
| 2008/0167522 A1 | 7/2008 | Giordano et al. |
| 2008/0167644 A1 | 7/2008 | Shelton et al. |
| 2008/0167671 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0197167 A1 | 8/2008 | Viola et al. |
| 2008/0200835 A1 | 8/2008 | Monson et al. |
| 2008/0210738 A1 | 9/2008 | Shelton et al. |
| 2008/0237296 A1 | 10/2008 | Boudreaux et al. |
| 2008/0251568 A1 | 10/2008 | Zemlok et al. |
| 2008/0283570 A1 | 11/2008 | Boyden et al. |
| 2008/0290134 A1 | 11/2008 | Bettuchi et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314957 A1 | 12/2008 | Boudreaux |
| 2009/0001121 A1 | 1/2009 | Hess et al. |
| 2009/0001122 A1 | 1/2009 | Prommersberger et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012534 A1 | 1/2009 | Madhani et al. |
| 2009/0012556 A1 | 1/2009 | Boudreaux et al. |
| 2009/0054908 A1 | 2/2009 | Zand et al. |
| 2009/0076534 A1 | 3/2009 | Shelton, IV et al. |
| 2009/0157067 A1 | 6/2009 | Kane et al. |
| 2009/0206123 A1 | 8/2009 | Doll et al. |
| 2009/0206124 A1 | 8/2009 | Hall et al. |
| 2009/0206125 A1 | 8/2009 | Huitema et al. |
| 2009/0206126 A1 | 8/2009 | Huitema et al. |
| 2009/0206128 A1 | 8/2009 | Hueil et al. |
| 2009/0206129 A1 | 8/2009 | Doll et al. |
| 2009/0206130 A1 | 8/2009 | Hall et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206134 A1 | 8/2009 | Swayze et al. |
| 2009/0206135 A1 | 8/2009 | Hall et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255978 A1 | 10/2009 | Viola et al. |
| 2009/0289096 A1 | 11/2009 | Shelton, IV et al. |
| 2009/0292283 A1 | 11/2009 | Odom |
| 2010/0032470 A1 | 2/2010 | Hess et al. |
| 2010/0065605 A1 | 3/2010 | Shelton, IV et al. |
| 2010/0065609 A1 | 3/2010 | Schwemberger |
| 2010/0069942 A1 | 3/2010 | Shelton, IV |
| 2010/0072251 A1 | 3/2010 | Baxter, III et al. |
| 2010/0072252 A1 | 3/2010 | Baxter, III et al. |
| 2010/0072253 A1 | 3/2010 | Baxter, III et al. |
| 2010/0072256 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089974 A1 | 4/2010 | Shelton, IV |
| 2010/0096435 A1 | 4/2010 | Fuchs et al. |
| 2010/0133317 A1 | 6/2010 | Shelton, IV et al. |
| 2010/0133318 A1 | 6/2010 | Boudreaux |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0237132 A1 | 9/2010 | Measamer et al. |
| 2010/0243709 A1 | 9/2010 | Hess et al. |
| 2010/0294829 A1 | 11/2010 | Giordano et al. |
| 2011/0132963 A1 | 6/2011 | Giordano et al. |
| 2011/0174861 A1 | 7/2011 | Shelton, IV et al. |
| 2011/0290855 A1 | 12/2011 | Moore et al. |
| 2011/0295270 A1 | 12/2011 | Giordano et al. |
| 2012/0283707 A1 | 11/2012 | Giordano et al. |
| 2013/0075443 A1 | 3/2013 | Giordano et al. |
| 2013/0190733 A1 | 7/2013 | Giordano et al. |

FOREIGN PATENT DOCUMENTS

| | | |
|---|---|---|
| CA | 2514274 A1 | 1/2006 |
| DE | 273689 C | 5/1914 |
| DE | 1775926 A | 1/1972 |
| DE | 9412228 U | 9/1994 |
| DE | 19924311 A1 | 11/2000 |
| DE | 69328576 T2 | 1/2001 |
| DE | 20112837 U1 | 10/2001 |
| DE | 20121753 U1 | 4/2003 |
| DE | 10314072 A1 | 10/2004 |
| EP | 0122046 A1 | 10/1984 |
| EP | 0070230 B1 | 10/1985 |
| EP | 0033548 B1 | 5/1986 |
| EP | 0276104 A2 | 7/1988 |
| EP | 0639349 A2 | 2/1994 |
| EP | 0324636 B1 | 3/1994 |
| EP | 0593920 A1 | 4/1994 |
| EP | 0600182 A2 | 6/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0679367 A2 | 11/1995 |
| EP | 0392547 B1 | 12/1995 |
| EP | 0685204 A1 | 12/1995 |
| EP | 0699418 A1 | 3/1996 |
| EP | 0702937 A1 | 3/1996 |
| EP | 0705571 A1 | 4/1996 |
| EP | 0484677 B2 | 6/1996 |
| EP | 0541987 B1 | 7/1996 |
| EP | 0667119 B1 | 7/1996 |

(56) References Cited

FOREIGN PATENT DOCUMENTS

| | | |
|---|---|---|
| EP | 0770355 A1 | 5/1997 |
| EP | 0503662 B1 | 6/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0676173 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0760230 B1 | 2/1999 |
| EP | 0537572 B1 | 6/1999 |
| EP | 0552050 B1 | 5/2000 |
| EP | 1090592 A1 | 4/2001 |
| EP | 1256318 B1 | 5/2001 |
| EP | 0908152 B1 | 1/2002 |
| EP | 0872213 B1 | 5/2002 |
| EP | 1238634 A2 | 9/2002 |
| EP | 0656188 B1 | 1/2003 |
| EP | 0829235 B1 | 6/2003 |
| EP | 0813843 B1 | 10/2003 |
| EP | 0741996 B1 | 2/2004 |
| EP | 0705570 B1 | 4/2004 |
| EP | 1086713 B1 | 5/2004 |
| EP | 1426012 A1 | 6/2004 |
| EP | 0888749 B1 | 9/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 1520521 A1 | 4/2005 |
| EP | 1520523 A1 | 4/2005 |
| EP | 1520525 A1 | 4/2005 |
| EP | 1522264 A1 | 4/2005 |
| EP | 1550408 A1 | 7/2005 |
| EP | 1557129 A1 | 7/2005 |
| EP | 1064883 B1 | 8/2005 |
| EP | 1157666 B1 | 9/2005 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1652481 A2 | 5/2006 |
| EP | 1382303 B1 | 6/2006 |
| EP | 1045672 B1 | 8/2006 |
| EP | 1617768 B1 | 8/2006 |
| EP | 1702567 A2 | 9/2006 |
| EP | 1129665 B1 | 11/2006 |
| EP | 1256317 B1 | 12/2006 |
| EP | 1728473 A1 | 12/2006 |
| EP | 1728475 A2 | 12/2006 |
| EP | 1479346 B1 | 1/2007 |
| EP | 1484024 B1 | 1/2007 |
| EP | 1754445 A2 | 2/2007 |
| EP | 1759812 A1 | 3/2007 |
| EP | 1769756 A1 | 4/2007 |
| EP | 1769758 A1 | 4/2007 |
| EP | 1785097 A2 | 5/2007 |
| EP | 1790293 A2 | 5/2007 |
| EP | 1800610 A1 | 6/2007 |
| EP | 1300117 B1 | 8/2007 |
| EP | 1813199 A1 | 8/2007 |
| EP | 1813201 A1 | 8/2007 |
| EP | 1813203 A2 | 8/2007 |
| EP | 1813207 A1 | 8/2007 |
| EP | 1813209 A1 | 8/2007 |
| EP | 1839596 A1 | 10/2007 |
| EP | 1402821 B1 | 12/2007 |
| EP | 1872727 A1 | 1/2008 |
| EP | 1897502 A1 | 3/2008 |
| EP | 1702568 B1 | 7/2008 |
| EP | 1970014 A1 | 9/2008 |
| EP | 1980213 A2 | 10/2008 |
| EP | 1759645 B1 | 11/2008 |
| EP | 1552795 B1 | 12/2008 |
| EP | 1693008 B1 | 12/2008 |
| EP | 2000102 A2 | 12/2008 |
| EP | 1749486 B1 | 3/2009 |
| EP | 2090256 A2 | 8/2009 |
| EP | 1813206 B1 | 4/2010 |
| FR | 999646 A | 2/1952 |
| FR | 1112936 A | 3/1956 |
| FR | 2765794 A | 1/1999 |
| GB | 939929 A | 10/1963 |
| GB | 1210522 A | 10/1970 |
| GB | 2336214 A | 10/1999 |
| JP | 6007357 A | 1/1994 |
| JP | 7051273 A | 2/1995 |
| JP | 8033641 A | 2/1996 |
| JP | 8229050 A | 9/1996 |
| JP | 2000287987 A | 10/2000 |
| JP | 2001286477 A | 10/2001 |
| JP | 2002369820 A | 12/2002 |
| JP | 2004-532084 A | 10/2004 |
| JP | 2005-28148 A | 2/2005 |
| JP | 2005505322 T | 2/2005 |
| JP | 2005103293 A | 4/2005 |
| JP | 2005-144183 A | 6/2005 |
| JP | 2005-523105 A | 8/2005 |
| JP | 2009-506799 A | 2/2009 |
| RU | 2187249 C2 | 8/2002 |
| RU | 2225170 C2 | 3/2004 |
| SU | 1377053 A1 | 2/1988 |
| SU | 1561964 A1 | 5/1990 |
| SU | 1722476 A1 | 3/1992 |
| WO | WO 93/08755 A1 | 5/1993 |
| WO | WO 93/15648 A1 | 8/1993 |
| WO | WO 95/18572 A1 | 7/1995 |
| WO | WO 95/23557 A1 | 9/1995 |
| WO | WO 95/29639 A1 | 11/1995 |
| WO | WO 96/22055 A1 | 7/1996 |
| WO | WO 96/35464 A1 | 11/1996 |
| WO | WO 97/34533 A1 | 9/1997 |
| WO | WO 97/39688 A2 | 10/1997 |
| WO | WO 98/17180 A1 | 4/1998 |
| WO | WO 98/30153 A1 | 7/1998 |
| WO | WO 99/12483 A1 | 3/1999 |
| WO | WO 99/15086 A1 | 4/1999 |
| WO | WO 99/34744 A1 | 7/1999 |
| WO | WO 99/45849 A1 | 9/1999 |
| WO | WO 00/24322 A1 | 5/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/05702 A1 | 1/2001 |
| WO | WO 01/10482 A1 | 2/2001 |
| WO | WO 01/54594 A1 | 8/2001 |
| WO | WO 01/62158 A2 | 8/2001 |
| WO | WO 01/62162 A1 | 8/2001 |
| WO | WO 01/62164 A2 | 8/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/30297 A2 | 4/2002 |
| WO | WO 02/32322 A2 | 4/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/020106 A2 | 3/2003 |
| WO | WO 03/020139 A2 | 3/2003 |
| WO | WO 03/079909 A3 | 3/2003 |
| WO | WO 03/030743 A2 | 4/2003 |
| WO | WO 03/037193 A1 | 5/2003 |

(56) References Cited

FOREIGN PATENT DOCUMENTS

| | | |
|---|---|---|
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/019803 A1 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/078892 A1 | 8/2005 |
| WO | WO 2005/096954 A2 | 10/2005 |
| WO | WO 2005/112808 A1 | 12/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/115958 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/039270 A1 | 4/2008 |
| WO | WO 2008/045383 A2 | 4/2008 |

OTHER PUBLICATIONS

European Examination Report, Application No. 08250093.5, dated Jun. 14, 2010 (5 pages).

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

Partial European Search Report, Application No. 08250085.1, dated Apr. 15, 2008 (7 pages).

European Search Report for Application No. 12173438.8, dated Oct. 24, 2012 (8 pages).

European Examination Report for Application No. 08250093.5, dated Jan. 19, 2012 (4 pages).

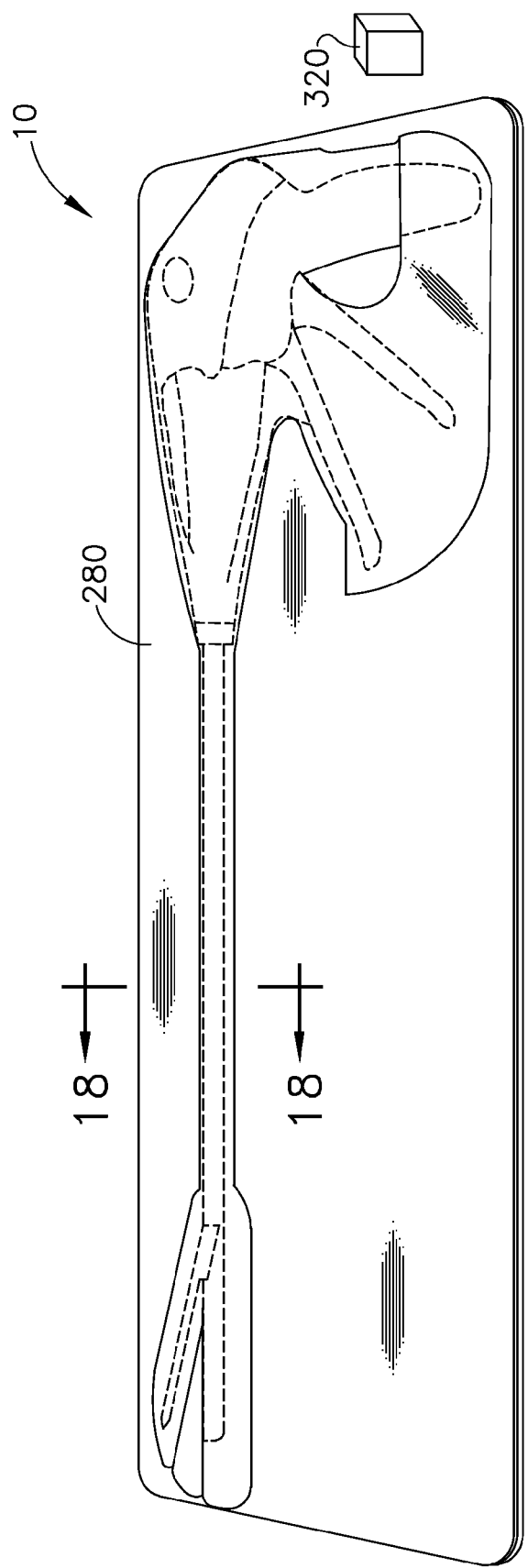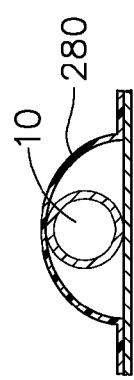
FIG. 17
FIG. 18

INTERLOCK AND SURGICAL INSTRUMENT INCLUDING SAME

CROSS REFERENCE TO RELATED APPLICATIONS

The present application is a continuation of U.S. patent application Ser. No. 11/651,715, filed, Jan. 10, 2007, now U.S. Patent Publication No. 2008/0167522, and is related to the following U.S. patent applications, which are incorporated herein by reference:

(1) U.S. patent application Ser. No. 11/651,807 entitled "SURGICAL INSTRUMENT WITH WIRELESS COMMUNICATION BETWEEN CONTROL UNIT AND REMOTE SENSOR," by J. Giordano et al., now U.S. Pat. No. 8,459,520;

(2) U.S. patent application Ser. No. 11/651,806 entitled "SURGICAL INSTRUMENT WITH ELEMENTS TO COMMUNICATE BETWEEN CONTROL UNIT AND END EFFECTOR," by J. Giordano et al., now U.S. Patent No. 7,954,682;

(3) U.S. patent application Ser. No. 11/651,768 entitled "PREVENTION OF CARTRIDGE REUSE IN A SURGICAL INSTRUMENT," by F. Shelton et al., now U.S. Pat. No. 7,721,931;

(4) U.S. patent application Ser. No. 11/651,771 entitled "POST-STERILIZATION PROGRAMMING OF SURGICAL INSTRUMENTS," by J. Swayze et al., now U.S. Pat. No. 7,738,971;

(5) U.S. patent application Ser. No. 11/651,788 entitled "INTERLOCK AND SURGICAL INSTRUMENT INCLUDING SAME, by F. Shelton et al., now U.S. Pat. No. 7,721,936; and (6) U.S. patent application Ser. No. 11/651,785 entitled "SURGICAL INSTRUMENT WITH ENHANCED BATTERY PERFORMANCE," by F. Shelton et al., now U.S. Pat. No. 7,900,805.

BACKGROUND

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

Advantageously, the design of the end effector may be such that it can be reused with the surgical stapler. For instance, one patient may need a series of severing and stapling operations. Replacing an entire end effector for each operation tends to be economically inefficient, especially if the end effector is built for strength and reliability over repeated operations. To that end, the staple cartridge is typically configured to be disposable and is fitted into the end effector prior to each operation of the surgical stapler.

An example of a surgical stapler suitable for endoscopic applications is described in U.S. Pat. No. 5,465,895, which discloses an endocutter with distinct closing and firing actions. A clinician using this device is able to close the jaw members upon tissue to position the tissue prior to firing. Once the clinician has determined that the jaw members are properly gripping tissue, the clinician can then fire the surgical stapler with a single firing stroke, thereby severing and stapling the tissue. The simultaneous severing and stapling avoids complications that may arise when performing such actions sequentially with different surgical tools that respectively only sever and staple.

One specific advantage of being able to close upon tissue before firing is that the clinician is able to verify via an endoscope that the desired location for the cut has been achieved, including that a sufficient amount of tissue has been captured between opposing jaws. Otherwise, opposing jaws may be drawn too close together, especially pinching at their distal ends, and thus not effectively forming closed staples in the severed tissue. At the other extreme, an excessive amount of clamped tissue may cause binding and an incomplete firing.

Endoscopic staplers/cutters continue to increase in complexity and function with each generation. One of the main reasons for this is the quest to lower force-to-fire (FTF) to a level that all or a great majority of surgeons can handle. One known solution to lower FTF it use $CO_2$ or electrical motors. These devices have not faired much better than traditional hand-powered devices, but for a different reason. Surgeons typically prefer to experience proportionate force distribution to that being experienced by the end effector in the forming of the staple to assure them that the cutting/stapling cycle is complete, with the upper limit within the capabilities of most surgeons (usually around 15-30 lbs). They also typically want to maintain control of deploying the staples and being able to stop at anytime if the forces felt in the handle of the device feel too great or for some other clinical reason.

To address this need, so-called "power-assist" endoscopic surgical instruments have been developed in which a supplemental power source aids in the firing of the instrument. For example, in some power-assist devices, a motor provides supplemental electrical power to the power input by the user from squeezing the firing trigger. Such devices are capable of providing loading force feedback and control to the operator to reduce the firing force required to be exerted by the operator in order to complete the cutting operation. One such power-assist device is described in U.S. patent application Ser. No. 11/343,573, filed Jan. 31, 2006 by Shelton et al., entitled "Motor-driven surgical cutting and fastening instrument with loading force feedback," ("the '573 application") which is incorporated herein by reference.

These power-assist devices often include other components that purely mechanical endoscopic surgical instruments do not, such as sensors and control systems. One challenge in using such electronics in a surgical instrument is delivering power and/or data to and from the sensors, particularly when there is a free rotating joint in the surgical instrument.

Although powered instruments provide numerous advantages, it is desirable to prevent inadvertent firing of the instrument under certain conditions. For example, firing the instrument without having a staple cartridge installed, or firing the instrument having an installed but spent (e.g., previously fired) staple cartridge, may result in cutting of tissue without simultaneous stapling to minimize bleeding. Interlocks for preventing powered endocutter operation under such conditions have heretofore utilized electronic sensors in the end effector for determining whether an unspent staple cartridge has been installed. U.S. patent application Ser. No. 11/343,439 entitled "ELECTRONIC INTERLOCKS AND SURGICAL INSTRUMENT INCLUDING SAME" to Swayze et al., the disclosure of which is incorporated herein by reference, discloses the use of electronic sensors disposed within the end effector for determining if an unspent staple cartridge has been installed. The sensors may include switches connected in series with a motor or other electrically-powered actuation mechanism such that current flow necessary for generating the actuating force is prevented when the staple cartridge is not installed, or when the staple cartridge is installed but spent. Although such electronic interlocks are effective, placement of sensors in the end effector and routing electrical cabling between the sensors and motor electronics (typically housed in the instrument handle) increases instrument complexity and cost.

Although the use of mechanical interlocks in end effectors for preventing inadvertent firing is known and avoids complexities associated with end effector electronics, such mechanisms have heretofore been limited to manually powered endocutters. In particular, such mechanisms may not have the mechanical strength to resist the firing force generated by electrically-powered actuation mechanisms. Additionally, even if a mechanical interlock is capable of withstanding the firing force, the resulting physical stresses may be transmitted to other instrument components and cause unacceptable wear or damage.

Consequently, a significant need exists for an interlock for use in powered cutting and stapling instruments that prevents inadvertent firing (e.g., cutting but not stapling) while avoiding complexities of sensor-equipped end effectors and deleterious physical stresses that may otherwise result from the use of conventional mechanical interlocks.

SUMMARY

In one general aspect, the present application is directed to a surgical instrument, such as an endoscopic or laparoscopic instrument. According to one embodiment, the surgical instrument comprises an end effector comprising at least one sensor transponder that is passively powered. The surgical instrument also comprises a shaft having a distal end connected to the end effector and a handle connected to a proximate end of the shaft. The handle comprises a control unit (e.g., a microcontroller) that is in communication with the sensor transponder via at least one inductive coupling. Further, the surgical instrument may comprise a rotational joint for rotating the shaft. In such a case, the surgical instrument may comprise a first inductive element located in the shaft distally from the rotational joint and inductively coupled to the control unit, and a second inductive element located distally in the shaft and inductively coupled to the at least one sensor transponder. The first and second inductive elements may be connected by a wired, physical connection.

That way, the control unit may communicate with the transponder in the end effector without a direct wired connection through complex mechanical joints like the rotating joint where it may be difficult to maintain such a wired connection. In addition, because the distances between the inductive elements may be fixed and known, the couplings could be optimized for inductive transfer of energy. Also, the distances could be relatively short so that relatively low power signals could be used to thereby minimize interference with other systems in the use environment of the instrument.

In another general aspect of the present application, the electrically conductive shaft of the surgical instrument may serve as an antenna for the control unit to wirelessly communicate signals to and from the sensor transponder. For example, the sensor transponder could be located on or disposed in a nonconductive component of the end effector, such as a plastic cartridge, thereby insulating the sensor from conductive components of the end effector and the shaft. In addition, the control unit in the handle may be electrically coupled to the shaft. In that way, the shaft and/or the end effector may serve as an antenna for the control unit by radiating signals from the control unit to the sensor and/or by receiving radiated signals from the sensor. Such a design is particularly useful in surgical instruments having complex mechanical joints (such as rotary joints), which make it difficult to use a direct wired connection between the sensor and control unit for communicating data signals.

In another embodiment, the shaft and/or components of the end effector could serve as the antenna for the sensor by radiating signals to the control unit and receiving radiated signals from the control unit. According to such an embodiment, the control unit is electrically insulated from the shaft and the end effector.

In another general aspect, the present application is directed to a surgical instrument comprising a programmable control unit that can be programmed by a programming device after the instrument has been packaged and sterilized. In one such embodiment, the programming device may wirelessly program the control unit. The control unit may be passively powered by the wireless signals from the programming device during the programming operation. In another embodiment, the sterile container may comprise a connection interface so that the programming unit can be connected to the surgical instrument while the surgical instrument is in its sterilized container.

This application discloses a surgical cutting and stapling instrument according to various embodiments. The instrument includes an end effector comprising a moveable cutting instrument to cut an object and a motor to actuate the cutting instrument in response to a current therethrough. The actuation of the cutting instrument causes the cutting instrument to move between a proximal-most position and a distal-most position. The instrument further includes an interlock coupled to the end effector and to the motor to prevent actuation of the cutting instrument based on the current through the motor.

This application further discloses a method for preventing operation of a surgical instrument. The surgical instrument is configured for removably receiving an expendable staple cartridge and comprises a moveable cutting instrument and a motor to actuate the cutting instrument in response to a current therethrough. The method comprises mechanically blocking actuation of the cutting instrument by the motor in the absence of an unexpended staple cartridge in the instrument, detecting the current through the motor resulting from the blocked actuation of the cutting instrument, and interrupting the current through the motor based on the detected current.

FIGURES

Various embodiments of the present application are described herein by way of example in conjunction with the following figures wherein.

Figure 12:
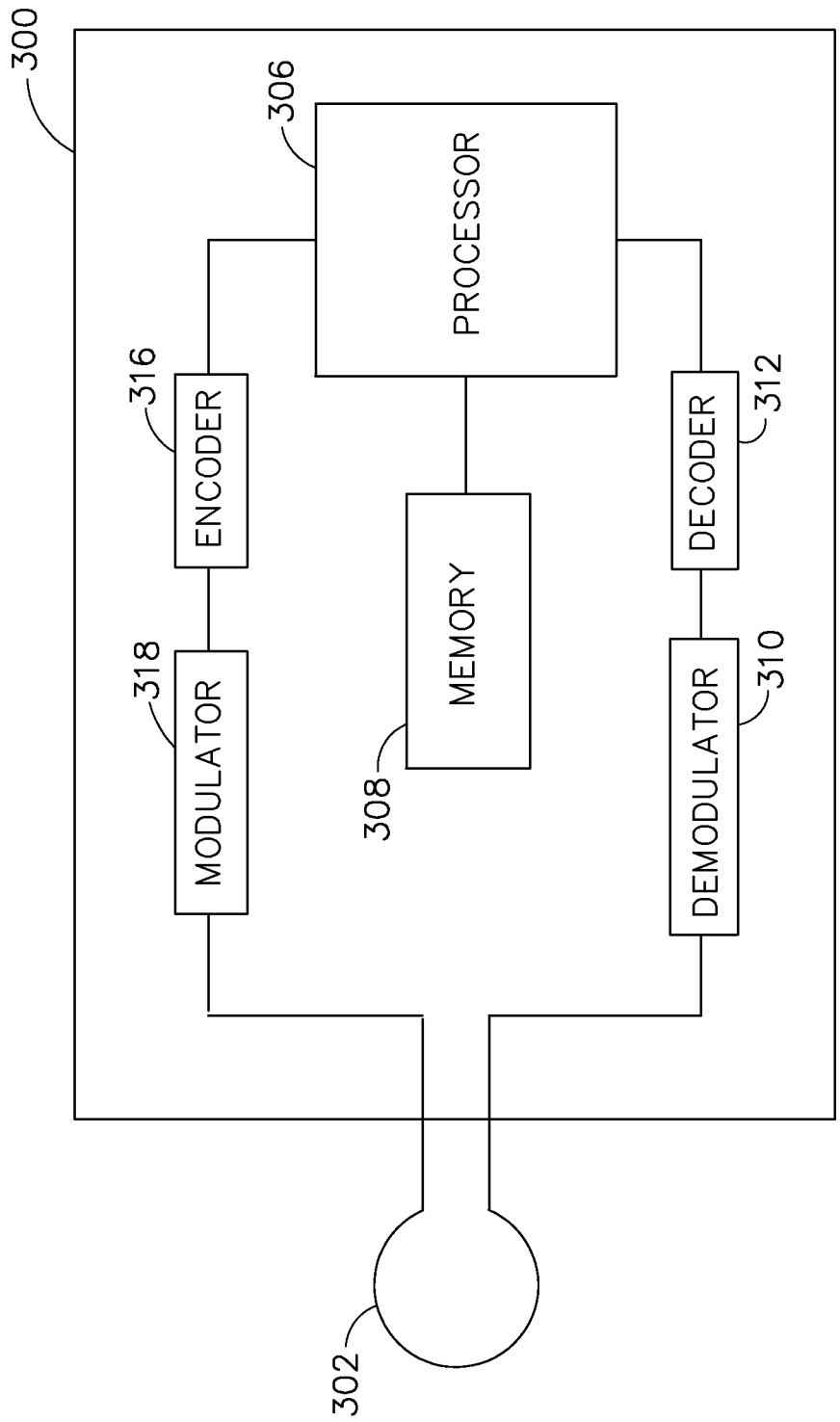
Figure 15:
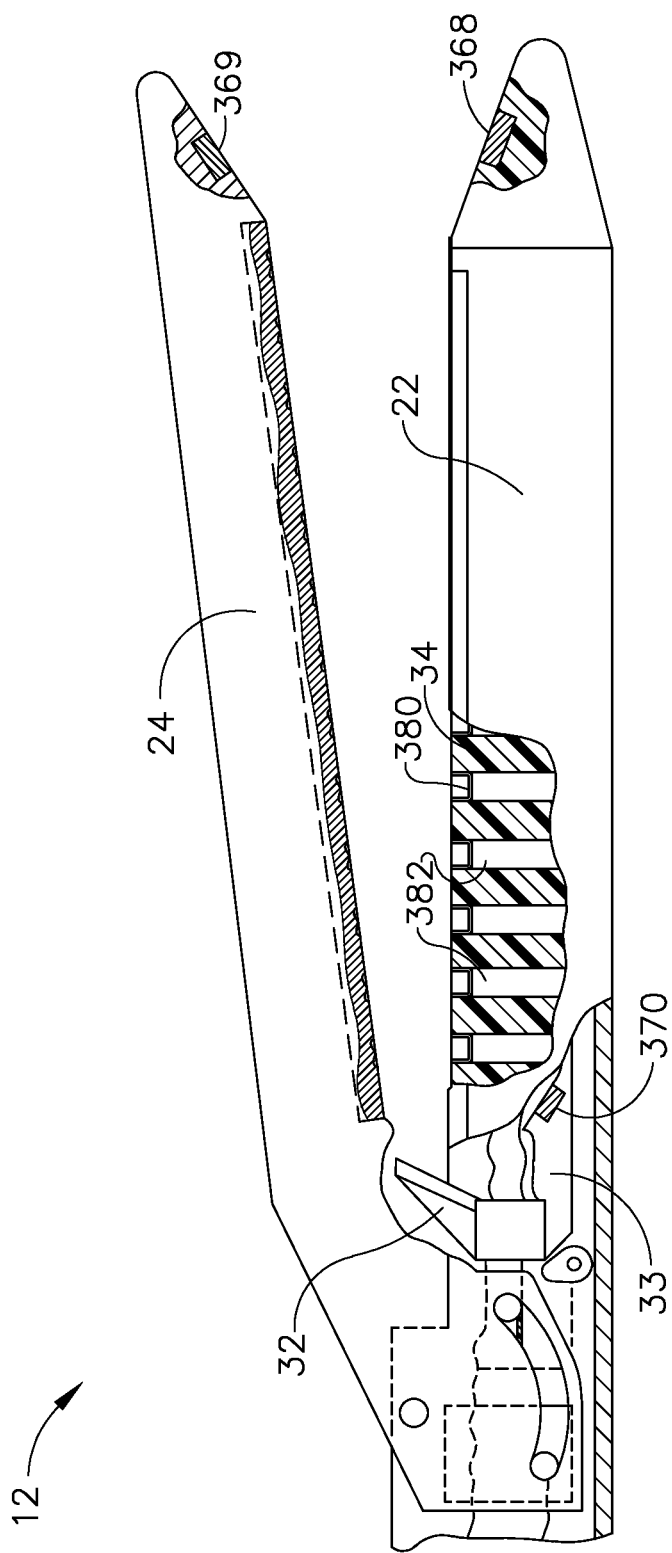
Figure 19:
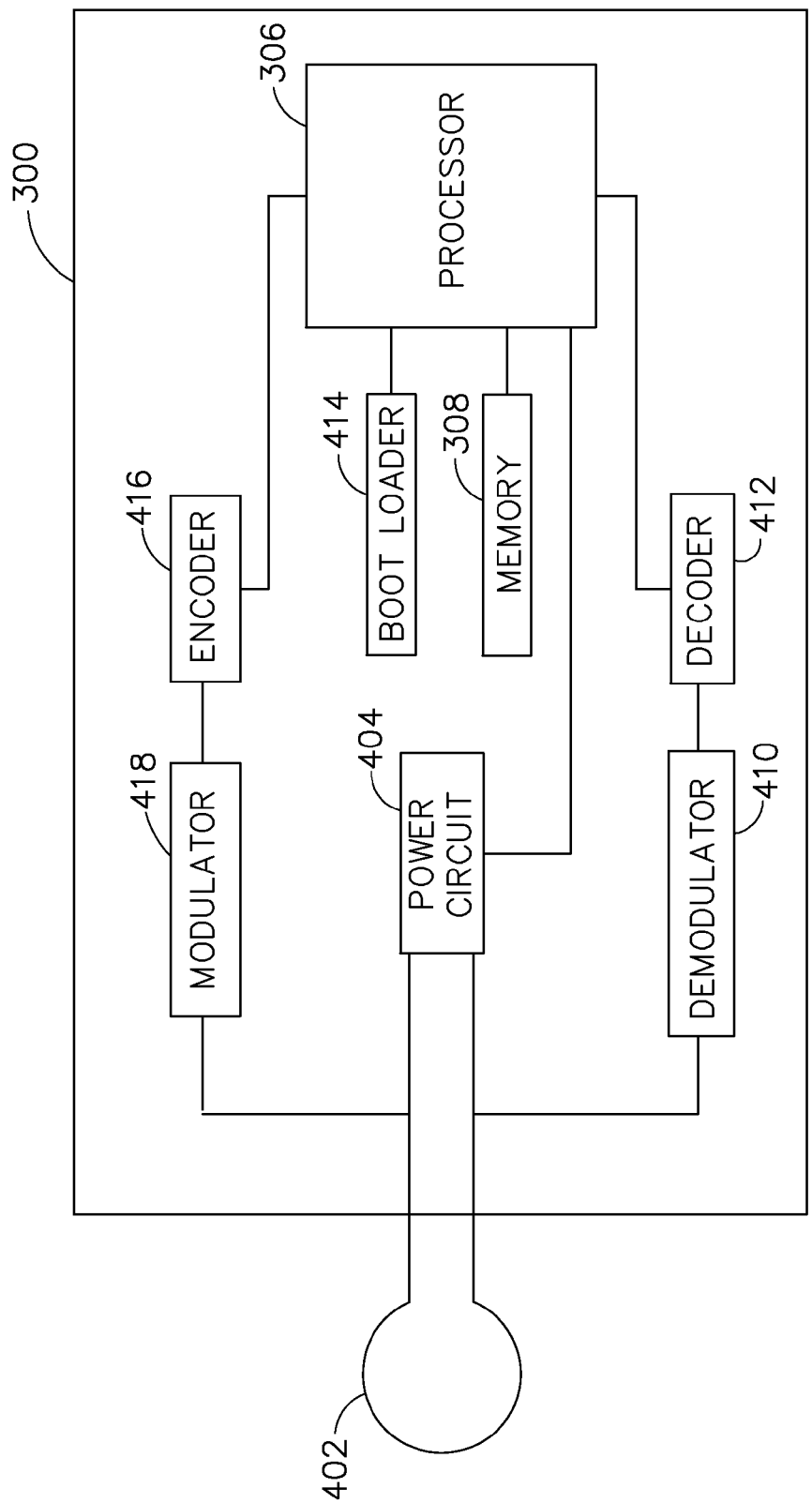
Figure 20:
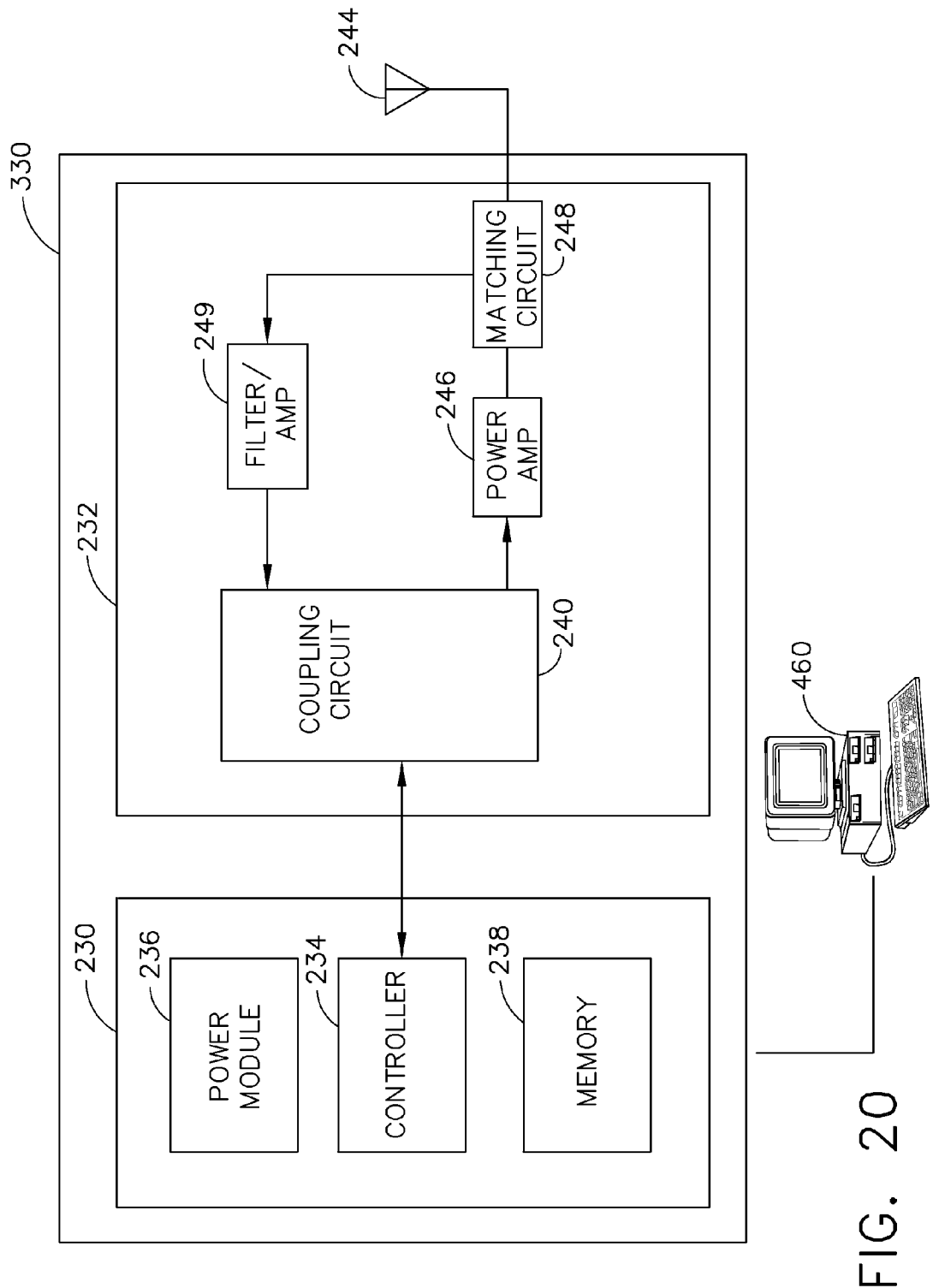
Figure 21:
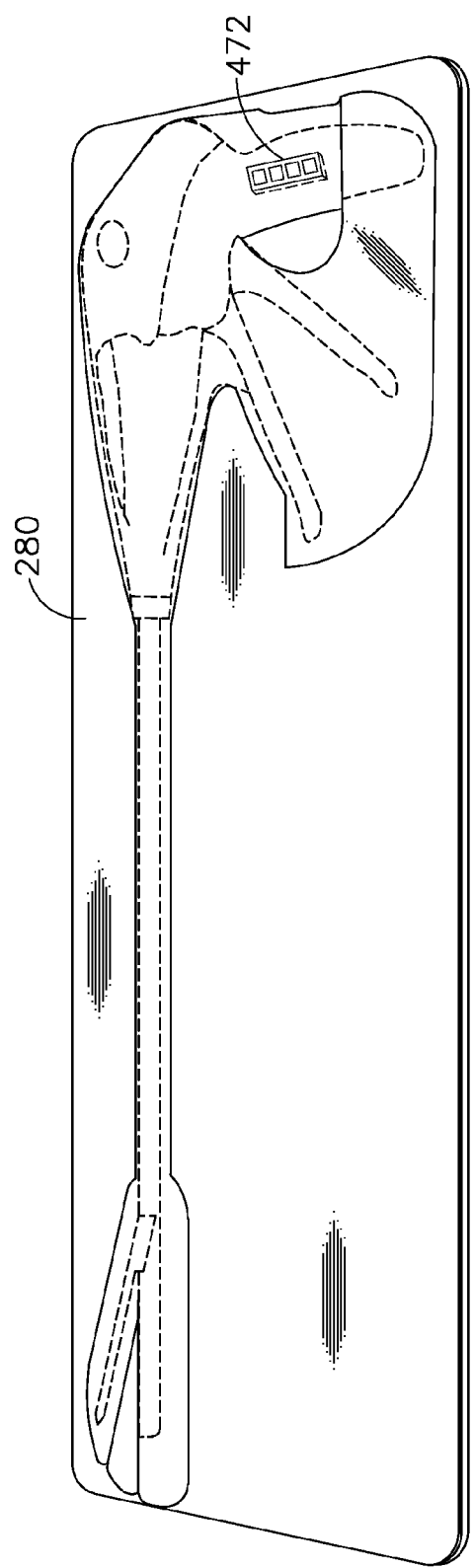
Figure 23:
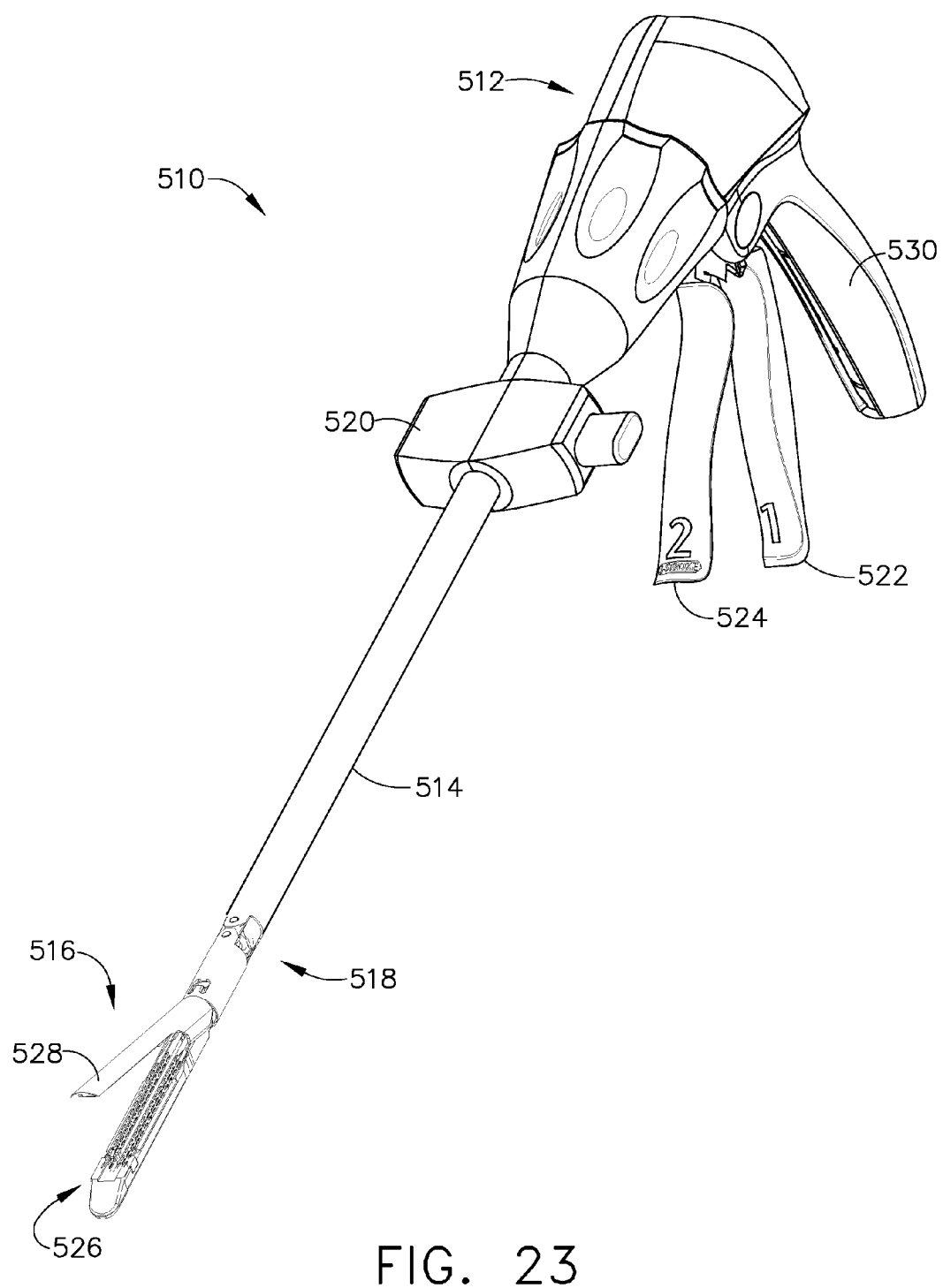
Figure 24:
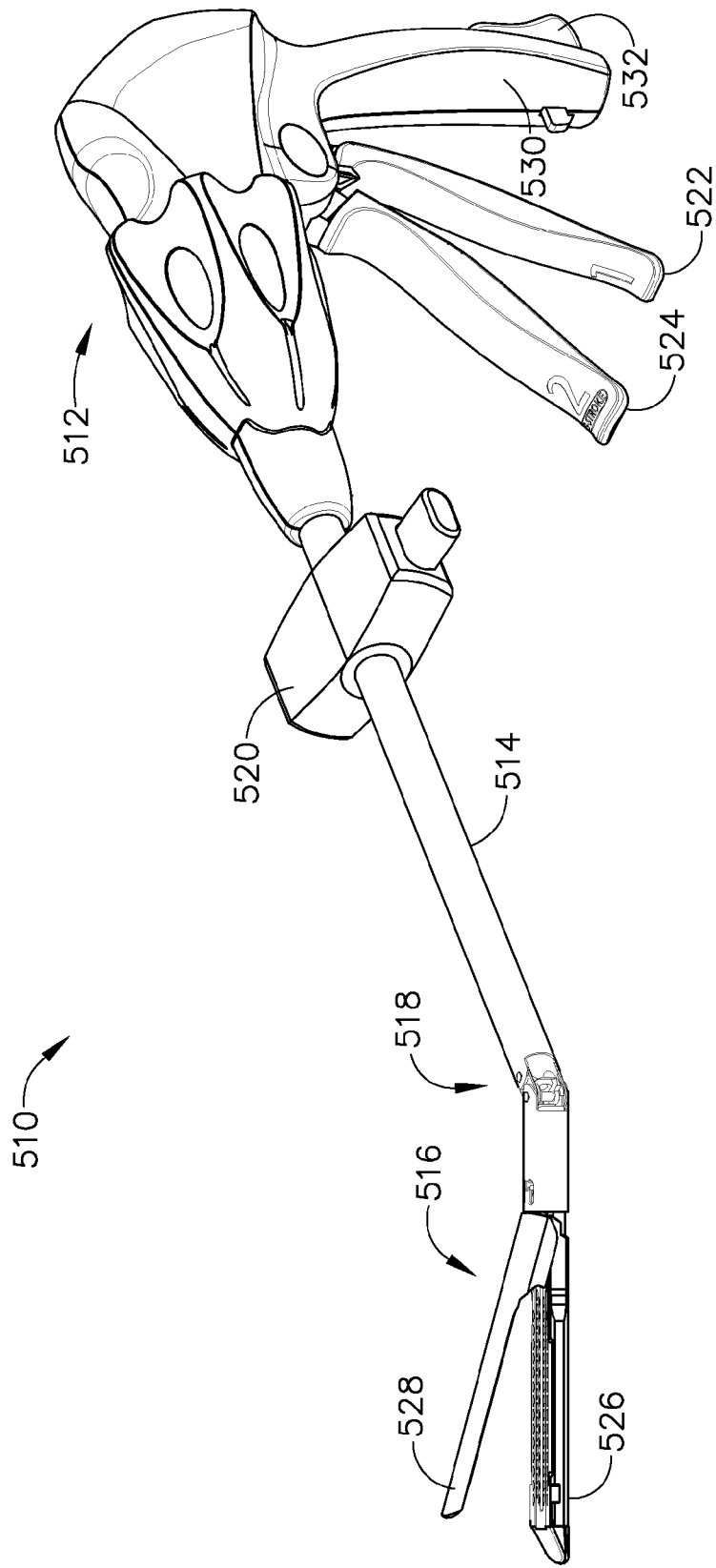
Figure 25:
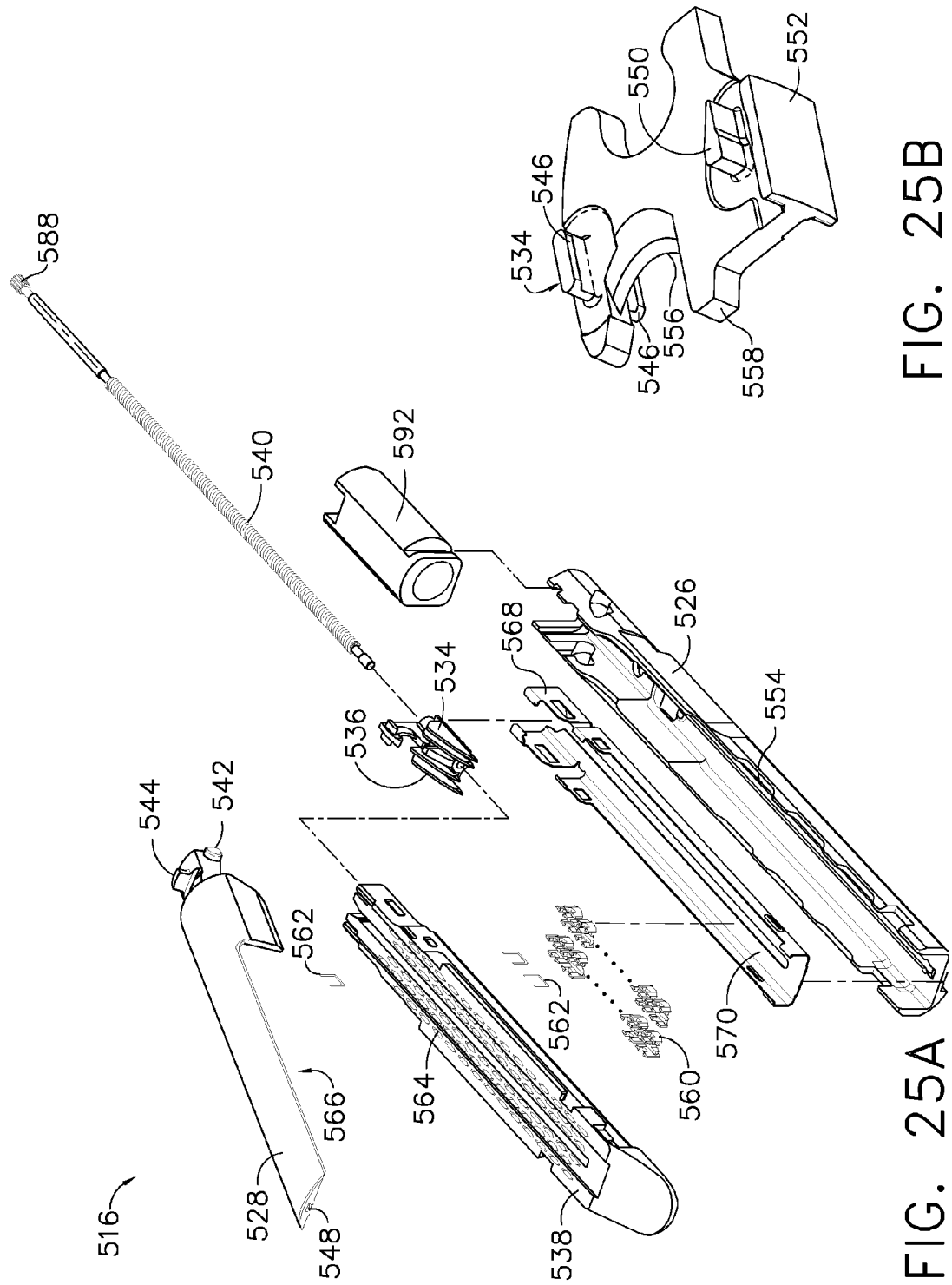
Figure 26:
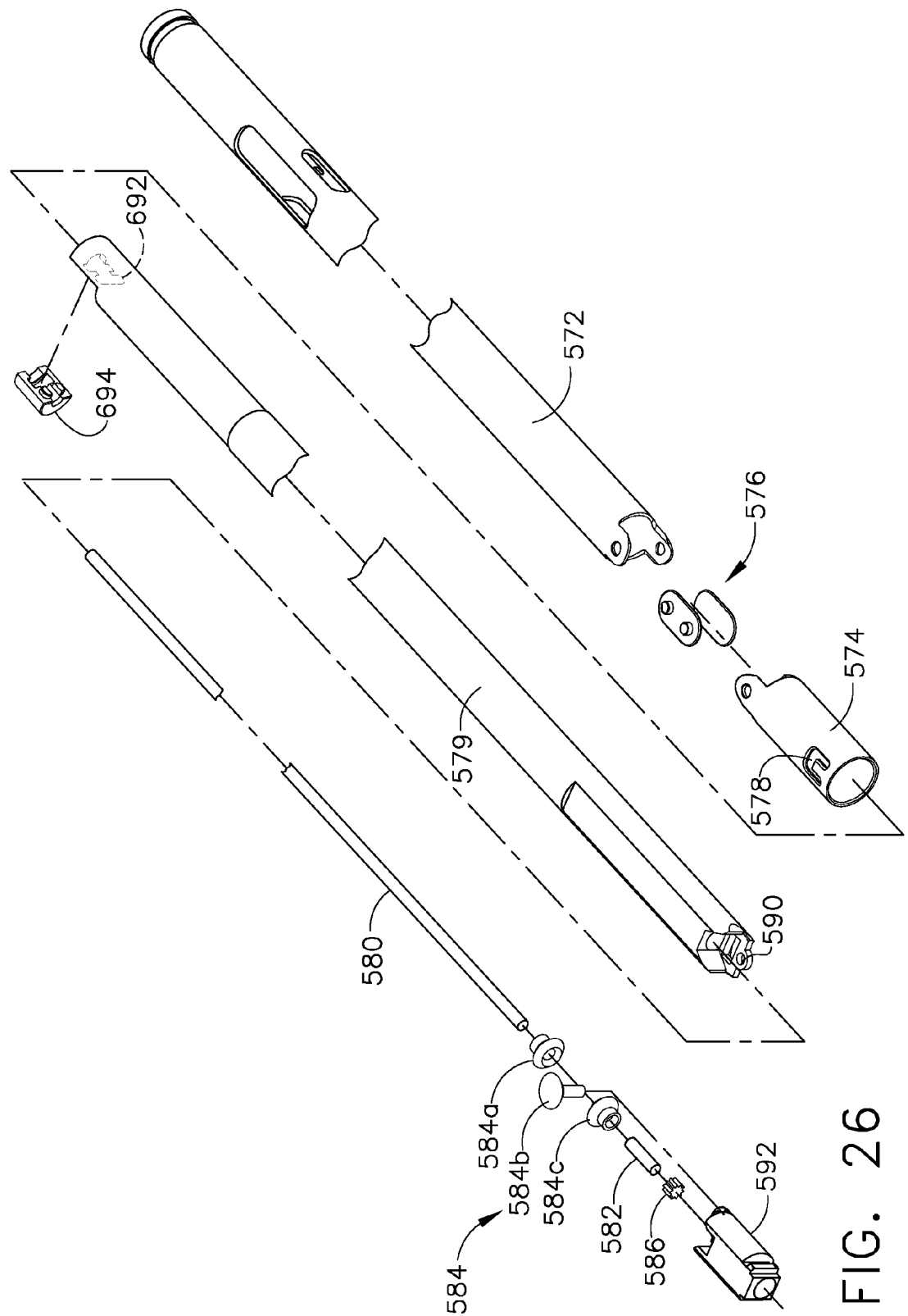
Figure 27:
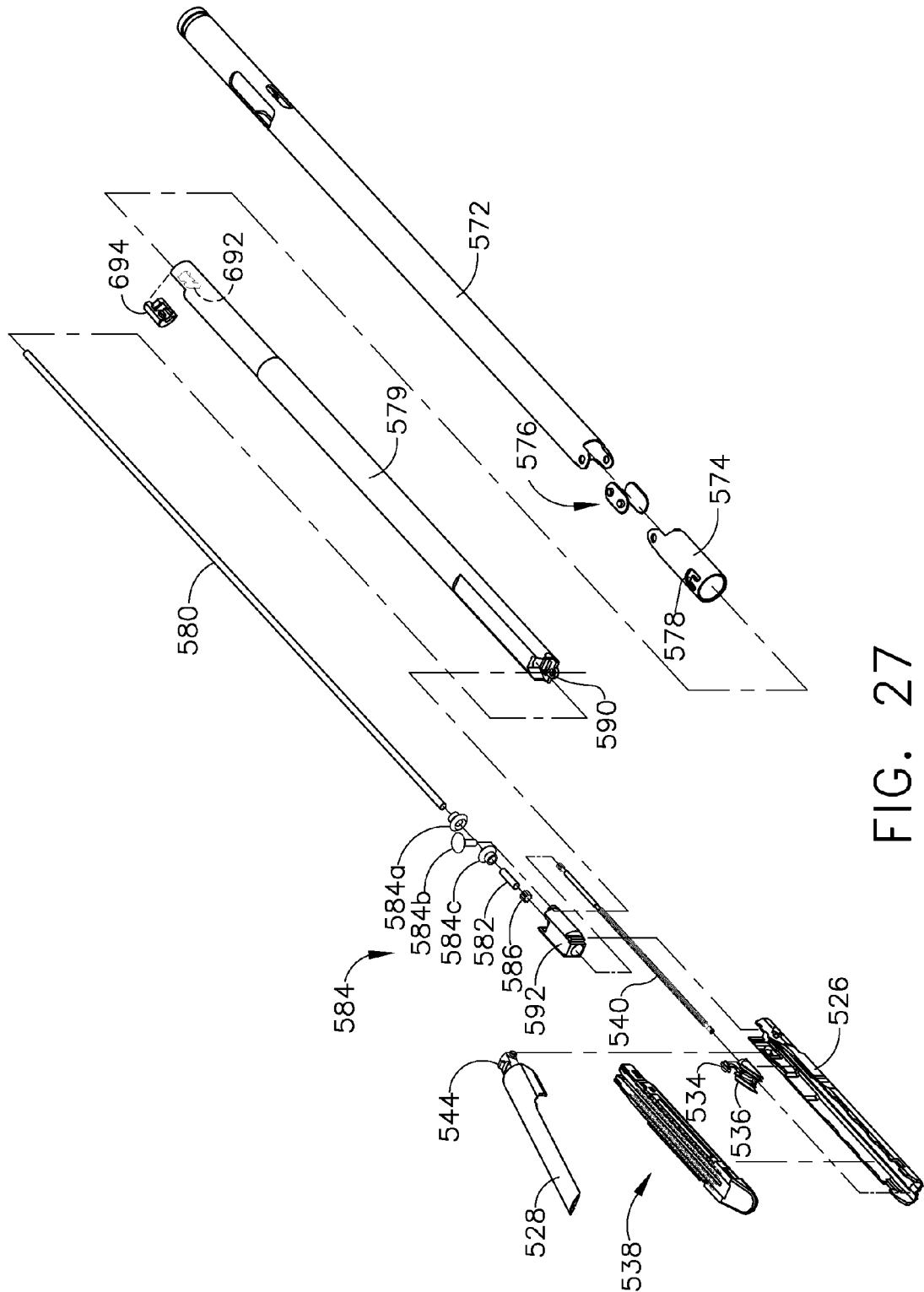
Figure 28:
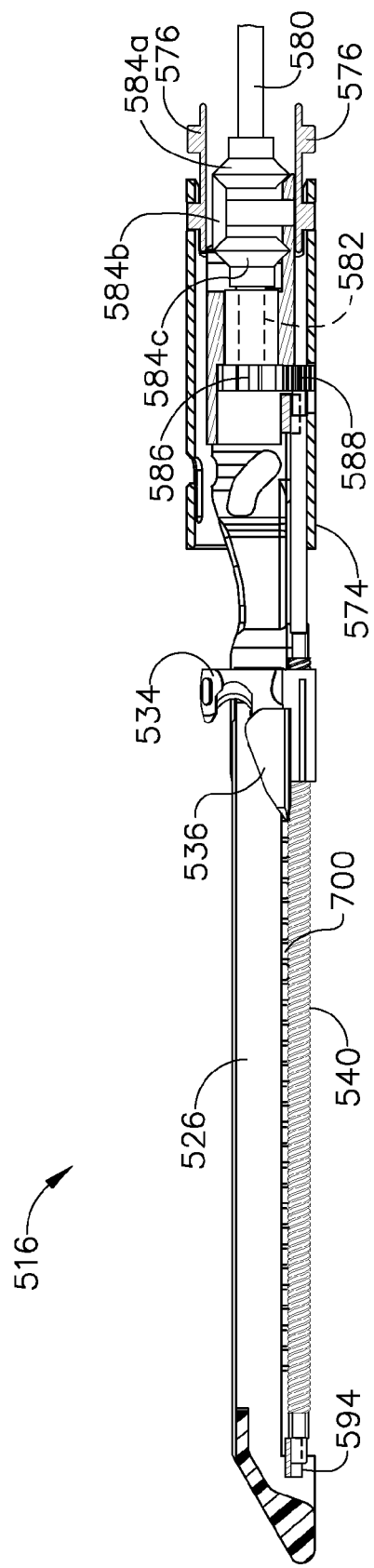
Figure 29:
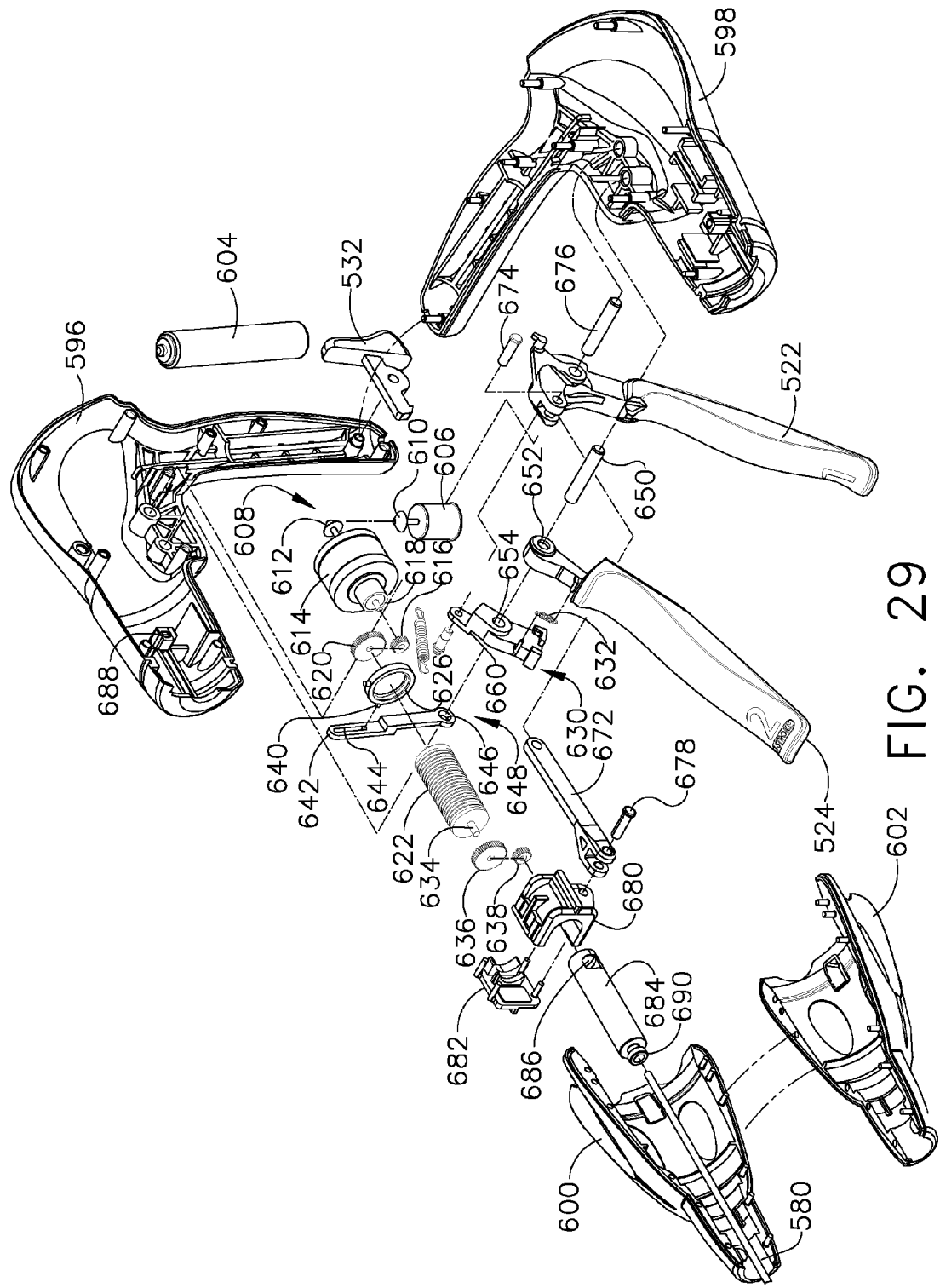
Figure 30:
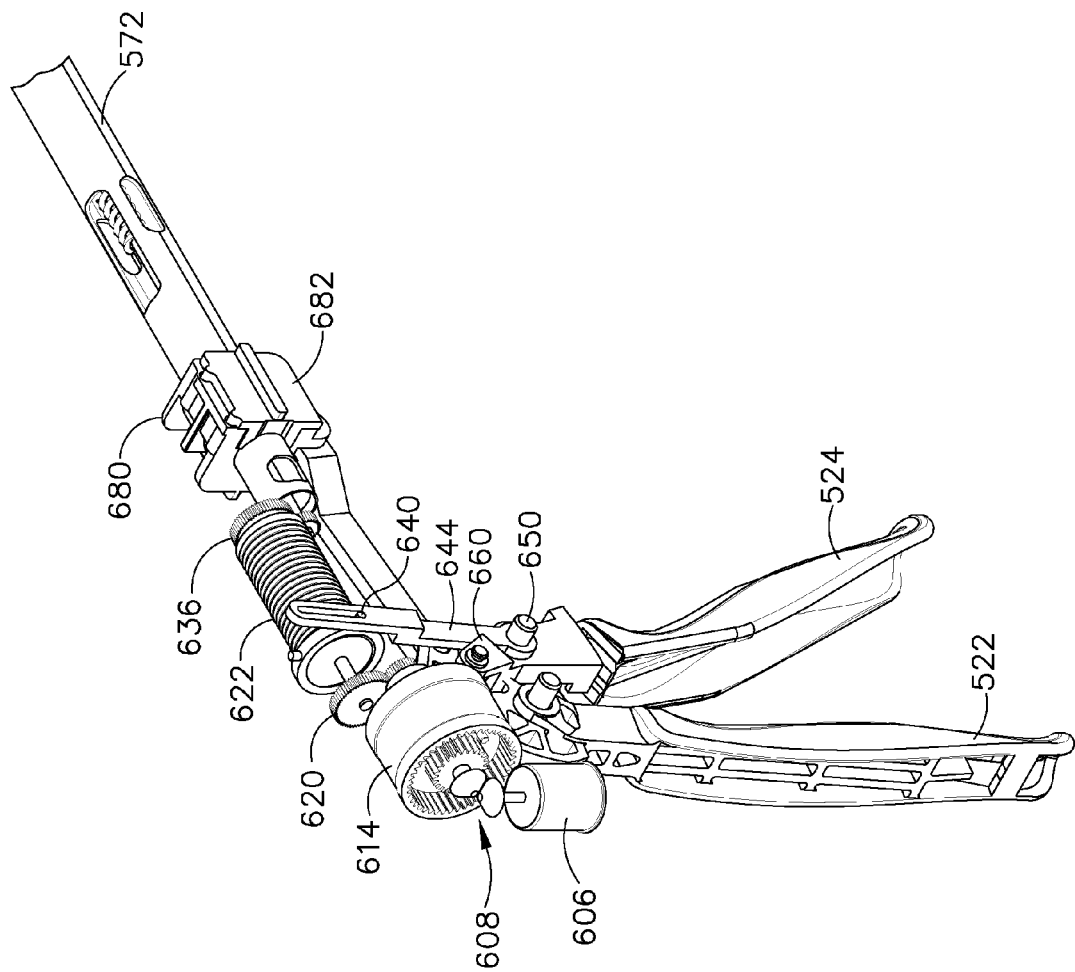
Figure 31:
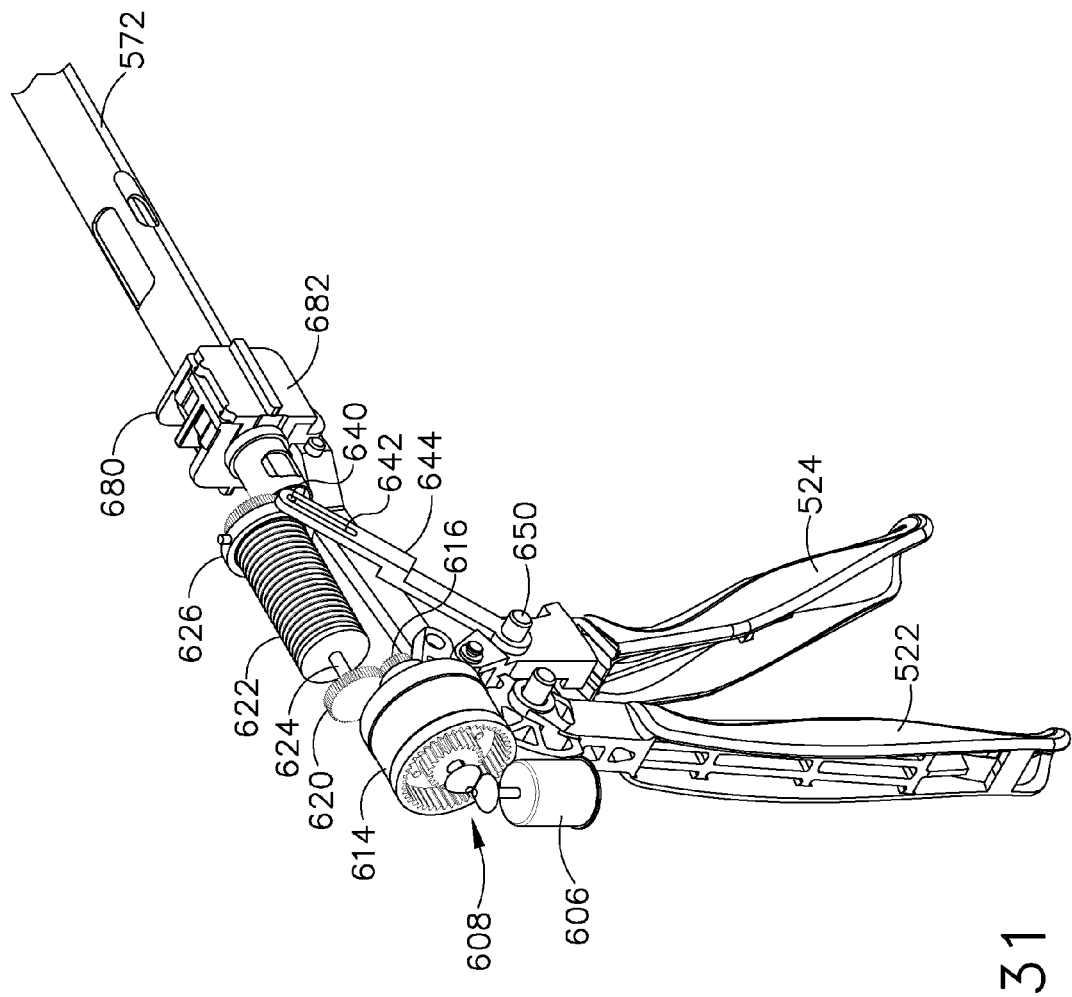
Figure 32:
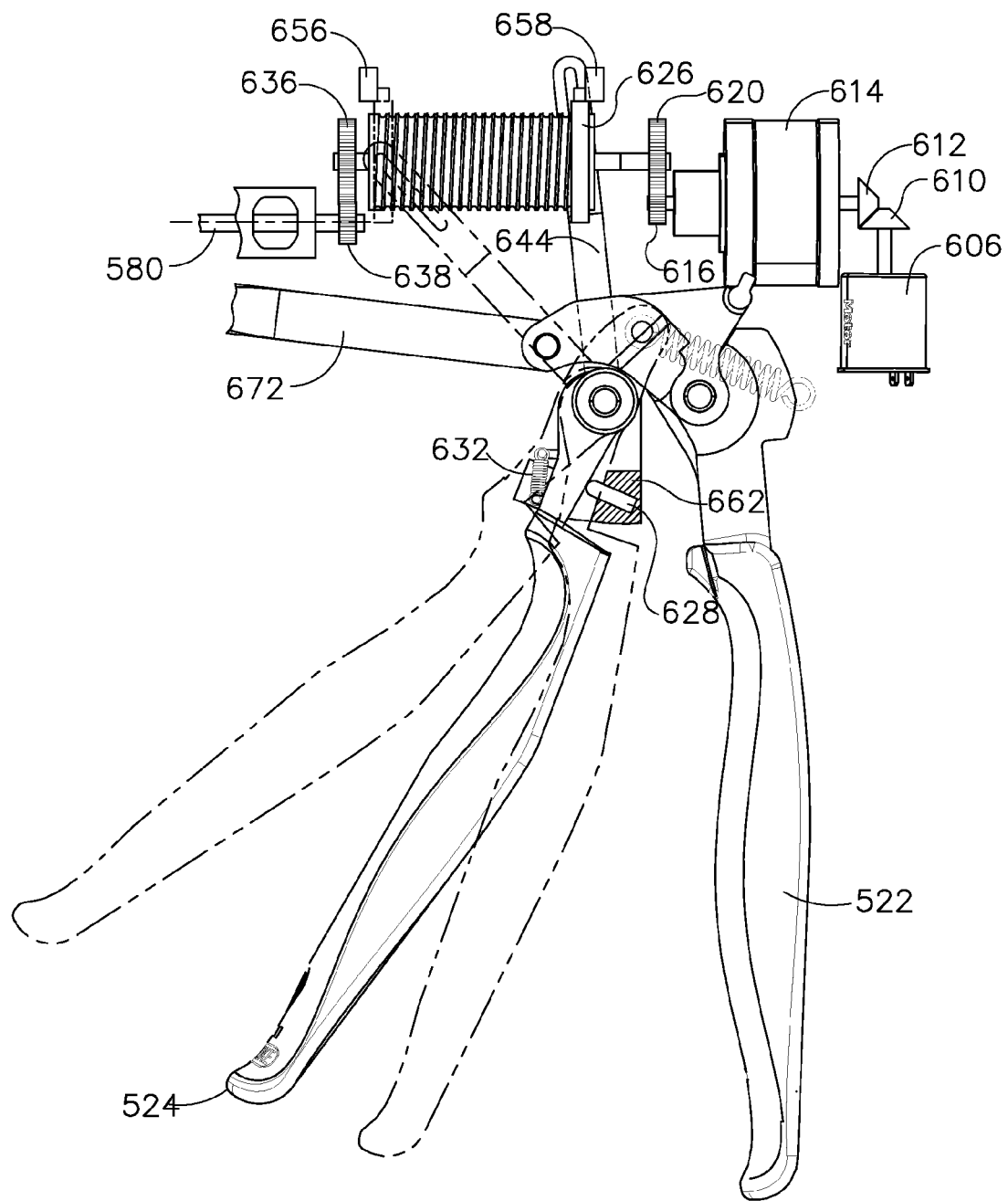
Figure 33:
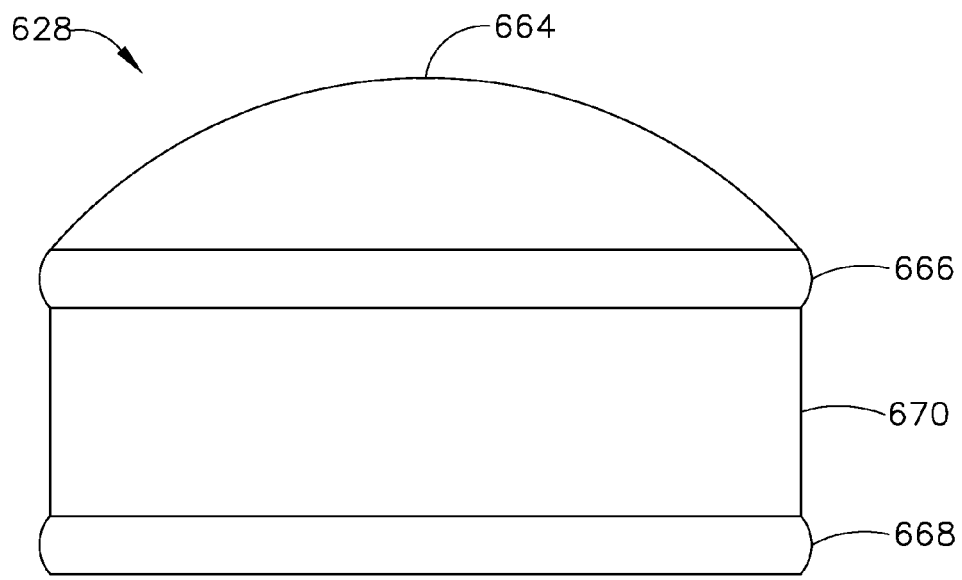
Figure 34:
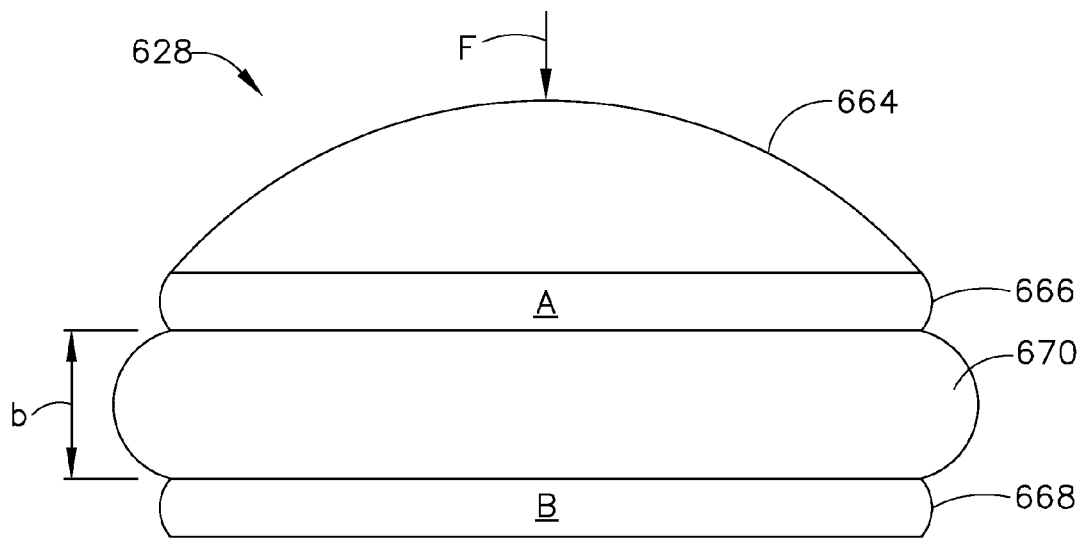
Figure 50:
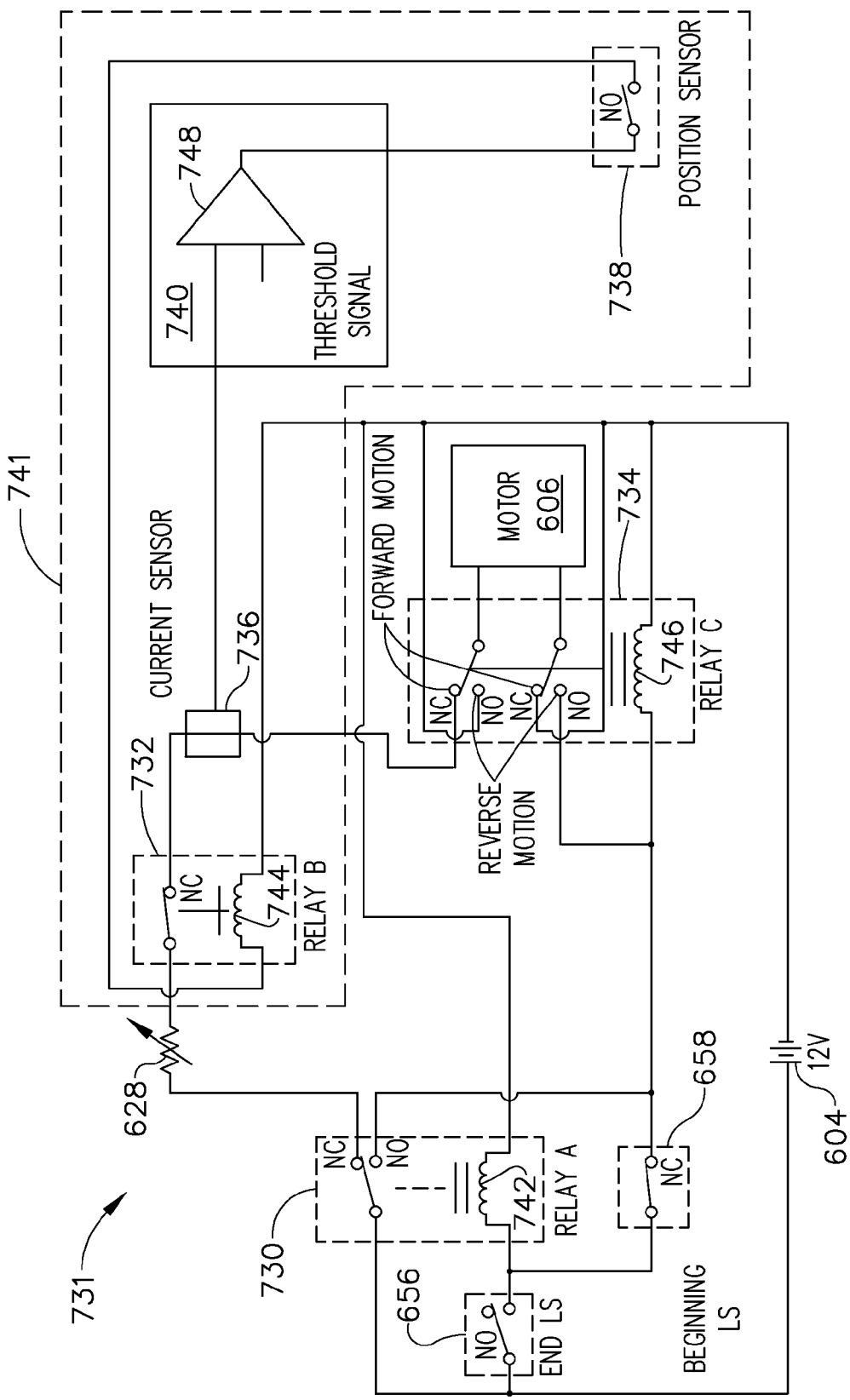
Figure 51:
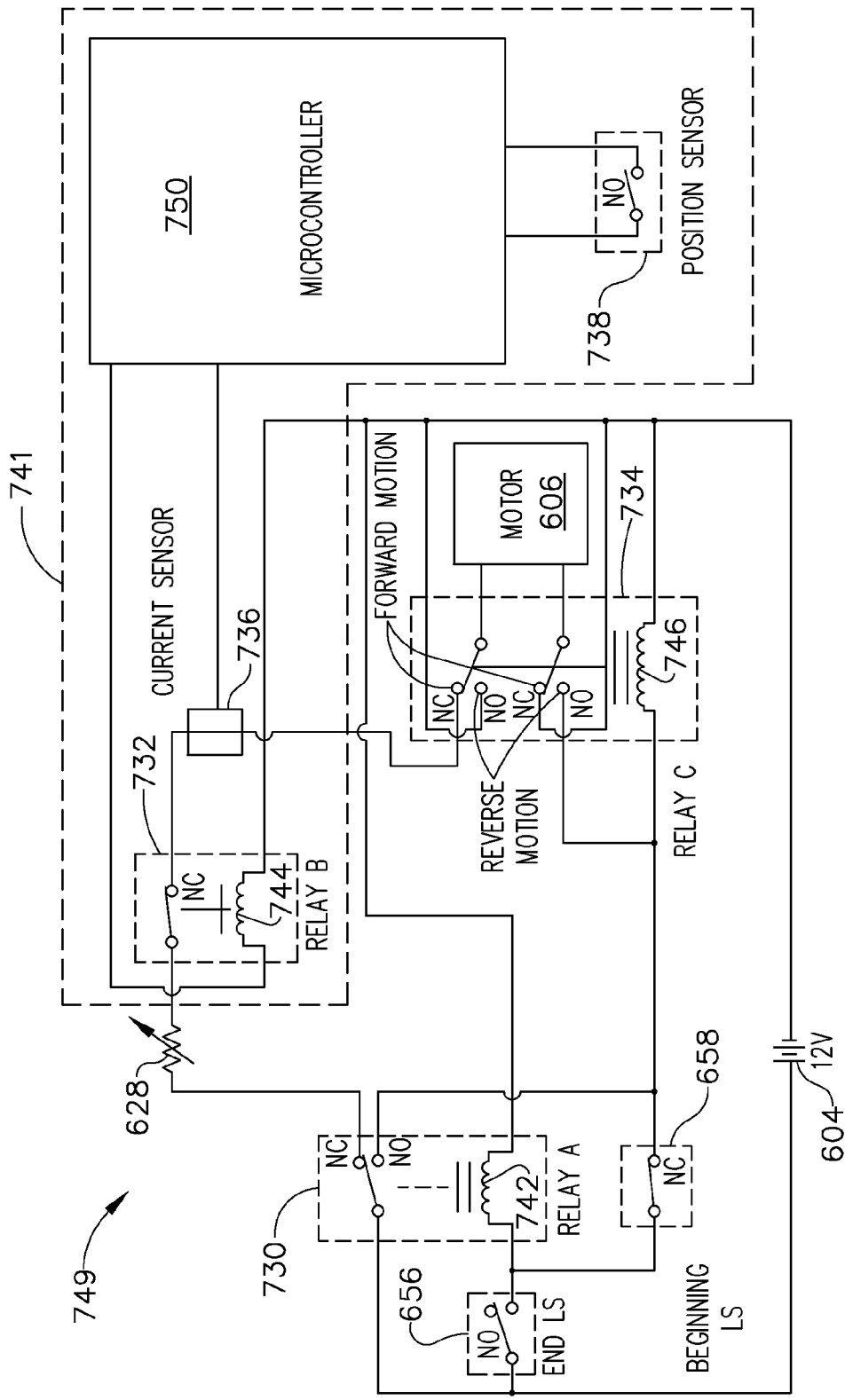
Figure 52:
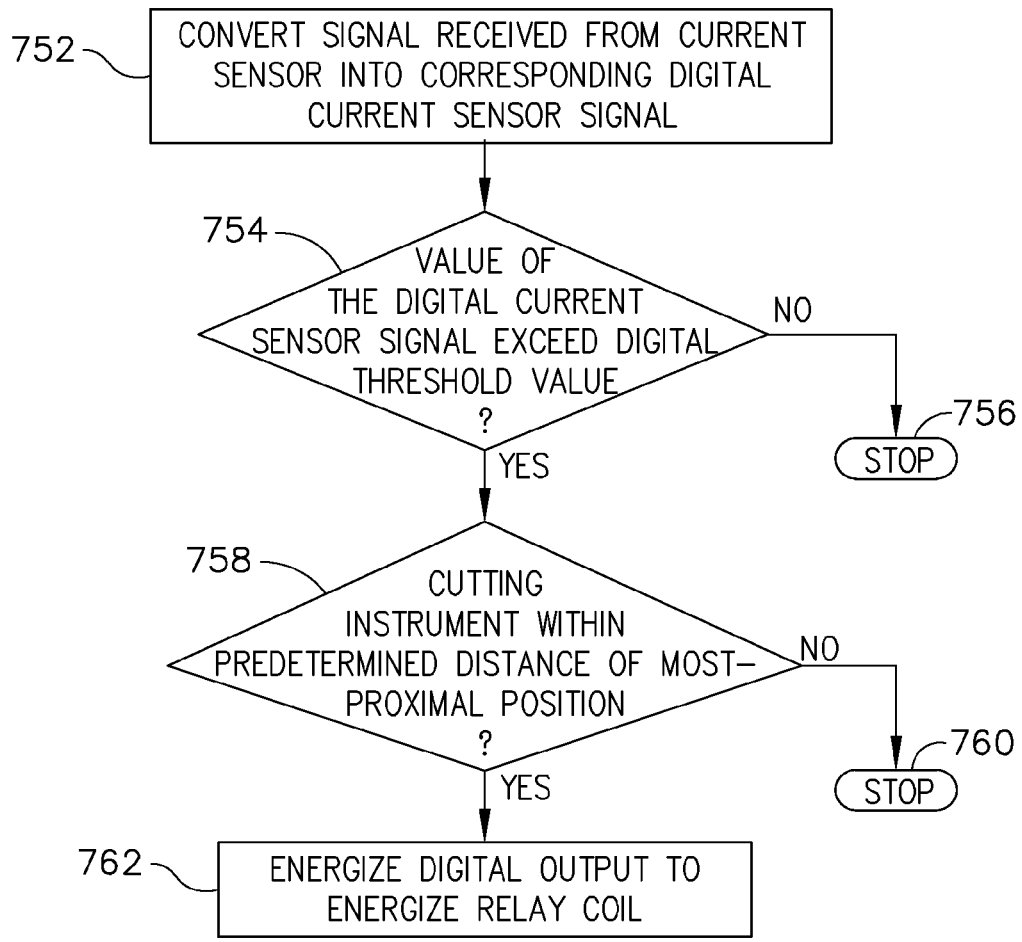
Figure 53:
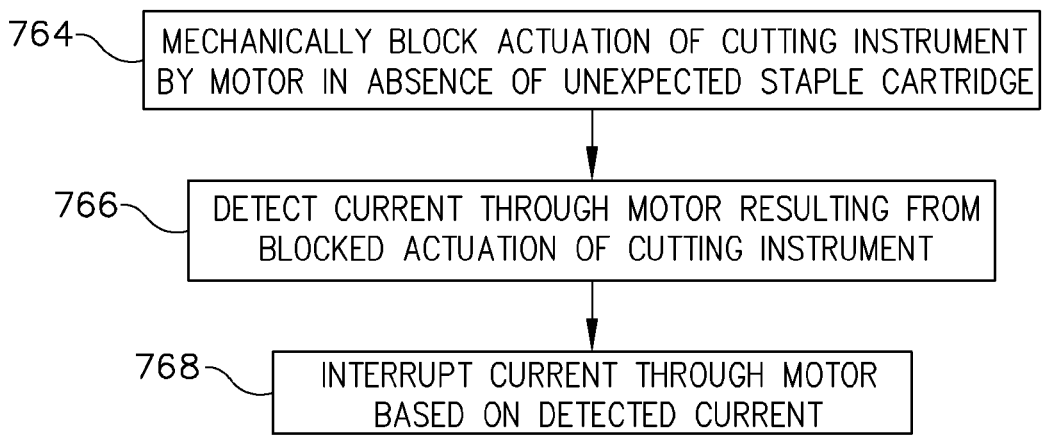

FIGS. 11, 13-14, 16, and 22 are perspective views of a surgical instrument according to various embodiments of the present application;

FIGS. 12 and 19 are block diagrams of a control unit according to various embodiments of the present application;

FIG. 15 is a side view of an end effector including a sensor transponder according to various embodiments of the present application;

FIGS. 17 and 18 show the instrument in a sterile container according to various embodiments of the present application;

FIG. 20 is a block diagram of the remote programming device according to various embodiments of the present application;

FIG. 21 is a diagram of a packaged instrument according to various embodiments of the present application;

FIGS. 23 and 24 are perspective views of a surgical cutting and fastening instrument according to various embodiments of the present application;

FIG. 25A is an exploded view of the end effector according to various embodiments of the present application;

FIG. 25B is a perspective view of the cutting instrument of FIG. 25A;

FIGS. 26 and 27 are exploded views of an end effector and shaft of the instrument according to various embodiments of the present application;

FIG. 28 is a side view of the end effector according to various embodiments of the present application;

FIG. 29 is an exploded view of the handle of the instrument according to various embodiments of the present application;

FIGS. 30 and 31 are partial perspective views of the handle according to various embodiments of the present application;

FIG. 32 is a side view of the handle according to various embodiments of the present application;

FIGS. 33-34 illustrate a proportional sensor that may be used according to various embodiments of the present application;

FIGS. 35-49 illustrate mechanical blocking mechanisms and the sequential operation of each according to various embodiments of the present application;

FIGS. 50-51 illustrate schematic diagrams of circuits used in the instrument according to various embodiments of the present application;

FIG. 52 is a flow diagram of a process implemented by the microcontroller of FIG. 51 according to various embodiments of the present application; and FIG. 53 is a flow diagram of a process implemented by an interlock according to various embodiments of the present application.

DETAILED DESCRIPTION

Various embodiments of the present application are directed generally to a surgical instrument having at least one remote sensor transponder and means for communicating power and/or data signals to the transponder(s) from a control unit. Embodiments of the present application may be used with any type of surgical instrument comprising at least one sensor transponder, such as endoscopic or laparoscopic surgical instruments, but is particularly useful for surgical instruments where some feature of the instrument, such as a free rotating joint, prevents or otherwise inhibits the use of a wired connection to the sensor(s). Before describing aspects of the system, one type of surgical instrument in which embodiments of the present application may be used—an endoscopic stapling and cutting instrument (i.e., an endocutter)—is first described by way of illustration.

Figure 1:
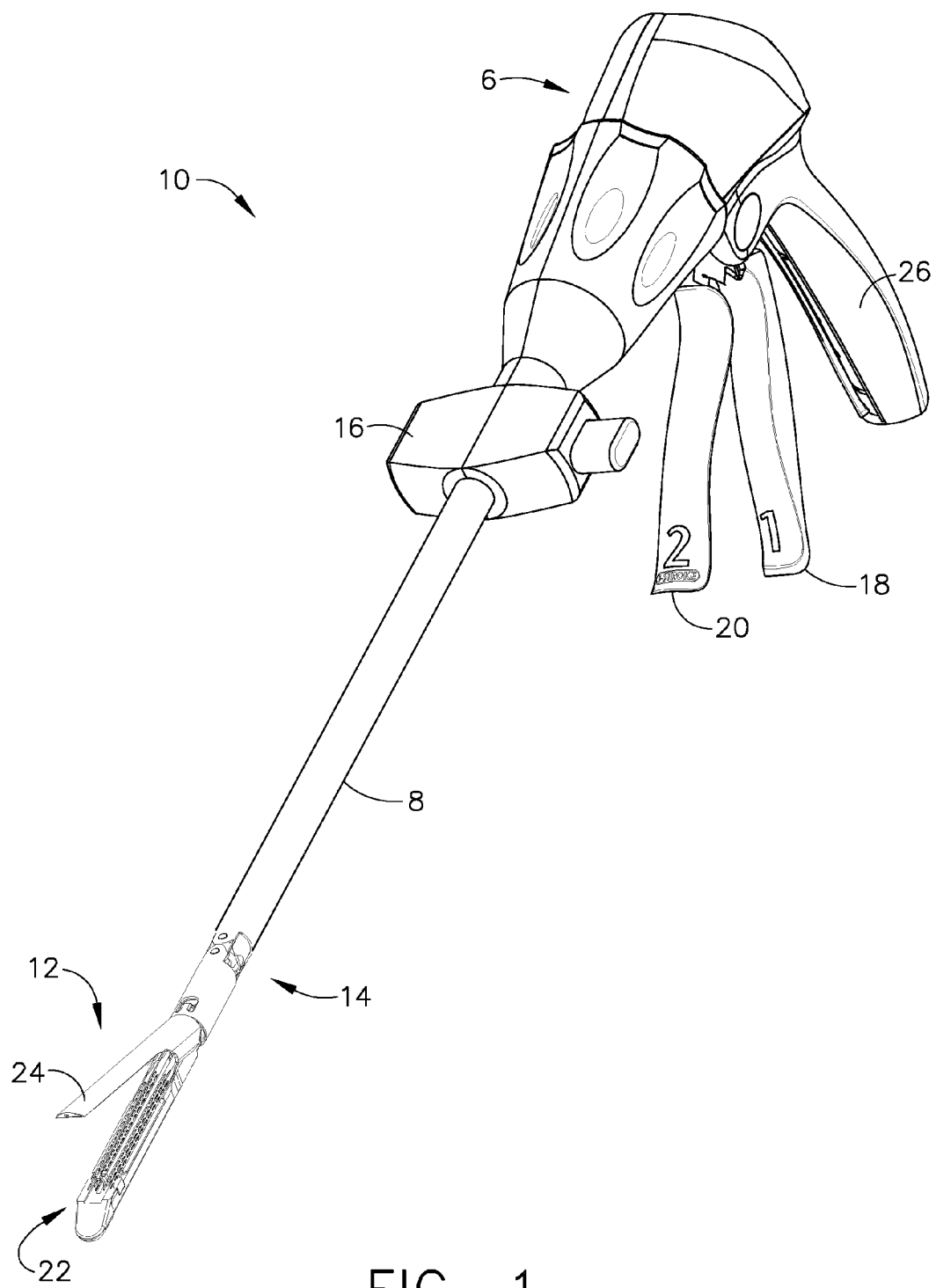
FIGS. 1 and 2 are perspective views of a surgical instrument according to various embodiments of the present application.
Figure 2:
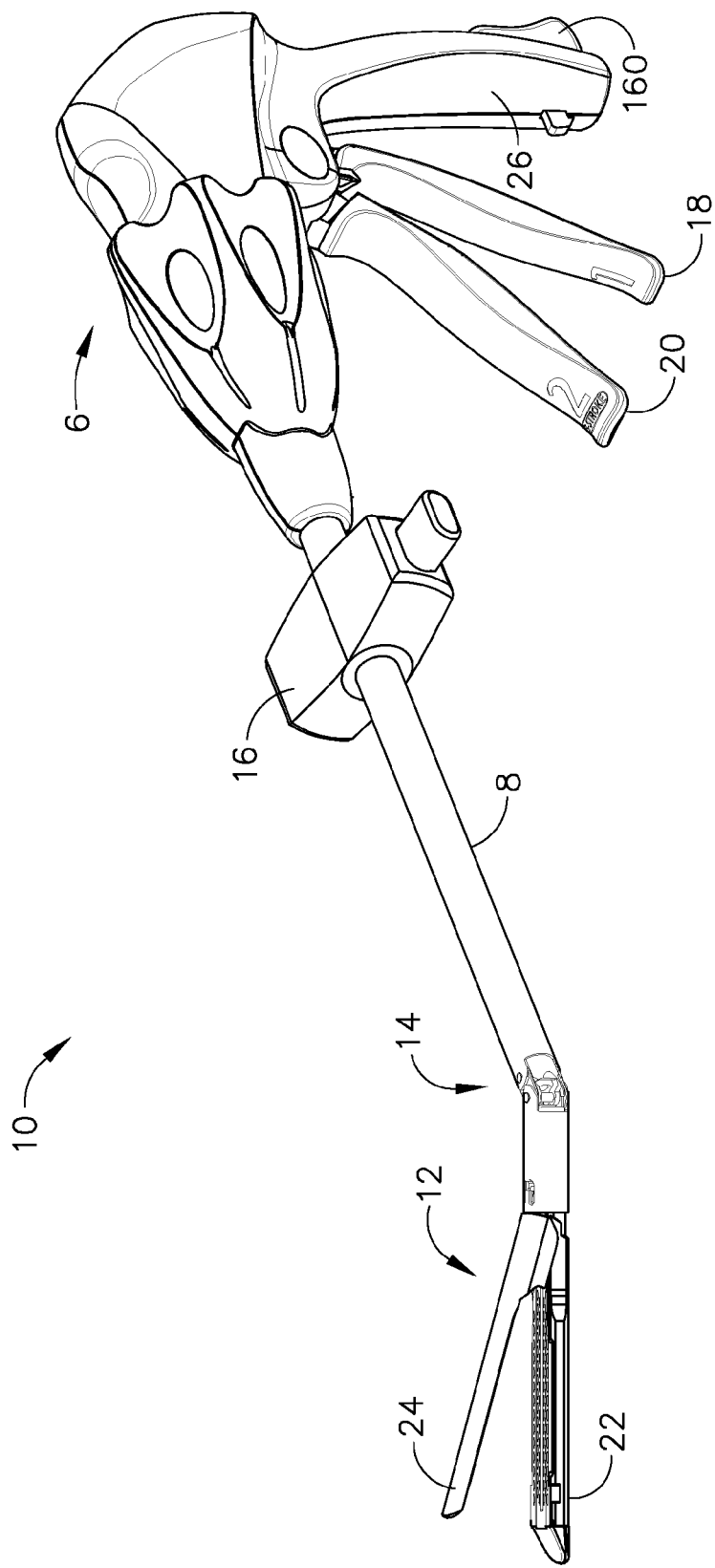

FIGS. 1 and 2 depict an endoscopic surgical instrument 10 that comprises a handle 6, a shaft 8, and an articulating end effector 12 pivotally connected to the shaft 8 at an articulation pivot 14. Correct placement and orientation of the end effector 12 may be facilitated by controls on the hand 6, including (1) a rotation knob 28 for rotating the closure tube (described in more detail below in connection with FIGS. 4-5) at a free rotating joint 29 of the shaft 8 to thereby rotate the end effector 12 and (2) an articulation control 16 to effect rotational articulation of the end effector 12 about the articulation pivot 14. In the illustrated embodiment, the end effector 12 is configured to act as an endocutter for clamping, severing and stapling tissue, although in other embodiments, different types of end effectors may be used, such as end effectors for other types of surgical instruments, such as graspers, cutters, staplers, clip appliers, access devices, drug/gene therapy devices, ultrasound, RF or laser devices, etc.

The handle 6 of the instrument 10 may include a closure trigger 18 and a firing trigger 20 for actuating the end effector 12. It will be appreciated that instruments having end effectors directed to different surgical tasks may have different numbers or types of triggers or other suitable controls for operating the end effector 12. The end effector 12 is shown separated from the handle 6 by the preferably elongate shaft 8. In one embodiment, a clinician or operator of the instrument 10 may articulate the end effector 12 relative to the shaft 8 by utilizing the articulation control 16, as described in more detail in pending U.S. patent application Ser. No. 11/329,020, filed Jan. 10, 2006, entitled "Surgical Instrument Having An Articulating End Effector," by Geoffrey C. Hueil et al., which is incorporated herein by reference.

The end effector 12 includes in this example, among other things, a staple channel 22 and a pivotally translatable clamping member, such as an anvil 24, which are maintained at a spacing that assures effective stapling and severing of tissue clamped in the end effector 12. The handle 6 includes a pistol grip 26 towards which a closure trigger 18 is pivotally drawn by the clinician to cause clamping or closing of the anvil 24 toward the staple channel 22 of the end effector 12 to thereby clamp tissue positioned between the anvil 24 and channel 22. The firing trigger 20 is farther outboard of the closure trigger 18. Once the closure trigger 18 is locked in the closure position, the firing trigger 20 may rotate slightly toward the pistol grip 26 so that it can be reached by the operator using one hand. Then the operator may pivotally draw the firing trigger 20 toward the pistol grip 12 to cause the stapling and severing of clamped tissue in the end effector 12. The '573 application describes various configurations for locking and unlocking the closure trigger 18. In other embodiments, different types of clamping members besides the anvil 24 could be used, such as, for example, an opposing jaw, etc.

It will be appreciated that the terms "proximal" and "distal" are used herein with reference to a clinician gripping the handle 6 of an instrument 10. Thus, the end effector 12 is distal with respect to the more proximal handle 6. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

The closure trigger 18 may be actuated first. Once the clinician is satisfied with the positioning of the end effector 12, the clinician may draw back the closure trigger 18 to its fully closed, locked position proximate to the pistol grip 26. The firing trigger 20 may then be actuated. The firing trigger 20 returns to the open position (shown in FIGS. 1 and 2) when the clinician removes pressure. A release button 30 on the handle 6, and in this example, on the pistol grip 26 of the handle, when depressed may release the locked closure trigger 18.

Figure 3:
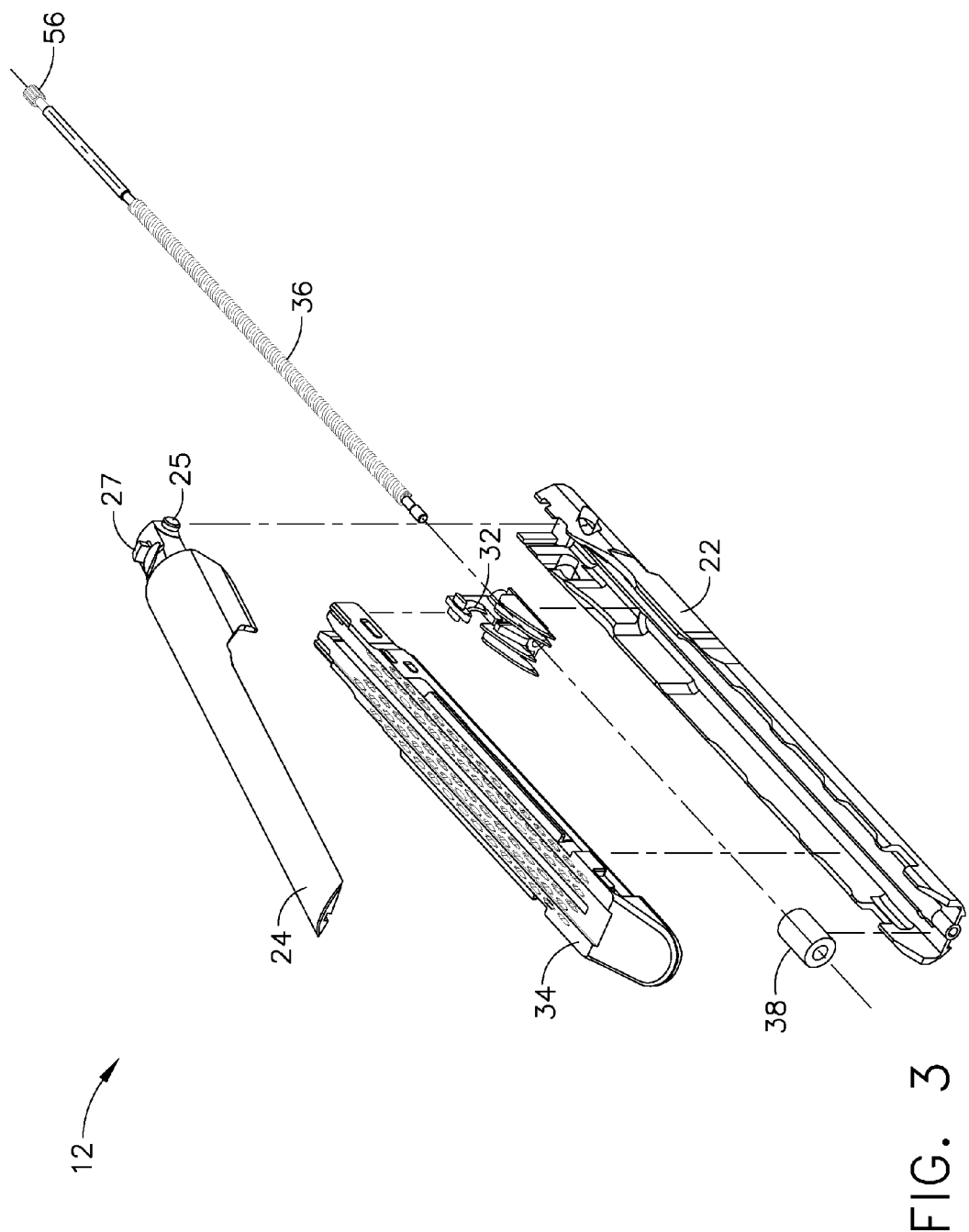
FIGS. 3-5 are exploded views of an end effector and shaft of the instrument according to various embodiments of the present application.

FIG. 3 is an exploded view of the end effector 12 according to various embodiments. As shown in the illustrated embodiment, the end effector 12 may include, in addition to the previously-mentioned channel 22 and anvil 24, a cutting instrument 32, a sled 33, a staple cartridge 34 that is removably seated in the channel 22, and a helical screw shaft 36. The cutting instrument 32 may be, for example, a knife. The anvil 24 may be pivotably opened and closed at a pivot point 25 connected to the proximate end of the channel 22. The anvil 24 may also include a tab 27 at its proximate end that is inserted into a component of the mechanical closure system (described further below) to open and close the anvil 24. When the closure trigger 18 is actuated, that is, drawn in by a user of the instrument 10, the anvil 24 may pivot about the pivot point 25 into the clamped or closed position. If clamping of the end effector 12 is satisfactory, the operator may actuate the firing trigger 20, which, as explained in more detail below, causes the knife 32 and sled 33 to travel longitudinally along the channel 22, thereby cutting tissue clamped within the end effector 12. The movement of the sled 33 along the channel 22 causes the staples of the staple cartridge 34 to be driven through the severed tissue and against the closed anvil 24, which turns the staples to fasten the severed tissue. U.S. Pat. No. 6,978,921, entitled "Surgical stapling instrument incorporating an E-beam firing mechanism," which is incorporated herein by reference, provides more details about such two-stroke cutting and fastening instruments. The sled 33 may be part of the cartridge 34, such that when the knife 32 retracts following the cutting operation, the sled 33 does not retract. The channel 22 and the anvil 24 may be made of an electrically conductive material (such as metal) so that they may serve as part of the antenna that communicates with the sensor(s) in the end effector, as described further below. The cartridge 34 could be made of a nonconductive material (such as plastic) and the sensor may be connected to or disposed in the cartridge 34, as described further below.

It should be noted that although the embodiments of the instrument 10 described herein employ an end effector 12 that staples the severed tissue, in other embodiments different techniques for fastening or sealing the severed tissue may be used. For example, end effectors that use RF energy or adhesives to fasten the severed tissue may also be used. U.S. Pat. No. 5,709,680, entitled "Electrosurgical Hemostatic Device" to Yates et al., and U.S. Pat. No. 5,688,270, entitled "Electro-surgical Hemostatic Device With Recessed And/Or Offset Electrodes" to Yates et al., which are incorporated herein by reference, discloses cutting instruments that use RF energy to fasten the severed tissue. U.S. patent application Ser. No. 11/267,811 to Morgan et al. and U.S. patent application Ser. No. 11/267,383 to Shelton et al., which are also incorporated herein by reference, disclose cutting instruments that use adhesives to fasten the severed tissue. Accordingly, although the description herein refers to cutting/stapling operations and the like, it should be recognized that this is an exemplary embodiment and is not meant to be limiting. Other tissue-fastening techniques may also be used.

Figure 4:
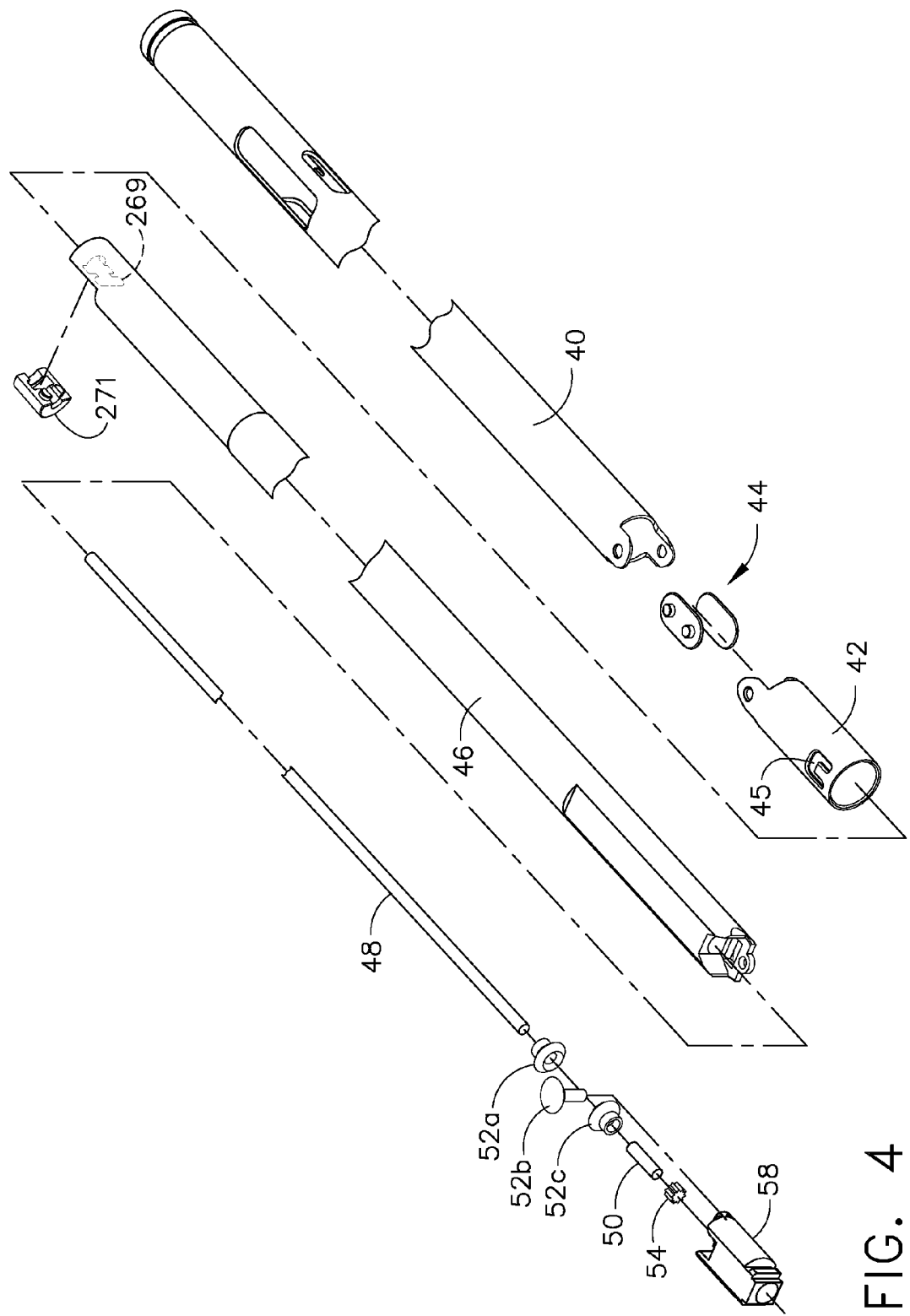
Figure 5:
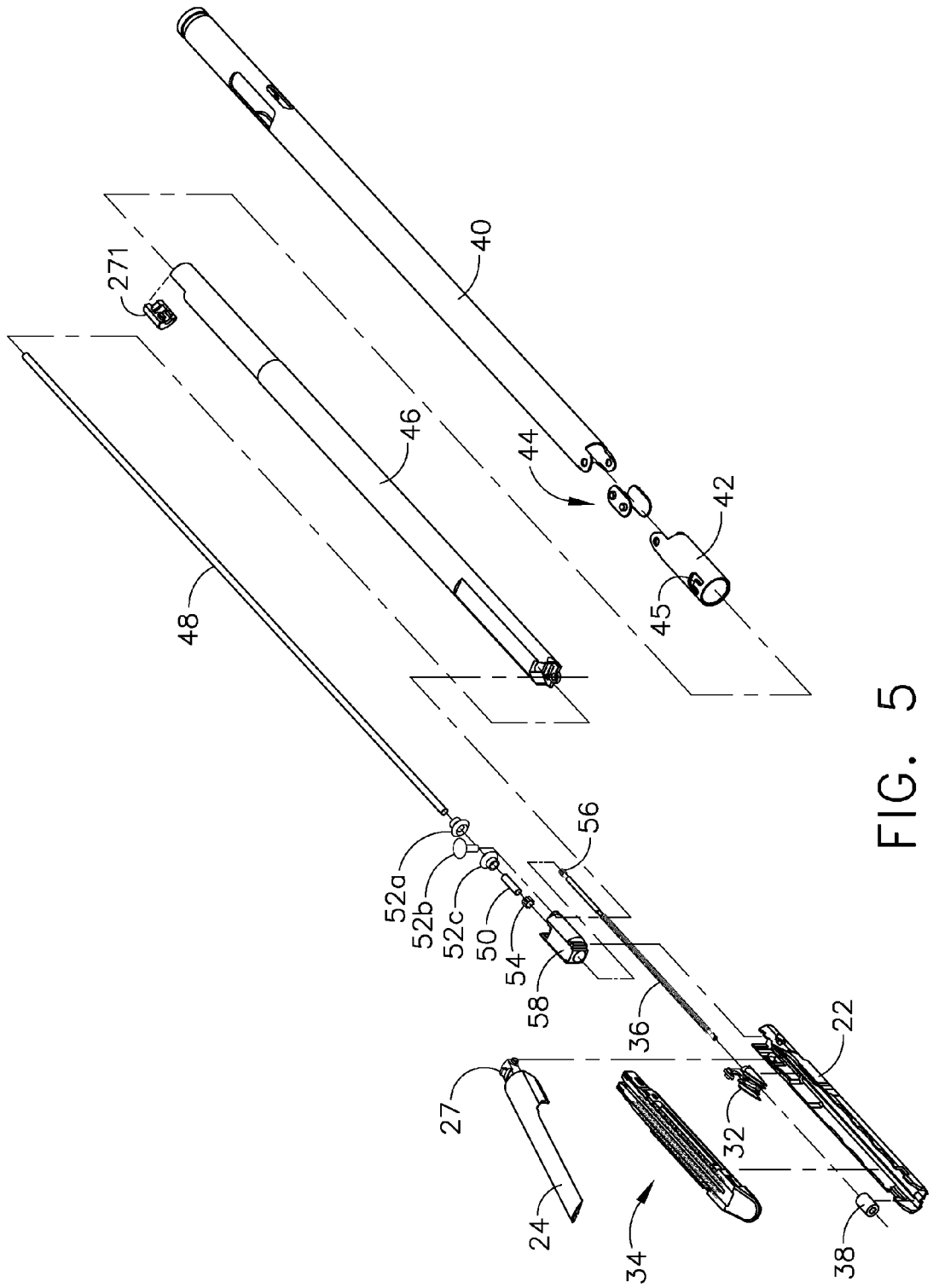
Figure 6:
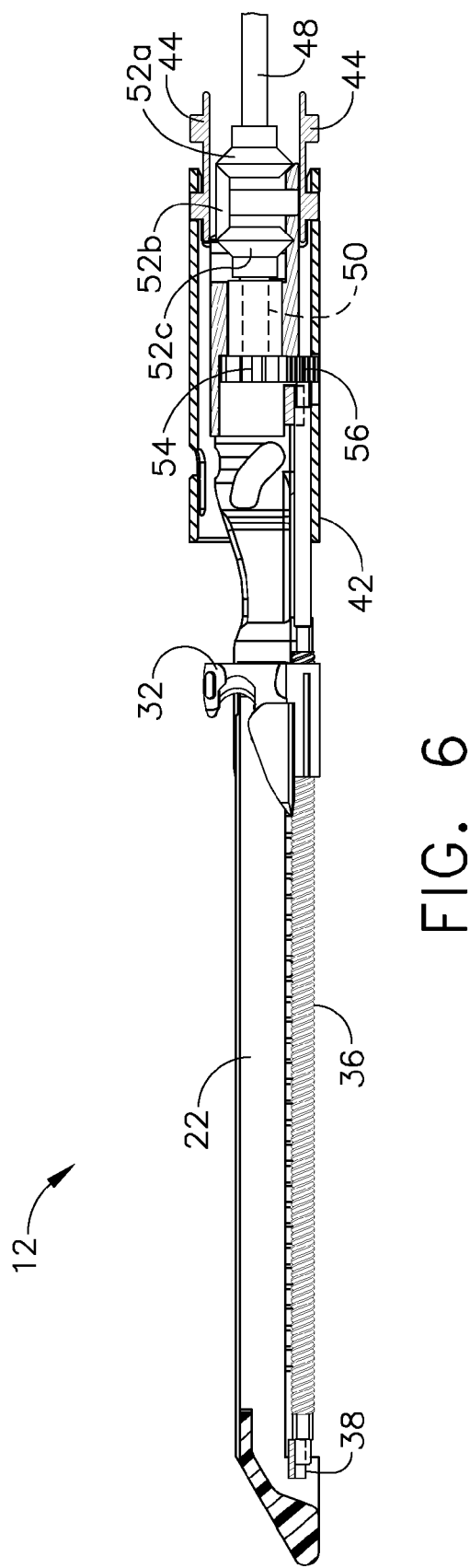
FIG. 6 is a side view of the end effector according to various embodiments of the present application.
Figure 7:
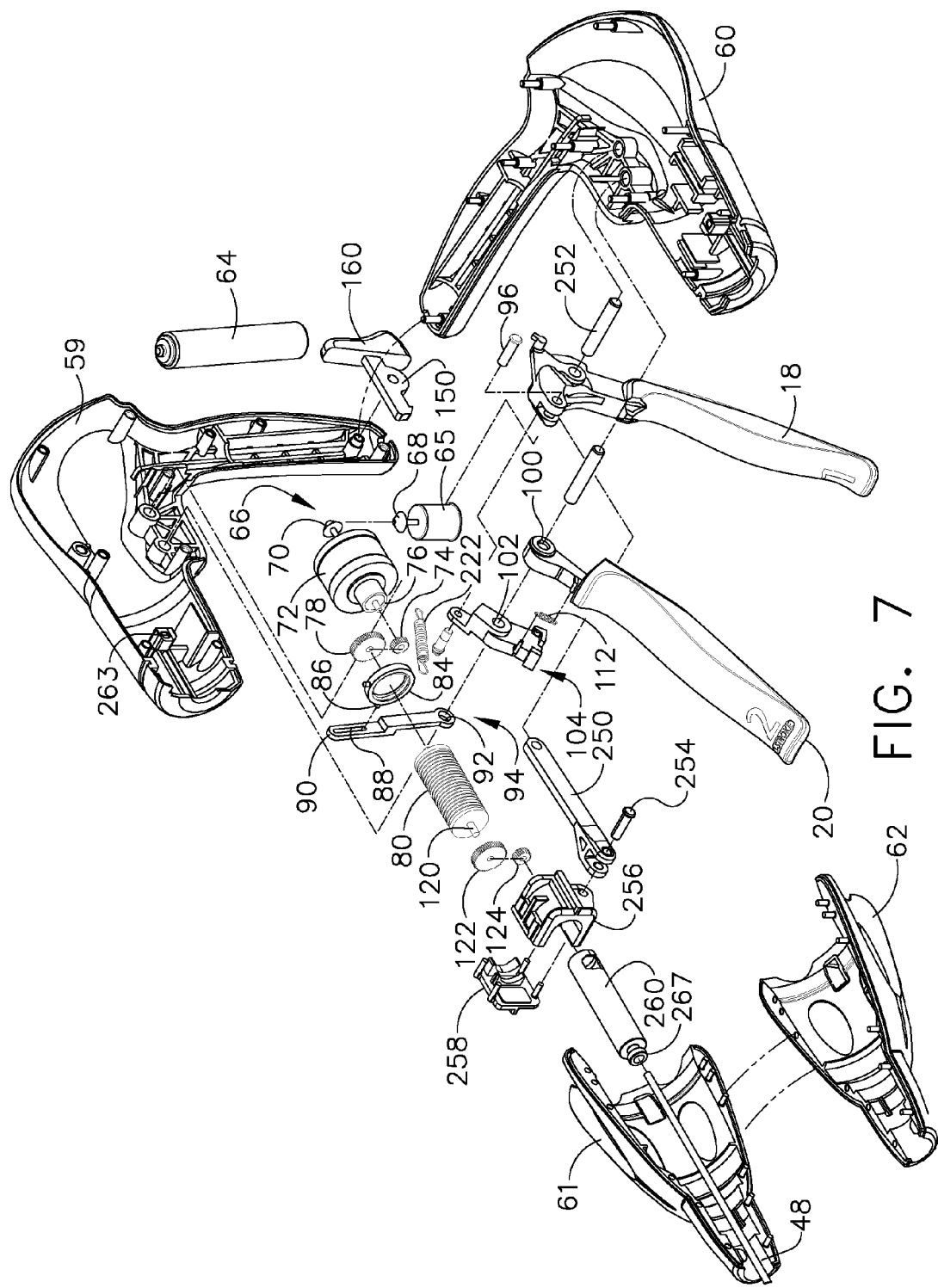
FIG. 7 is an exploded view of the handle of the instrument according to various embodiments of the present application.

FIGS. 4 and 5 are exploded views and FIG. 6 is a side view of the end effector 12 and shaft 8 according to various embodiments. As shown in the illustrated embodiment, the shaft 8 may include a proximate closure tube 40 and a distal closure tube 42 pivotably linked by a pivot links 44. The distal closure tube 42 includes an opening 45 into which the tab 27 on the anvil 24 is inserted in order to open and close the anvil 24. Disposed inside the closure tubes 40, 42 may be a proximate spine tube 46. Disposed inside the proximate spine tube 46 may be a main rotational (or proximate) drive shaft 48 that communicates with a secondary (or distal) drive shaft 50 via a bevel gear assembly 52. The secondary drive shaft 50 is connected to a drive gear 54 that engages a proximate drive gear 56 of the helical screw shaft 36. The vertical bevel gear 52b may sit and pivot in an opening 57 in the distal end of the proximate spine tube 46. A distal spine tube 58 may be used to enclose the secondary drive shaft 50 and the drive gears 54, 56. Collectively, the main drive shaft 48, the secondary drive shaft 50, and the articulation assembly (e.g., the bevel gear assembly 52a-c), are sometimes referred to herein as the "main drive shaft assembly." The closure tubes 40, 42 may be made of electrically conductive material (such as metal) so that they may serve as part of the antenna, as described further below. Components of the main drive shaft assembly (e.g., the drive shafts 48, 50) may be made of a nonconductive material (such as plastic).

A bearing 38, positioned at a distal end of the staple channel 22, receives the helical drive screw 36, allowing the helical drive screw 36 to freely rotate with respect to the channel 22. The helical screw shaft 36 may interface a threaded opening (not shown) of the knife 32 such that rotation of the shaft 36 causes the knife 32 to translate distally or proximately (depending on the direction of the rotation) through the staple channel 22. Accordingly, when the main drive shaft 48 is caused to rotate by actuation of the firing trigger 20 (as explained in more detail below), the bevel gear assembly 52a-c causes the secondary drive shaft 50 to rotate, which in turn, because of the engagement of the drive gears 54, 56, causes the helical screw shaft 36 to rotate, which causes the knife 32 to travel longitudinally along the channel 22 to cut any tissue clamped within the end effector. The sled 33 may be made of, for example, plastic, and may have a sloped distal surface. As the sled 33 traverses the channel 22, the sloped forward surface may push up or drive the staples in the staple cartridge 34 through the clamped tissue and against the anvil 24. The anvil 24 turns the staples, thereby stapling the severed tissue. When the knife 32 is retracted, the knife 32 and sled 33 may become disengaged, thereby leaving the sled 33 at the distal end of the channel 22.

According to various embodiments, as shown FIGS. 7-10, the surgical instrument may include a battery 64 in the handle 6. The illustrated embodiment provides user-feedback regarding the deployment and loading force of the cutting instrument in the end effector 12. In addition, the embodiment may use power provided by the user in retracting the firing trigger 18 to power the instrument 10 (a so-called "power assist" mode). As shown in the illustrated embodiment, the handle 6 includes exterior lower side pieces 59, 60 and exterior upper side pieces 61, 62 that fit together to form, in general, the exterior of the handle 6. The handle pieces 59-62 may be made of an electrically nonconductive material, such as plastic. A battery 64 may be provided in the pistol grip portion 26 of the handle 6. The battery 64 powers a motor 65 disposed in an upper portion of the pistol grip portion 26 of the handle 6. The battery 64 may be constructed according to any suitable construction or chemistry including, for example, a Li-ion chemistry such as $LiCoO_2$ or $LiNiO_2$, a Nickel Metal Hydride chemistry, etc. According to various embodiments, the motor 65 may be a DC brushed driving motor having a maximum rotation of, approximately, 5000 RPM to 100,000 RPM. The motor 64 may drive a 90° bevel gear assembly 66 comprising a first bevel gear 68 and a second bevel gear 70. The bevel gear assembly 66 may drive a planetary gear assembly 72. The planetary gear assembly 72 may include a pinion gear 74 connected to a drive shaft 76. The pinion gear 74 may drive a mating ring gear 78 that drives a helical gear drum 80 via a drive shaft 82. A ring 84 may be threaded on the helical gear drum 80. Thus, when the motor 65 rotates, the ring 84 is caused to travel along the helical gear drum 80 by means of the interposed bevel gear assembly 66, planetary gear assembly 72 and ring gear 78.

The handle 6 may also include a run motor sensor 110 in communication with the firing trigger 20 to detect when the firing trigger 20 has been drawn in (or "closed") toward the pistol grip portion 26 of the handle 6 by the operator to thereby actuate the cutting/stapling operation by the end effector 12. The sensor 110 may be a proportional sensor such as, for example, a rheostat or variable resistor. When the firing trigger 20 is drawn in, the sensor 110 detects the movement, and sends an electrical signal indicative of the voltage (or power) to be supplied to the motor 65. When the sensor 110 is a variable resistor or the like, the rotation of the motor 65 may be generally proportional to the amount of movement of the firing trigger 20. That is, if the operator only draws or closes the firing trigger 20 in a little bit, the rotation of the motor 65 is relatively low. When the firing trigger 20 is fully drawn in (or in the fully closed position), the rotation of the motor 65 is at its maximum. In other words, the harder the user pulls on the firing trigger 20, the more voltage is applied to the motor 65, causing greater rates of rotation. In another embodiment, for example, the control unit (described further below) may output a PWM control signal to the motor 65 based on the input from the sensor 110 in order to control the motor 65.

The handle 6 may include a middle handle piece 104 adjacent to the upper portion of the firing trigger 20. The handle 6 also may comprise a bias spring 112 connected between posts on the middle handle piece 104 and the firing trigger 20. The bias spring 112 may bias the firing trigger 20 to its fully open position. In that way, when the operator releases the firing trigger 20, the bias spring 112 will pull the firing trigger 20 to its open position, thereby removing actuation of the sensor 110, thereby stopping rotation of the motor 65. Moreover, by virtue of the bias spring 112, any time a user closes the firing trigger 20, the user will experience resistance to the closing operation, thereby providing the user with feedback as to the amount of rotation exerted by the motor 65. Further, the operator could stop retracting the firing trigger 20 to thereby remove force from the sensor 100, to thereby stop the motor 65. As such, the user may stop the deployment of the end effector 12, thereby providing a measure of control of the cutting/fastening operation to the operator.

The distal end of the helical gear drum 80 includes a distal drive shaft 120 that drives a ring gear 122, which mates with a pinion gear 124. The pinion gear 124 is connected to the main drive shaft 48 of the main drive shaft assembly. In that way, rotation of the motor 65 causes the main drive shaft assembly to rotate, which causes actuation of the end effector 12, as described above.

The ring 84 threaded on the helical gear drum 80 may include a post 86 that is disposed within a slot 88 of a slotted arm 90. The slotted arm 90 has an opening 92 at its opposite end 94 that receives a pivot pin 96 that is connected between the handle exterior side pieces 59, 60. The pivot pin 96 is also disposed through an opening 100 in the firing trigger 20 and an opening 102 in the middle handle piece 104.

In addition, the handle 6 may include a reverse motor (or end-of-stroke sensor) 130 and a stop motor (or beginning-of-stroke) sensor 142. In various embodiments, the reverse motor sensor 130 may be a limit switch located at the distal end of the helical gear drum 80 such that the ring 84 threaded on the helical gear drum 80 contacts and trips the reverse motor sensor 130 when the ring 84 reaches the distal end of the helical gear drum 80. The reverse motor sensor 130, when activated, sends a signal to the control unit which sends a signal to the motor 65 to reverse its rotation direction, thereby withdrawing the knife 32 of the end effector 12 following the cutting operation.

The stop motor sensor 142 may be, for example, a normally-closed limit switch. In various embodiments, it may be located at the proximate end of the helical gear drum 80 so that the ring 84 trips the switch 142 when the ring 84 reaches the proximate end of the helical gear drum 80.

In operation, when an operator of the instrument 10 pulls back the firing trigger 20, the sensor 110 detects the deployment of the firing trigger 20 and sends a signal to the control unit which sends a signal to the motor 65 to cause forward rotation of the motor 65 at, for example, a rate proportional to how hard the operator pulls back the firing trigger 20. The forward rotation of the motor 65 in turn causes the ring gear 78 at the distal end of the planetary gear assembly 72 to rotate, thereby causing the helical gear drum 80 to rotate, causing the ring 84 threaded on the helical gear drum 80 to travel distally along the helical gear drum 80. The rotation of the helical gear drum 80 also drives the main drive shaft assembly as described above, which in turn causes deployment of the knife 32 in the end effector 12. That is, the knife 32 and sled 33 are caused to traverse the channel 22 longitudinally, thereby cutting tissue clamped in the end effector 12. Also, the stapling operation of the end effector 12 is caused to happen in embodiments where a stapling-type end effector is used.

By the time the cutting/stapling operation of the end effector 12 is complete, the ring 84 on the helical gear drum 80 will have reached the distal end of the helical gear drum 80, thereby causing the reverse motor sensor 130 to be tripped, which sends a signal to the control unit which sends a signal to the motor 65 to cause the motor 65 to reverse its rotation. This in turn causes the knife 32 to retract, and also causes the ring 84 on the helical gear drum 80 to move back to the proximate end of the helical gear drum 80.

Figure 8:
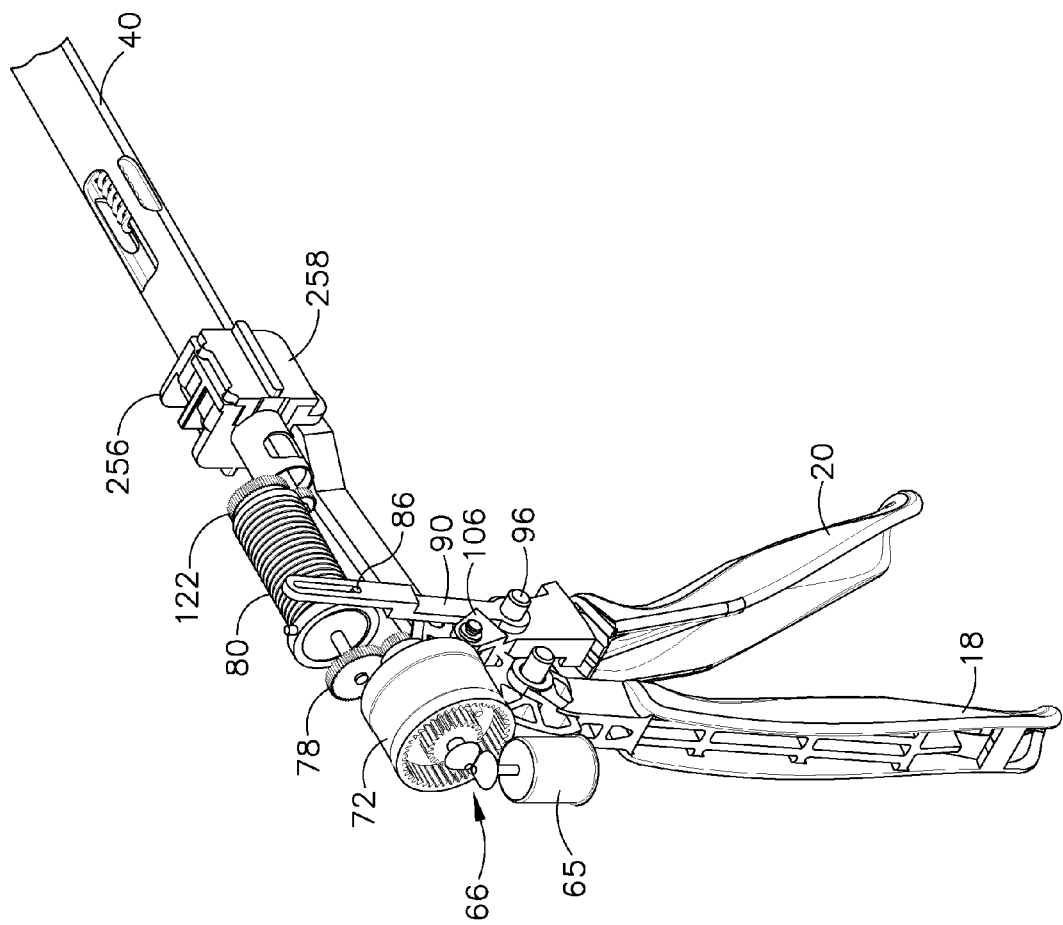
FIGS. 8 and 9 are partial perspective views of the handle according to various embodiments of the present application.
Figure 9:
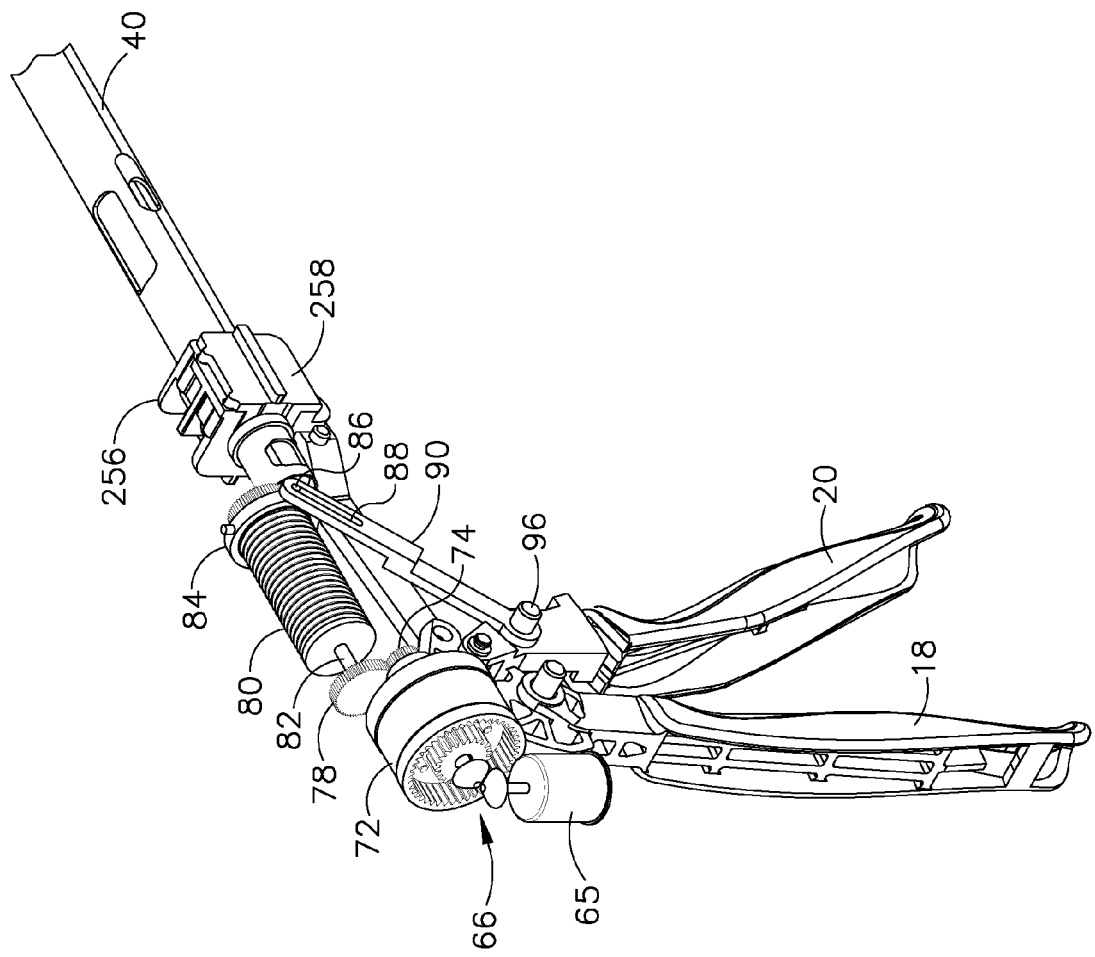
Figure 10:
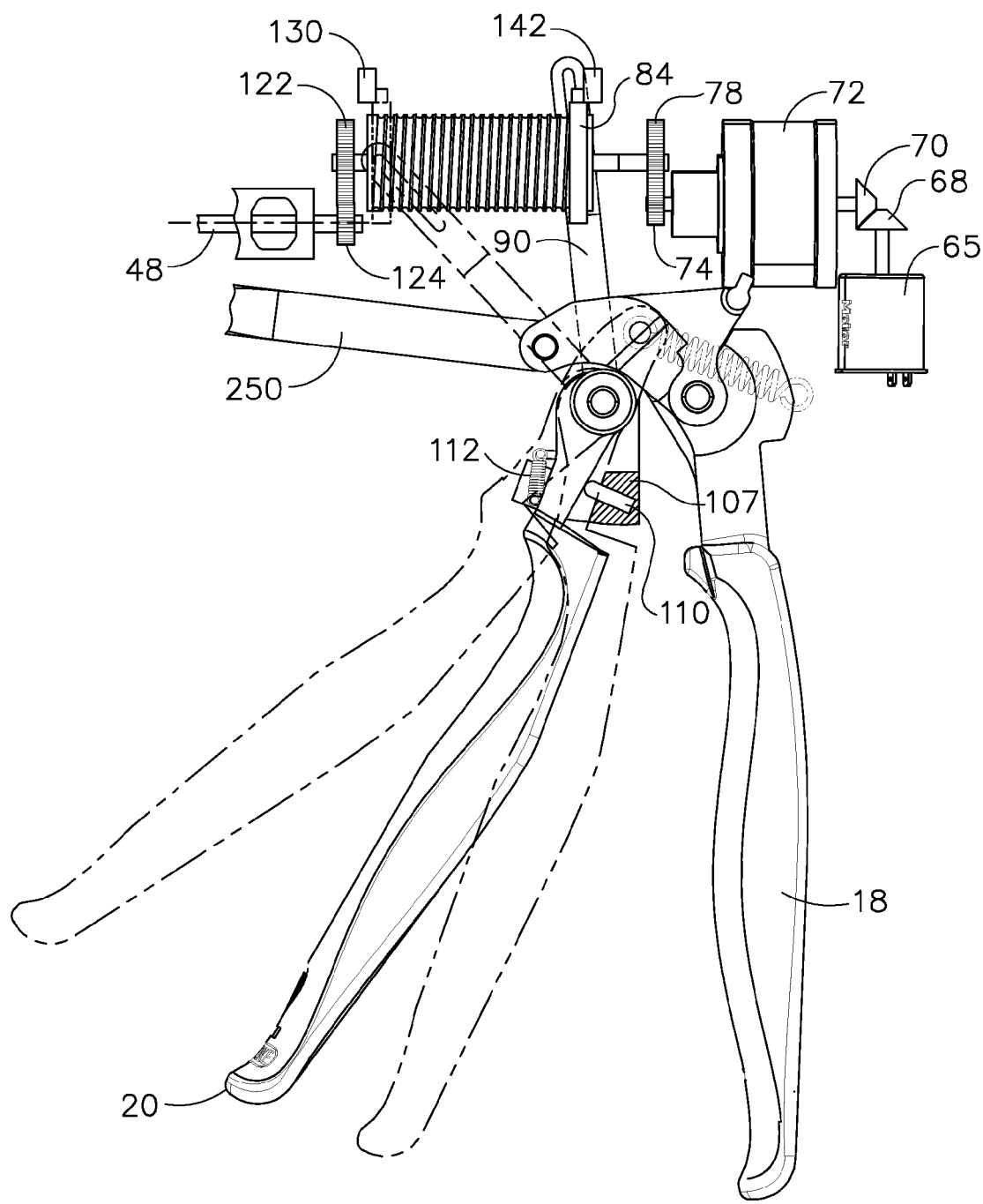
FIG. 10 is a side view of the handle according to various embodiments of the present application.

The middle handle piece 104 includes a backside shoulder 106 that engages the slotted arm 90 as best shown in FIGS. 8 and 9. The middle handle piece 104 also has a forward motion stop 107 that engages the firing trigger 20. The movement of the slotted arm 90 is controlled, as explained above, by rotation of the motor 65. When the slotted arm 90 rotates CCW as the ring 84 travels from the proximate end of the helical gear drum 80 to the distal end, the middle handle piece 104 will be free to rotate CCW. Thus, as the user draws in the firing trigger 20, the firing trigger 20 will engage the forward motion stop 107 of the middle handle piece 104, causing the middle handle piece 104 to rotate CCW. Due to the backside shoulder 106 engaging the slotted arm 90, however, the middle handle piece 104 will only be able to rotate CCW as far as the slotted arm 90 permits. In that way, if the motor 65 should stop rotating for some reason, the slotted arm 90 will stop rotating, and the user will not be able to further draw in the firing trigger 20 because the middle handle piece 104 will not be free to rotate CCW due to the slotted arm 90.

Components of an exemplary closure system for closing (or clamping) the anvil 24 of the end effector 12 by retracting the closure trigger 18 are also shown in FIGS. 7-10. In the illustrated embodiment, the closure system includes a yoke 250 connected to the closure trigger 18 by a pin 251 that is inserted through aligned openings in both the closure trigger 18 and the yoke 250. A pivot pin 252, about which the closure trigger 18 pivots, is inserted through another opening in the closure trigger 18 which is offset from where the pin 251 is inserted through the closure trigger 18. Thus, retraction of the closure trigger 18 causes the upper part of the closure trigger 18, to which the yoke 250 is attached via the pin 251, to rotate CCW. The distal end of the yoke 250 is connected, via a pin 254, to a first closure bracket 256. The first closure bracket 256 connects to a second closure bracket 258. Collectively, the closure brackets 256, 258 define an opening in which the proximate end of the proximate closure tube 40 (see FIG. 4) is seated and held such that longitudinal movement of the closure brackets 256, 258 causes longitudinal motion by the proximate closure tube 40. The instrument 10 also includes a closure rod 260 disposed inside the proximate closure tube 40. The closure rod 260 may include a window 261 into which a post 263 on one of the handle exterior pieces, such as exterior lower side piece 59 in the illustrated embodiment, is disposed to fixedly connect the closure rod 260 to the handle 6. In that way, the proximate closure tube 40 is capable of moving longitudinally relative to the closure rod 260. The closure rod 260 may also include a distal collar 267 that fits into a cavity 269 in proximate spine tube 46 and is retained therein by a cap 271 (see FIG. 4).

In operation, when the yoke 250 rotates due to retraction of the closure trigger 18, the closure brackets 256, 258 cause the proximate closure tube 40 to move distally (i.e., away from the handle end of the instrument 10), which causes the distal closure tube 42 to move distally, which causes the anvil 24 to rotate about the pivot point 25 into the clamped or closed position. When the closure trigger 18 is unlocked from the locked position, the proximate closure tube 40 is caused to slide proximately, which causes the distal closure tube 42 to slide proximately, which, by virtue of the tab 27 being inserted in the window 45 of the distal closure tube 42, causes the anvil 24 to pivot about the pivot point 25 into the open or unclamped position. In that way, by retracting and locking the closure trigger 18, an operator may clamp tissue between the anvil 24 and channel 22, and may unclamp the tissue following the cutting/stapling operation by unlocking the closure trigger 18 from the locked position.

The control unit (described further below) may receive the outputs from end-of-stroke and beginning-of-stroke sensors 130, 142 and the run-motor sensor 110, and may control the motor 65 based on the inputs. For example, when an operator initially pulls the firing trigger 20 after locking the closure trigger 18, the run-motor sensor 110 is actuated. If the staple cartridge 34 is present in the end effector 12, a cartridge lockout sensor (not shown) may be closed, in which case the control unit may output a control signal to the motor 65 to cause the motor 65 to rotate in the forward direction. When the end effector 12 reaches the end of its stroke, the reverse motor sensor 130 will be activated. The control unit may receive this output from the reverse motor sensor 130 and cause the motor 65 to reverse its rotational direction. When the knife 32 is fully retracted, the stop motor sensor switch 142 is activated, causing the control unit to stop the motor 65.

In other embodiments, rather than a proportional-type sensor 110, an on-off type sensor could be used. In such embodiments, the rate of rotation of the motor 65 would not be proportional to the force applied by the operator. Rather, the motor 65 would generally rotate at a constant rate. But the operator would still experience force feedback because the firing trigger 20 is geared into the gear drive train.

Figure 11:
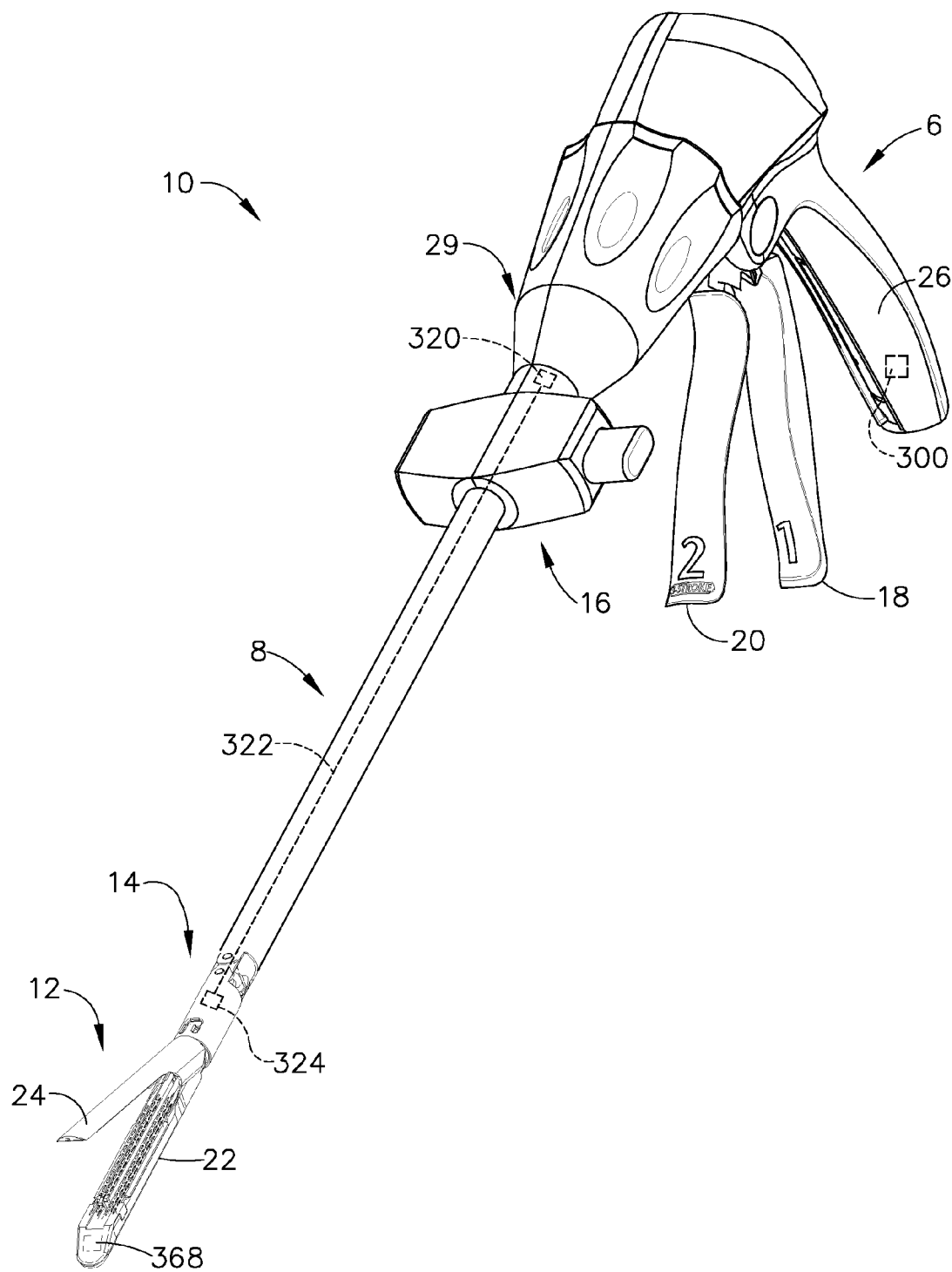

The instrument 10 may include a number of sensor transponders in the end effector 12 for sensing various conditions related to the end effector 12, such as sensor transponders for determining the status of the staple cartridge 34 (or other type of cartridge depending on the type of surgical instrument), the progress of the stapler during closure and firing, etc. The sensor transponders may be passively powered by inductive signals, as described further below, although in other embodiments the transponders could be powered by a remote power source, such as a battery in the end effector 12, for example. The sensor transponder(s) could include magnetoresistive, optical, electromechanical, RFID, MEMS, motion or pressure sensors, for example. These sensor transponders may be in communication with a control unit 300, which may be housed in the handle 6 of the instrument 10, for example, as shown in FIG. 11.

As shown in FIG. 12, according to various embodiments the control unit 300 may comprise a processor 306 and one or more memory units 308. By executing instruction code stored in the memory 308, the processor 306 may control various components of the instrument 10, such as the motor 65 or a user display (not shown), based on inputs received from the various end effector sensor transponders and other sensor(s) (such as the run-motor sensor 110, the end-of-stroke sensor 130, and the beginning-of-stroke sensor 142, for example). The control unit 300 may be powered by the battery 64 during surgical use of instrument 10. The control unit 300 may comprise an inductive element 302 (e.g., a coil or antenna) to pick up wireless signals from the sensor transponders, as described in more detail below. Input signals received by the inductive element 302 acting as a receiving antenna may be demodulated by a demodulator 310 and decoded by a decoder 312. The input signals may comprise data from the sensor transponders in the end effector 12, which the processor 306 may use to control various aspects of the instrument 10.

To transmit signals to the sensor transponders, the control unit 300 may comprise an encoder 316 for encoding the signals and a modulator 318 for modulating the signals according to the modulation scheme. The inductive element 302 may act as the transmitting antenna. The control unit 300 may communicate with the sensor transponders using any suitable wireless communication protocol and any suitable frequency (e.g., an ISM band). Also, the control unit 300 may transmit signals at a different frequency range than the frequency range of the received signals from the sensor transponders. Also, although only one antenna (inductive element 302) is shown in FIG. 12, in other embodiments the control unit 300 may have separate receiving and transmitting antennas.

According to various embodiments, the control unit 300 may comprise a microcontroller, a microprocessor, a field programmable gate array (FPGA), one or more other types of integrated circuits (e.g., RF receivers and PWM controllers), and/or discrete passive components. The control units may also be embodied as system-on-chip (SoC) or a system-in-package (SIP), for example.

As shown in FIG. 11, the control unit 300 may be housed in the handle 6 of the instrument 10 and one or more of the sensor transponders 368 for the instrument 10 may be located in the end effector 12. To deliver power and/or transmit data to or from the sensor transponders 368 in the end effector 12, the inductive element 302 of the control unit 300 may be inductively coupled to a secondary inductive element (e.g., a coil) 320 positioned in the shaft 8 distally from the rotation joint 29. The secondary inductive element 320 is preferably electrically insulated from the conductive shaft 8.

The secondary inductive element 320 may be connected by an electrically conductive, insulated wire 322 to a distal inductive element (e.g., a coil) 324 located near the end effector 12, and preferably distally relative to the articulation pivot 14. The wire 322 may be made of an electrically conductive polymer and/or metal (e.g., copper) and may be sufficiently flexible so that it could pass though the articulation pivot 14 and not be damaged by articulation. The distal inductive element 324 may be inductively coupled to the sensor transponder 368 in, for example, the cartridge 34 of the end effector 12. The transponder 368, as described in more detail below, may include an antenna (or coil) for inductive coupling to the distal coil 324, a sensor and integrated control electronics for receiving and transmitting wireless communication signals.

The transponder 368 may use a portion of the power of the inductive signal received from the distal inductive element 326 to passively power the transponder 368. Once sufficiently powered by the inductive signals, the transponder 368 may receive and transmit data to the control unit 300 in the handle 6 via (i) the inductive coupling between the transponder 368 and the distal inductive element 324, (ii) the wire 322, and (iii) the inductive coupling between the secondary inductive element 320 and the control unit 300. That way, the control unit 300 may communicate with the transponder 368 in the end effector 12 without a direct wired connection through complex mechanical joints like the rotating joint 29 and/or without a direct wired connection from the shaft 8 to the end effector 12, places where it may be difficult to maintain such a wired connection. In addition, because the distances between the inductive elements (e.g., the spacing between (i) the transponder 368 and the distal inductive element 324, and (ii) the secondary inductive element 320 and the control unit 300) and fixed and known, the couplings could be optimized for inductive transfer of energy. Also, the distances could be relatively short so that relatively low power signals could be used to thereby minimize interference with other systems in the use environment of the instrument 10.

Figure 13:
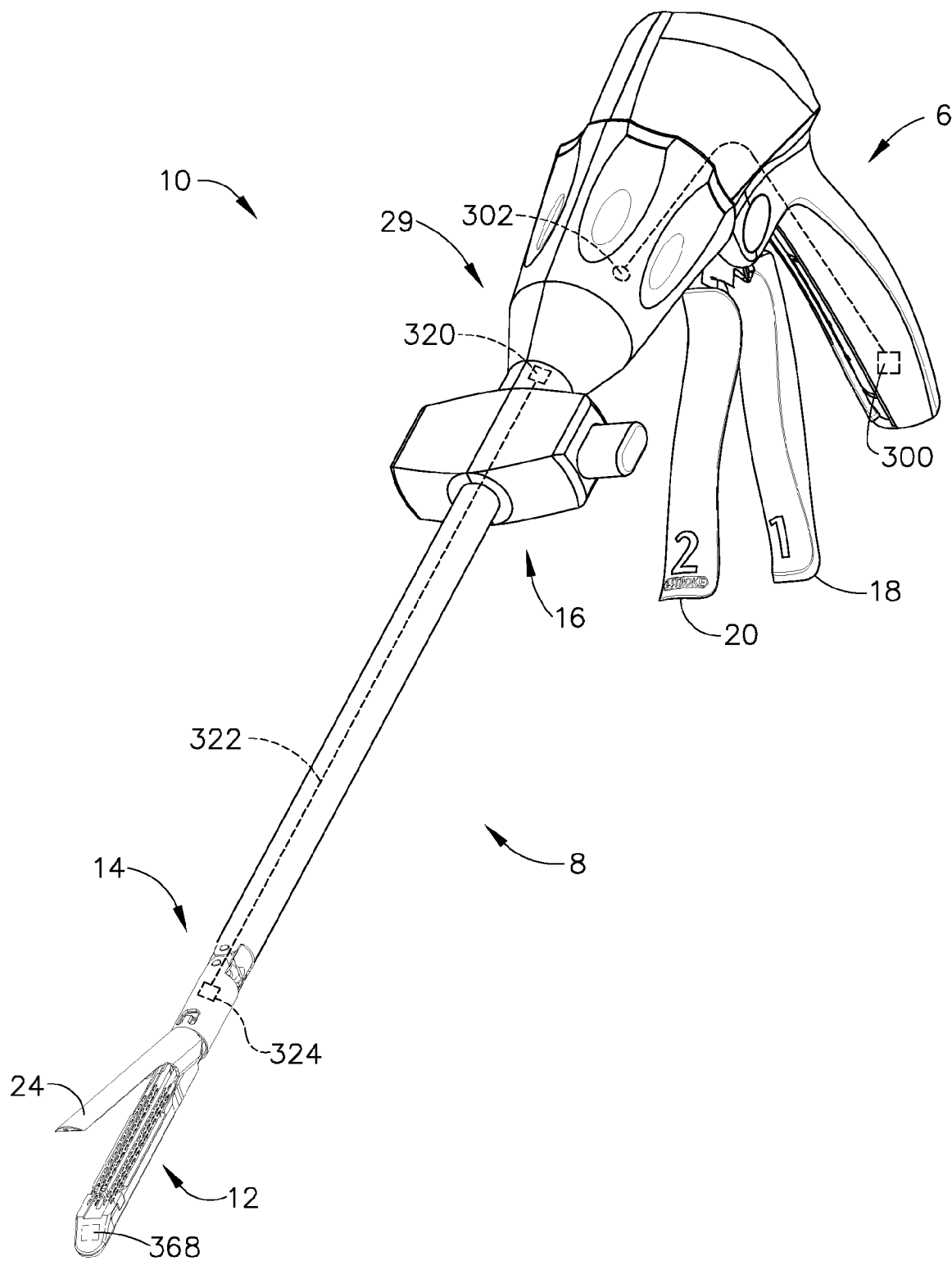

In the embodiment of FIG. 12, the inductive element 302 of the control unit 300 is located relatively near to the control unit 300. According to other embodiments, as shown in FIG. 13, the inductive element 302 of the control unit 300 may be positioned closer to the rotating joint 29 to that it is closer to the secondary inductive element 320, thereby reducing the distance of the inductive coupling in such an embodiment. Alternatively, the control unit 300 (and hence the inductive element 302) could be positioned closer to the secondary inductive element 320 to reduce the spacing.

Figure 14:
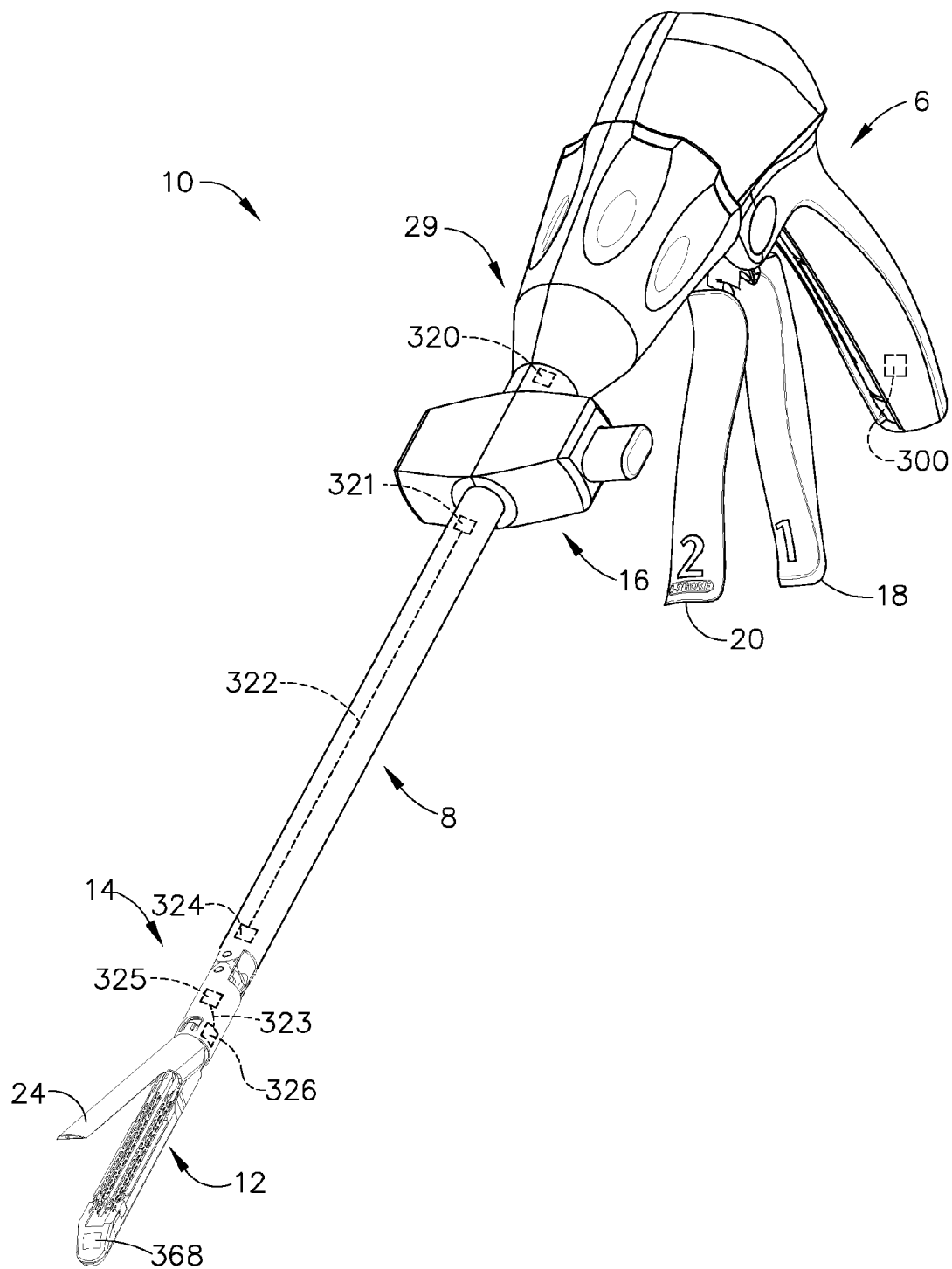

In other embodiments, more or fewer than two inductive couplings may be used. For example, in some embodiments, the surgical instrument 10 may use a single inductive coupling between the control unit 300 in the handle 6 and the transponder 368 in the end effector 12, thereby eliminating the inductive elements 320, 324 and the wire 322. Of course, in such an embodiment, a stronger signal may be required due to the greater distance between the control unit 300 in the handle 6 and the transponder 368 in the end effector 12. Also, more than two inductive couplings could be used. For example, if the surgical instrument 10 had numerous complex mechanical joints where it would be difficult to maintain a direct wired connection, inductive couplings could be used to span each such joint. For example, inductive couplers could be used on both sides of the rotary joint 29 and both sides of the articulation pivot 14, with the inductive element 321 on the distal side of the rotary joint 29 connected by a wire 322 to the inductive element 324 of the proximate side of the articulation pivot, and a wire 323 connecting the inductive elements 325, 326 on the distal side of the articulation pivot 14 as shown in FIG. 14. In this embodiment, the inductive element 326 may communicate with the sensor transponder 368.

In addition, the transponder 368 may include a number of different sensors. For example, it may include an array of sensors. Further, the end effector 12 could include a number of sensor transponders 368 in communication with the distal inductive element 324 (and hence the control unit 300). Also, the inductive elements 320, 324 may or may not include ferrite cores. As mentioned before, they are also preferably insulated from the electrically conductive outer shaft (or frame) of the instrument 10 (e.g., the closure tubes 40, 42), and the wire 322 is also preferably insulated from the outer shaft 8.

FIG. 15 is a diagram of an end effector 12 including a transponder 368 held or embedded in the cartridge 34 at the distal end of the channel 22. The transponder 368 may be connected to the cartridge 34 by a suitable bonding material, such as epoxy. In this embodiment, the transponder 368 includes a magnetoresistive sensor. The anvil 24 also includes a permanent magnet 369 at its distal end and generally facing the transponder 368. The end effector 12 also includes a permanent magnet 370 connected to the sled 33 in this example embodiment. This allows the transponder 368 to detect both opening/closing of the end effector 12 (due to the permanent magnet 369 moving further or closer to the transponder as the anvil 24 opens and closes) and completion of the stapling/cutting operation (due to the permanent magnet 370 moving toward the transponder 368 as the sled 33 traverses the channel 22 as part of the cutting operation).

FIG. 15 also shows the staples 380 and the staple drivers 382 of the staple cartridge 34. As explained previously, according to various embodiments, when the sled 33 traverses the channel 22, the sled 33 drives the staple drivers 382 which drive the staples 380 into the severed tissue held in the end effector 12, the staples 380 being formed against the anvil 24. As noted above, such a surgical cutting and fastening instrument is but one type of surgical instrument in which embodiments of the present application may be advantageously employed. Various embodiments of the present application may be used in any type of surgical instrument having one or more sensor transponders.

In the embodiments described above, the battery 64 powers (at least partially) the firing operation of the instrument 10. As such, the instrument may be a so-called "power-assist" device. More details and additional embodiments of power-assist devices are described in the '573 application, which is incorporated herein. It should be recognized, however, that the instrument 10 need not be a power-assist device and that this is merely an example of a type of device that may utilize aspects of embodiments of the present application. For example, the instrument 10 may include a user display (such as a LCD or LED display) that is powered by the battery 64 and controlled by the control unit 300. Data from the sensor transponders 368 in the end effector 12 may be displayed on such a display.

In another embodiment, the shaft 8 of the instrument 10, including for example, the proximate closure tube 40 and the distal closure tube 42, may collectively serve as part of an antenna for the control unit 300 by radiating signals to the sensor transponder 368 and receiving radiated signals from the sensor transponder 368. That way, signals to and from the remote sensor in the end effector 12 may be transmitted via the shaft 8 of the instrument 10.

The proximate closure tube 40 may be grounded at its proximate end by the exterior lower and upper side pieces 59-62, which may be made of a nonelectrically conductive material, such as plastic. The drive shaft assembly components (including the main drive shaft 48 and secondary drive shaft 50) inside the proximate and distal closure tubes 40, 42 may also be made of a nonelectrically conductive material, such as plastic. Further, components of end effector 12 (such as the anvil 24 and the channel 22) may be electrically coupled to (or in direct or indirect electrical contact with) the distal closure tube 42 such that they may also serve as part of the antenna. Further, the sensor transponder 368 could be positioned such that it is electrically insulated from the components of the shaft 8 and end effector 12 serving as the antenna. For example, the sensor transponder 368 may be positioned in the cartridge 34, which may be made of a nonelectrically conductive material, such as plastic. Because the distal end of the shaft 8 (such as the distal end of the distal closure tube 42) and the portions of the end effector 12 serving as the antenna may be relatively close in distance to the sensor 368, the power for the transmitted signals may be held at low levels, thereby minimizing or reducing interference with other systems in the use environment of the instrument 10.

Figure 16:
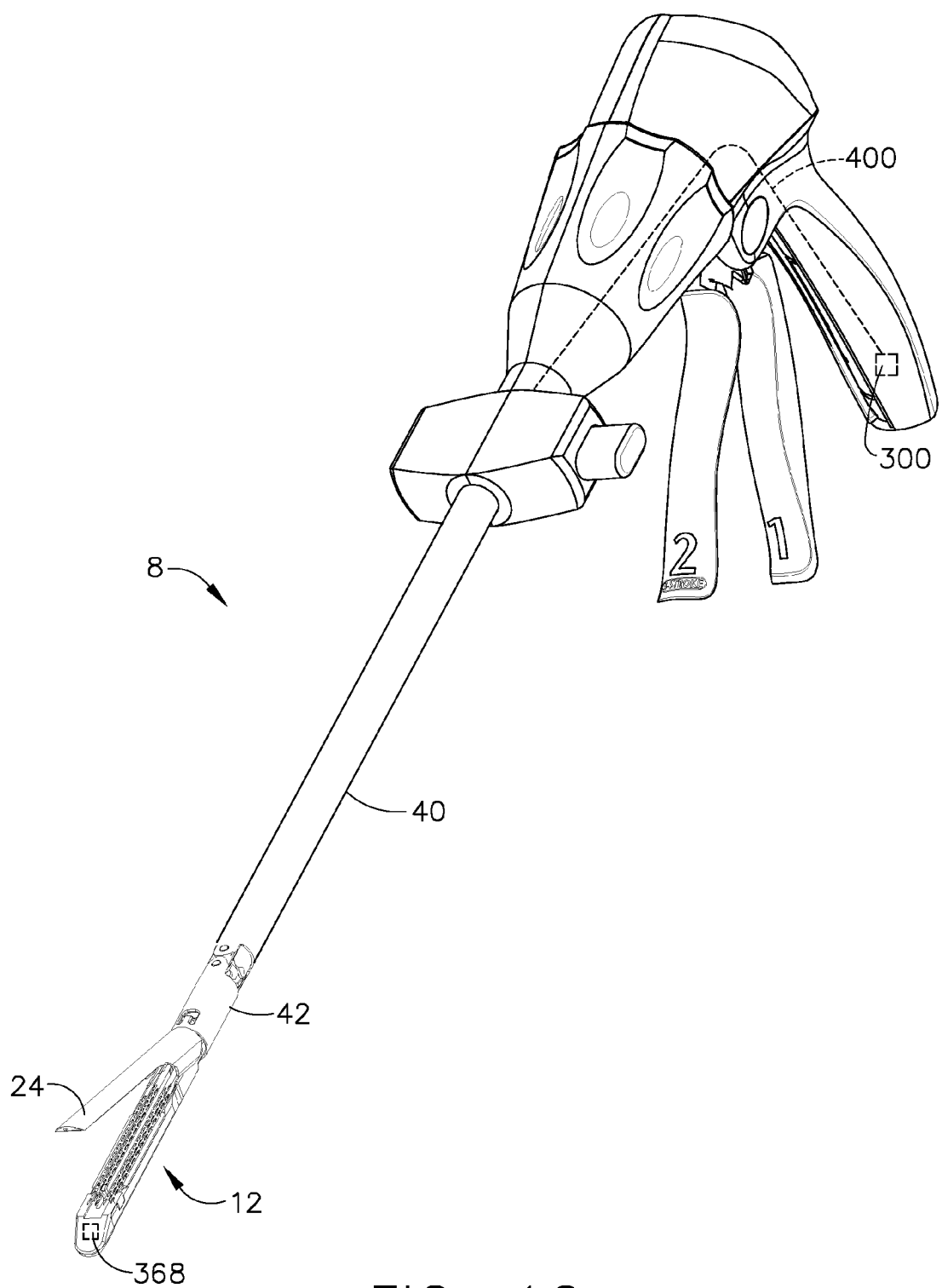

In such an embodiment, as shown in FIG. 16, the control unit 300 may be electrically coupled to the shaft 8 of the instrument 10, such as to the proximate closure tube 40, by a conductive link 400 (e.g., a wire). Portions of the outer shaft 8, such as the closure tubes 40, 42, may therefore act as part of an antenna for the control unit 300 by radiating signals to the sensor 368 and receiving radiated signals from the sensor 368. Input signals received by the control unit 300 may be demodulated by the demodulator 310 and decoded by the decoder 312 (see FIG. 12). The input signals may comprise data from the sensors 368 in the end effector 12, which the processor 306 may use to control various aspects of the instrument 10, such as the motor 65 or a user display.

To transmit data signals to or from the sensors 368 in the end effector 12, the link 400 may connect the control unit 300 to components of the shaft 8 of the instrument 10, such as the proximate closure tube 40, which may be electrically connected to the distal closure tube 42. The distal closure tube 42 is preferably electrically insulated from the remote sensor 368, which may be positioned in the plastic cartridge 34 (see FIG. 3). As mentioned before, components of the end effector 12, such as the channel 22 and the anvil 24 (see FIG. 3), may be conductive and in electrical contact with the distal closure tube 42 such that they, too, may serve as part of the antenna.

With the shaft 8 acting as the antenna for the control unit 300, the control unit 300 can communicate with the sensor 368 in the end effector 12 without a direct wired connection. In addition, because the distances between shaft 8 and the remote sensor 368 is fixed and known, the power levels could be optimized for low levels to thereby minimize interference with other systems in the use environment of the instrument 10. The sensor 368 may include communication circuitry for radiating signals to the control unit 300 and for receiving signals from the control unit 300, as described above. The communication circuitry may be integrated with the sensor 368.

In another embodiment, the components of the shaft 8 and/or the end effector 12 may serve as an antenna for the remote sensor 368. In such an embodiment, the remote sensor 368 is electrically connected to the shaft (such as to distal closure tube 42, which may be electrically connected to the proximate closure tube 40) and the control unit 300 is insulated from the shaft 8. For example, the sensor 368 could be connected to a conductive component of the end effector 12 (such as the channel 22), which in turn may be connected to conductive components of the shaft (e.g., the closure tubes 40, 42). Alternatively, the end effector 12 may include a wire (not shown) that connects the remote sensor 368 the distal closure tube 42.

Typically, surgical instruments, such as the instrument 10, are cleaned and sterilized prior to use. In one sterilization technique, the instrument 10 is placed in a closed and sealed container 280, such as a plastic or TYVEK container or bag, as shown in FIGS. 17 and 18. The container and the instrument are then placed in a field of radiation that can penetrate the container, such as gamma radiation, x-rays, or high-energy electrons. The radiation kills bacteria on the instrument 10 and in the container 280. The sterilized instrument 10 can then be stored in the sterile container 280. The sealed, sterile container 280 keeps the instrument 10 sterile until it is opened in a medical facility or some other use environment. Instead of radiation, other means of sterilizing the instrument 10 may be used, such as ethylene oxide or steam.

When radiation, such as gamma radiation, is used to sterilize the instrument 10, components of the control unit 300, particularly the memory 308 and the processor 306, may be damaged and become unstable. Thus, according to various embodiments of the present application, the control unit 300 may be programmed after packaging and sterilization of the instrument 10.

As shown in FIG. 17, a remote programming device 320, which may be a handheld device, may be brought into wireless communication with the control unit 300. The remote programming device 320 may emit wireless signals that are received by the control unit 300 to program the control unit 300 and to power the control unit 300 during the programming operation. That way, the battery 64 does not need to power the control unit 300 during the programming operation. According to various embodiments, the programming code downloaded to the control unit 300 could be of relatively small size, such as 1 MB or less, so that a communications protocol with a relatively low data transmission rate could be used if desired. Also, the remote programming unit 320 could be brought into close physical proximity with the surgical instrument 10 so that a low power signal could be used.

Referring back to FIG. 19, the control unit 300 may comprise an inductive coil 402 to pick up wireless signals from a remote programming device 320. A portion of the received signal may be used by a power circuit 404 to power the control unit 300 when it is not being powered by the battery 64.

Input signals received by the coil 402 acting as a receiving antenna may be demodulated by a demodulator 410 and decoded by a decoder 412. The input signals may comprise programming instructions (e.g., code), which may be stored in a non-volatile memory portion of the memory 308. The processor 306 may execute the code when the instrument 10 is in operation. For example, the code may cause the processor 306 to output control signals to various sub-systems of the instrument 10, such as the motor 65, based on data received from the sensors 368.

The control unit 300 may also comprise a non-volatile memory unit 414 that comprises boot sequence code for execution by the processor 306. When the control unit 300 receives enough power from the signals from the remote control unit 320 during the post-sterilization programming operation, the processor 306 may first execute the boot sequence code ("boot loader") 414, which may load the processor 306 with an operating system.

The control unit 300 may also send signals back to the remote programming unit 320, such as acknowledgement and handshake signals, for example. The control unit 300 may comprise an encoder 416 for encoding the signals to then be sent to the programming device 320 and a modulator 418 for modulating the signals according to the modulation scheme. The coil 402 may act as the transmitting antenna. The control unit 300 and the remote programming device 320 may communicate using any suitable wireless communication protocol (e.g., Bluetooth) and any suitable frequency (e.g., an ISM band). Also, the control unit 300 may transmit signals at a different frequency range than the frequency range of the received signals from the remote programming unit 320.

FIG. 20 is a simplified diagram of the remote programming device 320 according to various embodiments of the present application. As shown in FIG. 20, the remote programming unit 320 may comprise a main control board 230 and a boosted antenna board 232. The main control board 230 may comprise a controller 234, a power module 236, and a memory 238. The memory 238 may stored the operating instructions for the controller 234 as well as the programming instructions to be transmitted to the control unit 300 of the surgical instrument 10. The power module 236 may provide a stable DC voltage for the components of the remote programming device 320 from an internal battery (not shown) or an external AC or DC power source (not shown).

The boosted antenna board 232 may comprise a coupler circuit 240 that is in communication with the controller 234 via an I²C bus, for example. The coupler circuit 240 may communicate with the control unit 300 of the surgical instrument via an antenna 244. The coupler circuit 240 may handle the modulating/demodulating and encoding/decoding operations for transmissions with the control unit. According to other embodiments, the remote programming device 320 could have a discrete modulator, demodulator, encoder and decoder. As shown in FIG. 20, the boost antenna board 232 may also comprise a transmitting power amp 246, a matching circuit 248 for the antenna 244, and a filter/amplifier 249 for receiving signals.

According to other embodiments, as shown in FIG. 20, the remote programming device could be in communication with a computer device 460, such as a PC or a laptop, via a USB and/or RS232 interface, for example. In such a configuration, a memory of the computing device 460 may store the programming instructions to be transmitted to the control unit 300. In another embodiment, the computing device 460 could be configured with a wireless transmission system to transmit the programming instructions to the control unit 300.

In addition, according to other embodiments, rather than using inductive coupling between the control unit 300 and the remote programming device 320, capacitively coupling could be used. In such an embodiment, the control unit 300 could have a plate instead of a coil, as could the remote programming unit 320.

Figure 22:
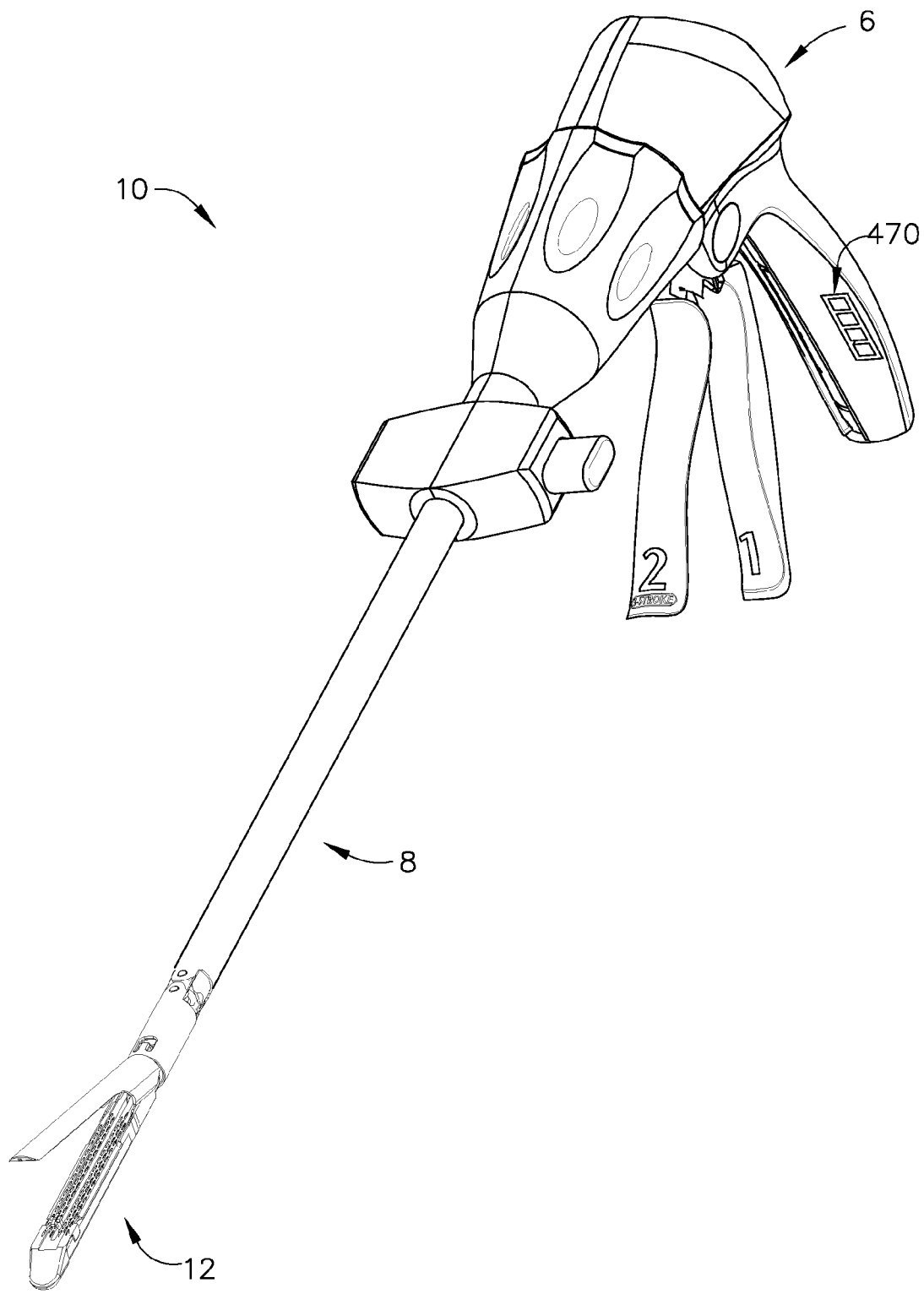

In another embodiment, rather than using a wireless communication link between the control unit 300 and the remote programming device 320, the programming device 320 may be physically connected to the control unit 300 while the instrument 10 is in its sterile container 280 in such a way that the instrument 10 remains sterilized. FIG. 21 is a diagram of a packaged instrument 10 according to such an embodiment. As shown in FIG. 22, the handle 6 of the instrument 10 may include an external connection interface 470. The container 280 may further comprise a connection interface 472 that mates with the external connection interface 470 of the instrument 10 when the instrument 10 is packaged in the container 280. The programming device 320 may include an external connection interface (not shown) that may connect to the connection interface 472 at the exterior of the container 280 to thereby provide a wired connection between the programming device 320 and the external connection interface 470 of the instrument 10.

FIGS. 23 and 24 depict a surgical cutting and fastening instrument 510 according to various embodiments of the present application. The illustrated embodiment is an endoscopic instrument and, in general, the embodiments of the instrument 510 described herein are endoscopic surgical cutting and fastening instruments. It should be noted, however, that according to other embodiments of the present application, the instrument may be a non-endoscopic surgical cutting and fastening instrument, such as a laparoscopic instrument.

The surgical instrument 510 depicted in FIGS. 23 and 24 comprises a handle 512, a shaft 514, and an articulating end effector 516 pivotally connected to the shaft 514 at an articulation pivot 518. An articulation control 520 may be provided adjacent to the handle 512 to effect rotation of the end effector 516 about the articulation pivot 518. In the illustrated embodiment, the end effector 516 is configured to act as an endocutter for clamping, severing and stapling tissue, although, in other embodiments, different types of end effectors may be used, such as end effectors for other types of surgical devices, such as graspers, cutters, staplers, clip appliers, access devices, drug/gene therapy devices, ultrasound, RF or laser devices, etc.

The handle 512 of the instrument 510 may include a closure trigger 522 and a firing trigger 524 for actuating the end effector 516. It will be appreciated that instruments having end effectors directed to different surgical tasks may have different numbers or types of triggers or other suitable controls for operating the end effector 516. The end effector 516 is shown separated from the handle 512 by a preferably elongate shaft 514. In one embodiment, an operator of the instrument 510 may articulate the end effector 516 relative to the shaft 514 by utilizing the articulation control 520 as described in more detail in pending U.S. patent application Ser. No. 11/329,020 entitled "SURGICAL INSTRUMENT HAVING AN ARTICULATING END EFFECTOR" to Hueil et al., which is incorporated herein by reference.

The end effector 516 includes in this example, among other things, a staple channel 526 and a pivotally translatable clamping member, such as an anvil 528, which are maintained at a spacing that assures effective stapling and severing of tissue clamped in the end effector 516. The handle 512 includes a pistol grip 530 towards which a closure trigger 522 is pivotally drawn by the operator to cause clamping or closing of the anvil 528 toward the staple channel 526 of the end effector 516 to thereby clamp tissue positioned between the anvil 528 and the channel 526. The firing trigger 524 is farther outboard of the closure trigger 522. Once the closure trigger 522 is locked in the closure position as further described below, the firing trigger 524 may rotate slightly toward the pistol grip 530 so that it can be reached by the operator using one hand. The operator may then pivotally draw the firing trigger 524 toward the pistol grip 530 to cause the stapling and severing of clamped tissue in the end effector 516. In other embodiments, different types of clamping members besides the anvil 528 may be used, such as, for example, an opposing jaw, etc.

It will be appreciated that the terms "proximal" and "distal" are used herein with reference to a operator gripping the handle 512 of an instrument 510. Thus, the end effector 516 is distal with respect to the more proximal handle 512. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

The closure trigger 522 may be actuated first. Once the operator is satisfied with the positioning of the end effector 516, the operator may draw back the closure trigger 522 to its fully closed, locked position proximate to the pistol grip 530. The firing trigger 524 may then be actuated. The firing trigger 524 returns to the open position (shown in FIGS. 23 and 24) when the operator removes pressure, as described more fully below. A release button 532 on the handle 512, when depressed, may release the locked closure trigger 522. Various configurations for locking and unlocking the closure trigger 522 using the release button 532 are described in pending U.S. patent application Ser. No. 11/343,573 entitled "MOTOR-DRIVEN SURGICAL CUTTING AND FASTENING INSTRUMENT WITH LOADING FORCE FEEDBACK" to Shelton, I V et al., which is incorporated herein by reference.

FIG. 25A is an exploded view of the end effector 516 according to various embodiments. As shown in the illustrated embodiment, the end effector 516 may include, in addition to the previously-mentioned channel 526 and anvil 528, a cutting instrument 534, a sled 536, a staple cartridge 538 that is removably seated (e.g., installed) in the channel 526, and a helical screw shaft 540. FIG. 25B is a perspective view of the cutting instrument 534 of FIG. 25A.

The anvil 528 may be pivotably opened and closed at a pivot point 542 connected to the proximate end of the channel 526. The anvil 528 may also include a tab 544 at its proximate end that is inserted into a component of the mechanical closure system (described further below) to open and close the anvil 528. When the closure trigger 522 is actuated, that is, drawn in by an operator of the instrument 510, the anvil 528 may pivot about the pivot point 542 into the clamped or closed position. If clamping of the end effector 516 is satisfactory, the operator may actuate the firing trigger 524, which, as explained in more detail below, causes the cutting instrument 534 to travel longitudinally along the channel 526.

As shown, the cutting instrument 534 includes upper guide pins 546 that enter an anvil slot 548 in the anvil 528 to verify and assist in maintaining the anvil 528 in a closed state during staple formation and severing. Spacing between the channel 526 and anvil 528 is further maintained by the cutting instrument 534 by having middle pins 550 slide along the top surface of the channel 526 while a bottom foot 552 opposingly slides along the undersurface of the channel 526, guided by a longitudinal opening 554 in the channel 526. A distally presented cutting surface 556 between the upper guide pins 546 and middle pins 550 severs clamped tissue while distally-presented surface 558 actuates the staple cartridge 538 by progressively driving the sled 536 from an unfired position to a fired position. Actuation of the staple cartridge 538 causes staple drivers 560 to cam upwardly, driving staples 562 out of upwardly open staple holes 564 formed in the staple cartridge 538. The staples 562 are subsequently formed against a staple forming undersurface 66 of the anvil 528. A staple cartridge tray 568 encompasses from the bottom the other components of the staple cartridge 538 to hold them in place. The staple cartridge tray 568 includes a rearwardly open slot 570 that overlies the longitudinal opening 554 in the channel 526. A lower surface of the staple cartridge 538 and an upward surface of the channel 526 form a firing drive slot 700 (FIG. 28) through which the middle pins 550 pass during distal and proximal movement of the cutting instrument 534. The sled 536 may be an integral component of the staple cartridge 538 such that when the cutting instrument 534 retracts following the cutting operation, the sled 536 does not retract. U.S. Pat. No. 6,978,921, entitled "SURGICAL STAPLING INSTRUMENT INCORPORATING AN E-BEAM FIRING MECHANISM" to Shelton, I V et al., which is incorporated herein by reference, provides more details about such two-stroke cutting and fastening instruments.

It should be noted that although the embodiments of the instrument 510 described herein employ an end effector 516 that staples the severed tissue, in other embodiments different techniques for fastening or sealing the severed tissue may be used. For example, end effectors that use RF energy or adhesives to fasten the severed tissue may also be used. U.S. Pat. No. 5,709,680 entitled "ELECTROSURGICAL HEMOSTATIC DEVICE" to Yates et al., and U.S. Pat. No. 5,688,270 entitled "ELECTOSURGICAL HEMOSTATIC DEVICE WITH RECESSED AND/OR OFFSET ELECTRODES" to Yates et al., both of which are incorporated herein by reference, disclose cutting instruments that uses RF energy to fasten the severed tissue. U.S. patent application Ser. No. 11/267,811 entitled "SURGICAL STAPLING INSTRUMENTS STRUCTURED FOR DELIVERY OF MEDICAL AGENTS" to Morgan et al., and U.S. patent application Ser. No. 11/267,383 entitled "SURGICAL STAPLING INSTRUMENTS STRUCTURED FOR PUMP-ASSISTED DELIVERY OF MEDICAL AGENTS" to Shelton I V et al., both of which are also incorporated herein by reference, disclose cutting instruments that uses adhesives to fasten the severed tissue. Accordingly, although the description herein refers to cutting/stapling operations and the like, it should be recognized that this is an exemplary embodiment and is not meant to be limiting. Other tissue-fastening techniques may also be used.

FIGS. 26 and 27 are exploded views and FIG. 28 is a side view of the end effector 516 and shaft 514 according to various embodiments. As shown in the illustrated embodiment, the shaft 514 may include a proximate closure tube 572 and a distal closure tube 574 pivotably linked by a pivot links 576. The distal closure tube 574 includes an opening 578 into which the tab 544 on the anvil 528 is inserted in order to open and close the anvil 528, as further described below. Disposed inside the closure tubes 572, 574 may be a proximate spine tube 579. Disposed inside the proximate spine tube 579 may be a main rotational (or proximate) drive shaft 580 that communicates with a secondary (or distal) drive shaft 582 via a bevel gear assembly 584. The secondary drive shaft 582 is connected to a drive gear 586 that engages a proximate drive gear 588 of the helical screw shaft 540. The vertical bevel gear 584b may sit and pivot in an opening 590 in the distal end of the proximate spine tube 579. A distal spine tube 592 may be used to enclose the secondary drive shaft 582 and the drive gears 586, 588. Collectively, the main drive shaft 580, the secondary drive shaft 582, and the articulation assembly (e.g., the bevel gear assembly 584a-c) are sometimes referred to herein as the "main drive shaft assembly."

A bearing 594 (FIG. 28) positioned at a distal end of the staple channel 526 receives the helical screw shaft 540, allowing the helical screw shaft 540 to freely rotate with respect to the channel 526. The helical screw shaft 540 may interface a threaded opening (not shown) of the cutting instrument 534 such that rotation of the helical screw shaft 540 causes the cutting instrument 534 to translate distally or proximately (depending on the direction of the rotation) through the staple channel 526. Accordingly, when the main drive shaft 580 is caused to rotate by actuation of the firing trigger 524 (as explained in further detail below), the bevel gear assembly 584*a-c* causes the secondary drive shaft 582 to rotate, which in turn, because of the engagement of the drive gears 586, 588, causes the helical screw shaft 540 to rotate, which causes the cutting instrument 534 to travel longitudinally along the channel 526 to cut any tissue clamped within the end effector 516. The sled 536 may be made of, for example, plastic, and may have a sloped distal surface. As the sled 536 traverses the channel 526, the sloped distal surface may cam the staple drivers 560 upward, which in turn push up or drive the staples 562 in the staple cartridge 538 through the clamped tissue and against the staple forming undersurface 566 of the anvil 528, thereby stapling the severed tissue. When the cutting instrument 534 is retracted, the cutting instrument 534 and the sled 536 may become disengaged, thereby leaving the sled 536 at the distal end of the channel 526.

FIGS. 29-32 illustrate an exemplary embodiment of a motor-driven endocutter, and in particular the handle 512 thereof, that provides operator-feedback regarding the deployment and loading force of the cutting instrument 534 in the end effector 516. In addition, the embodiment may use power provided by the operator in retracting the firing trigger 524 to power the device (a so-called "power assist" mode). As shown in the illustrated embodiment, the handle 512 includes exterior lower side pieces 596, 598 and exterior upper side pieces 600, 602 that fit together to form, in general, the exterior of the handle 512. A battery 604 may be provided in the pistol grip portion 530 of the handle 512. The battery 564 may be constructed according to any suitable construction or chemistry including, for example, a Li-ion chemistry such as LiCoO2 or LiNiO2, a Nickel Metal Hydride chemistry, etc. The battery 604 powers a motor 606 disposed in an upper portion of the pistol grip portion 530 of the handle 512. According to various embodiments, the motor 606 may be a DC brushed driving motor having a maximum rotation of approximately 5000 to 100,000 RPM. The motor 606 may drive a 90-degree bevel gear assembly 608 comprising a first bevel gear 610 and a second bevel gear 612. The bevel gear assembly 608 may drive a planetary gear assembly 614. The planetary gear assembly 614 may include a pinion gear 616 connected to a drive shaft 618. The pinion gear 616 may drive a mating ring gear 620 that drives a helical gear drum 622 via a drive shaft 624. A ring 626 may be threaded on the helical gear drum 622. Thus, when the motor 606 rotates, the ring 626 is caused to travel along the helical gear drum 622 by means of the interposed bevel gear assembly 608, planetary gear assembly 614 and ring gear 620.

The handle 512 may also include a run motor sensor 628 in communication with the firing trigger 524 to detect when the firing trigger 524 has been drawn in (or "closed") toward the pistol grip portion 530 of the handle 512 by the operator to thereby actuate the cutting/stapling operation by the end effector 516. The sensor 628 may be a proportional sensor such as, for example, a rheostat or variable resistor. When the firing trigger 524 is drawn in, the sensor 628 detects the movement, and sends an electrical signal indicative of the voltage (or power) to be supplied to the motor 606. When the sensor 628 is a variable resistor or the like, the rotation of the motor 606 may be generally proportional to the amount of movement of the firing trigger 524. That is, if the operator only draws or closes the firing trigger 524 in a little bit, the rotation of the motor 606 is relatively low. When the firing trigger 524 is fully drawn in (or in the fully closed position), the rotation of the motor 606 is at its maximum. In other words, the harder the operator pulls on the firing trigger 524, the more voltage is applied to the motor 606, causing a greater rate of rotation. In another embodiment, for example, a microcontroller (e.g., the microcontroller 750 of FIG. 51) may output a PWM control signal to the motor 606 based on the input from the sensor 628 in order to control the motor 606.

The handle 512 may include a middle handle piece 630 adjacent to the upper portion of the firing trigger 524. The handle 512 also may comprise a bias spring 632 connected between posts on the middle handle piece 630 and the firing trigger 524. The bias spring 632 may bias the firing trigger 524 to its fully open position. In that way, when the operator releases the firing trigger 524, the bias spring 632 will pull the firing trigger 524 to its open position, thereby removing actuation of the sensor 628, thereby stopping rotation of the motor 606. Moreover, by virtue of the bias spring 632, any time an operator closes the firing trigger 524, the operator will experience resistance to the closing operation, thereby providing the operator with feedback as to the amount of rotation exerted by the motor 606. Further, the operator could stop retracting the firing trigger 524 to thereby remove force from the sensor 628, to thereby stop the motor 606. As such, the operator may stop the deployment of the end effector 516, thereby providing a measure of control of the cutting/fastening operation to the operator.

The distal end of the helical gear drum 622 includes a distal drive shaft 634 that drives a ring gear 636, which mates with a pinion gear 638. The pinion gear 638 is connected to the main drive shaft 580 of the main drive shaft assembly. In that way, rotation of the motor 606 causes the main drive shaft assembly to rotate, which causes actuation of the end effector 516, as described above.

The ring 626 threaded on the helical gear drum 622 may include a post 640 that is disposed within a slot 642 of a slotted arm 644. The slotted arm 644 has an opening 646 its opposite end 648 that receives a pivot pin 650 that is connected between the handle exterior side pieces 596, 598. The pivot pin 650 is also disposed through an opening 652 in the firing trigger 524 and an opening 654 in the middle handle piece 630.

In addition, the handle 512 may include a reverse motor (or end-of-stroke) sensor 656 and a stop motor (or beginning-of-stroke) sensor 658. In various embodiments, the reverse motor sensor 656 may be a normally-open limit switch located at the distal end of the helical gear drum 622 such that the ring 626 threaded on the helical gear drum 622 contacts and closes the reverse motor sensor 656 when the ring 626 reaches the distal end of the helical gear drum 622. The reverse motor sensor 656, when closed, sends a signal to the motor 606 to reverse its rotation direction, thereby retracting the cutting instrument 534 of the end effector 516 following a cutting operation.

The stop motor sensor 658 may be, for example, a normally-closed limit switch. In various embodiments, it may be located at the proximate end of the helical gear drum 622 so that the ring 626 opens the switch 658 when the ring 626 reaches the proximate end of the helical gear drum 622.

In operation, when an operator of the instrument 510 pulls back the firing trigger 524, the sensor 628 detects the deployment of the firing trigger 524 and sends a signal to the motor 606 to cause forward rotation of the motor 606 at, for example, a rate proportional to how hard the operator pulls back the firing trigger 524. The forward rotation of the motor 606 in turn causes the ring gear 620 at the distal end of the planetary gear assembly 614 to rotate, thereby causing the helical gear drum 622 to rotate, causing the ring 626 threaded on the helical gear drum 622 to travel distally along the helical gear drum 622. The rotation of the helical gear drum 622 also drives the main drive shaft assembly as described above, which in turn causes deployment of the cutting instrument 534 in the end effector 516. That is, the cutting instrument 534 and sled 536 are caused to traverse the channel 526 longitudinally, thereby cutting tissue clamped in the end effector 516. Also, the stapling operation of the end effector 516 is caused to happen in embodiments where a stapling-type end effector is used.

By the time the cutting/stapling operation of the end effector 516 is complete, the ring 626 on the helical gear drum 622 will have reached the distal end of the helical gear drum 622, thereby causing the reverse motor sensor 656 to be actuated, which sends a signal to the motor 606 to cause the motor 606 to reverse its rotation. This in turn causes the cutting instrument 534 to retract, and also causes the ring 626 on the helical gear drum 622 to move back to the proximate end of the helical gear drum 622.

The middle handle piece 630 includes a backside shoulder 660 that engages the slotted arm 644 as best shown in FIGS. 30 and 31. The middle handle piece 630 also has a forward motion stop 662 that engages the firing trigger 524. The movement of the slotted arm 644 is controlled, as explained above, by rotation of the motor 606. When the slotted arm 644 rotates CCW as the ring 626 travels from the proximate end of the helical gear drum 622 to the distal end, the middle handle piece 630 will be free to rotate CCW. Thus, as the operator draws in the firing trigger 524, the firing trigger 524 will engage the forward motion stop 662 of the middle handle piece 630, causing the middle handle piece 630 to rotate CCW. Due to the backside shoulder 660 engaging the slotted arm 644, however, the middle handle piece 630 will only be able to rotate CCW as far as the slotted arm 644 permits. In that way, if the motor 606 should stop rotating for some reason, the slotted arm 644 will stop rotating, and the operator will not be able to further draw in the firing trigger 524 because the middle handle piece 630 will not be free to rotate CCW due to the slotted arm 644.

FIGS. 33 and 34 illustrate two states of a variable sensor that may be used as the run motor sensor 628 according to various embodiments of the present application. The sensor 628 may include a face portion 664, a first electrode (A) 666, a second electrode (B) 668, and a compressible dielectric material 670 (e.g., EAP) between the electrodes 666, 668. The sensor 628 may be positioned such that the face portion 664 contacts the firing trigger 524 when retracted. Accordingly, when the firing trigger 524 is retracted, the dielectric material 670 is compressed, as shown in FIG. 34, such that the electrodes 666, 668 are closer together. Since the distance "b" between the electrodes 666, 668 is directly related to the impedance between the electrodes 666, 668, the greater the distance the more impedance, and the closer the distance the less impedance. In that way, the amount that the dielectric material 670 is compressed due to retraction of the firing trigger 524 (denoted as force "F" in FIG. 34) is proportional to the impedance between the electrodes 666, 668, which can be used to proportionally control the motor 606.

Components of an exemplary closure system for closing (or clamping) the anvil 528 of the end effector 516 by retracting the closure trigger 522 are also shown in FIGS. 29-32. In the illustrated embodiment, the closure system includes a yoke 672 connected to the closure trigger 522 by a pin 674 that is inserted through aligned openings in both the closure trigger 522 and the yoke 672. A pivot pin 676, about which the closure trigger 522 pivots, is inserted through another opening in the closure trigger 522 which is offset from where the pin 674 is inserted through the closure trigger 522. Thus, retraction of the closure trigger 522 causes the upper part of the closure trigger 522, to which the yoke 672 is attached via the pin 674, to rotate CCW. The distal end of the yoke 672 is connected, via a pin 678, to a first closure bracket 680. The first closure bracket 680 connects to a second closure bracket 682. Collectively, the closure brackets 680, 682 define an opening in which the proximal end of the proximate closure tube 572 (see FIG. 25) is seated and held such that longitudinal movement of the closure brackets 680, 682 causes longitudinal motion by the proximate closure tube 572. The instrument 510 also includes a closure rod 684 disposed inside the proximate closure tube 572. The closure rod 684 may include a window 686 into which a post 688 on one of the handle exterior pieces, such as exterior lower side piece 596 in the illustrated embodiment, is disposed to fixedly connect the closure rod 684 to the handle 512. In that way, the proximate closure tube 572 is capable of moving longitudinally relative to the closure rod 684. The closure rod 684 may also include a distal collar 690 that fits into a cavity 692 in proximate spine tube 579 and is retained therein by a cap 694 (see FIG. 26).

In operation, when the yoke 672 rotates due to retraction of the closure trigger 522, the closure brackets 680, 682 cause the proximate closure tube 572 to move distally (i.e., away from the handle 512 of the instrument 510), which causes the distal closure tube 574 to move distally, which causes the anvil 528 to rotate about the pivot point 542 into the clamped or closed position. When the closure trigger 522 is unlocked from the locked position, the proximate closure tube 572 is caused to slide proximally, which causes the distal closure tube 574 to slide proximally, which, by virtue of the tab 544 being inserted in the opening 578 of the distal closure tube 574, causes the anvil 528 to pivot about the pivot point 542 into the open or unclamped position. In that way, by retracting and locking the closure trigger 522, an operator may clamp tissue between the anvil 528 and channel 526, and may unclamp the tissue following the cutting/stapling operation by unlocking the closure trigger 522 from the locked position.

According to various embodiments, the instrument 510 may include an interlock for preventing instrument 510 operation when the staple cartridge 538 is not installed in the channel 526, or when the staple cartridge 538 is installed in the channel 526 but spent. Operation of the interlock is two-fold. First, in the absence of an unspent staple cartridge 538 within the channel 526, the interlock operates to mechanically block distal advancement of the cutting instrument 534 through the channel 526 in response to actuation of the firing trigger 524. Using suitable electronics disposed within the handle 512, the interlock next detects the increase in current through the motor 606 resulting from the immobilized cutting instrument 534 and consequently interrupts current to the motor 606. Advantageously, the interlock eliminates the need for electronic sensors in the end effector 516, thus simplifying instrument design. Moreover, because the magnitude and duration of mechanical blocking force needed to produce the detected increase in motor current is significantly less than that which would be exerted if only a conventional mechanical interlock was used, physical stresses experienced by instrument components are reduced.

According to various embodiments, the interlock may include (1) a blocking mechanism to prevent actuation of the cutting instrument 534 by the motor 606 when an unspent staple cartridge 538 is not installed in the channel 526, and (2)

a lockout circuit to detect the current through the motor 606 and to interrupt the current through the motor 606 based on the sensed current.

FIG. 53 is a flow diagram of the process implemented by the interlock according to various embodiments. At step 764, the actuation of the cutting instrument 534 by the motor 606 is mechanically blocked by the blocking mechanism in the absence of an unspent staple cartridge 538 within the channel 526. As discussed below, the blocking mechanism may include components or features of conventional mechanical interlocks.

At step 766, the current through the motor 606 resulting from the blocked actuation of the cutting instrument 534 is detected by the lockout circuit. As discussed below, detection of the current may include, for example, the steps of sensing the motor current, generating a signal representative of the sensed motor current, and comparing the generated signal to a threshold signal.

At step 768, the current through the motor 606 is interrupted based on the detected current. Interrupting the current may include, for example, interrupting the current when the result of the comparison at step 766 indicates that the generated signal exceeds the threshold signal. Interrupting the current through the motor 606 may further include interrupting the current based on a position of the cutting instrument 534.

Figure 35:
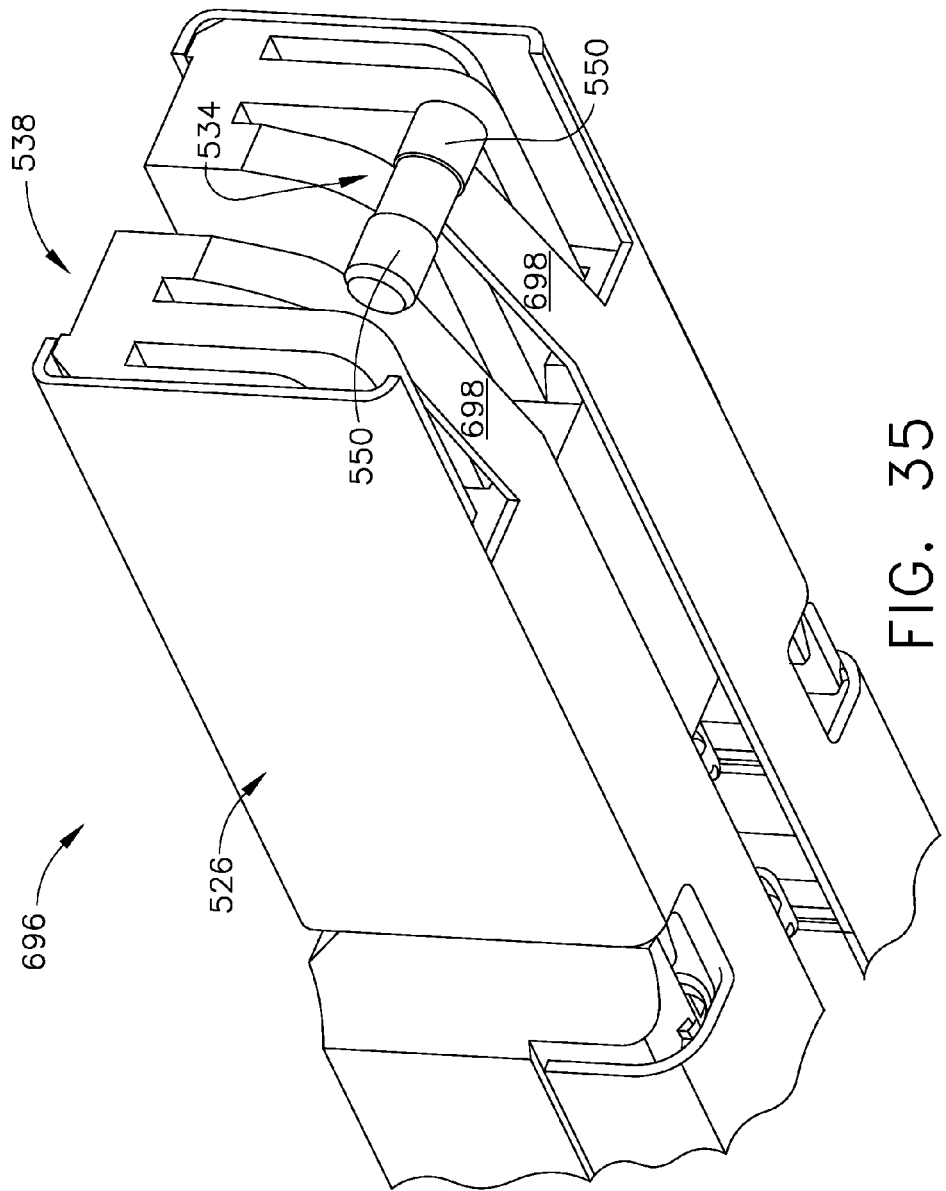

According to various embodiments, the blocking mechanism of the interlock may include features similar or identical to those of conventional mechanical interlocks for physically blocking advancement of the cutting instrument 534 in the absence of an unspent staple cartridge 538 within the channel 526. FIG. 35 illustrates a blocking mechanism 696 according to one embodiment. The blocking mechanism 696 is disclosed in U.S. Pat. No. 7,044,352 entitled "SURGICAL STAPLING INSTRUMENT HAVING A SINGLE LOCKOUT MECHANISM FOR PREVENTION OF FIRING" to Shelton, I V et al., which is incorporated herein by reference. As shown, the blocking mechanism 696 may comprise a pair of spring fingers 698 positioned in the channel 526. In particular, the spring fingers 696 may raise up to block the middle pins 550 of the cutting instrument 534 when the sled 536 (not shown in FIG. 35) is not present in an unfired position at the proximal end of the channel 526, such as when the staple cartridge 538 is not installed or when the staple cartridge 538 is installed but spent. Although two spring fingers 698 are shown, it will be appreciated that more or fewer spring fingers 698 may be used instead.

Figure 36:
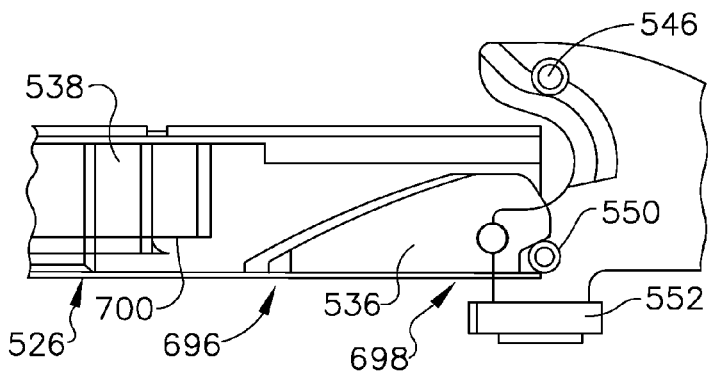

FIGS. 36-39 depict the operation of the spring fingers 698 sequentially as the instrument 510 is fired. In FIG. 36, an unspent staple cartridge 538 has been inserted into the channel 526. The presence of the sled 536 in its unfired position depresses the spring fingers 698 such that the firing drive slot 700 through which the middle pins 550 will pass is unimpeded.

Figure 37:
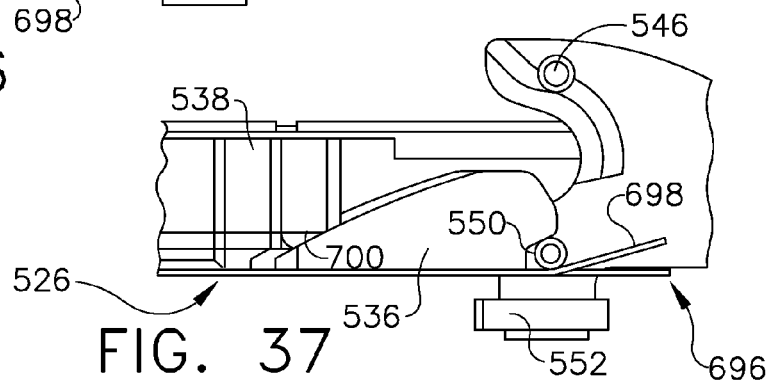

In FIG. 37, firing of the staple cartridge 538 has commenced, with the sled 536 and the middle pins 550 of the cutting instrument 534 having distally traversed off of the spring fingers 698, which then spring up into the firing drive slot 700.

Figure 38:
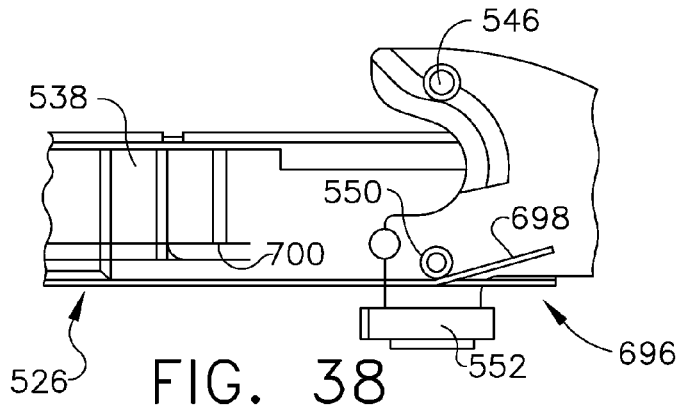

In FIG. 38, the staple cartridge 538 is now spent with the sled 536 fully driven distally and no longer depicted. The cutting instrument 534 is being retracted proximally. Since the spring fingers 698 pivot from a more distal point, the middle pins 550 of the cutting instrument 534 are able to ride up onto the spring fingers 698 during retraction, causing them to be depressed out of the firing drive slot 700.

Figure 39:
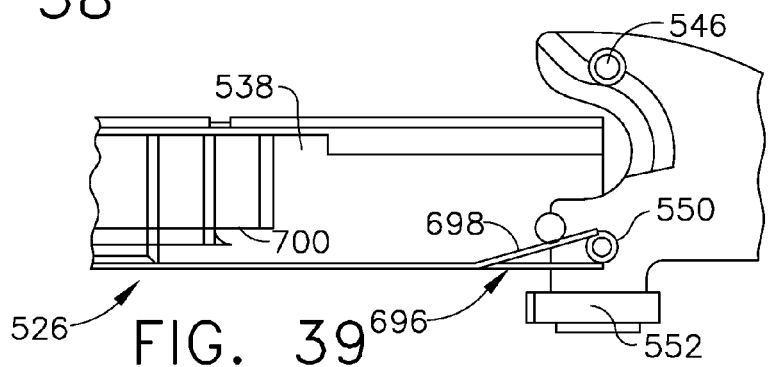

In FIG. 39, the cutting instrument 534 is fully retracted and now confronts the non-depressed pair of spring fingers 698 to prevent distal movement. The blocking mechanism 696 thereby remains activated until an unspent staple cartridge 538 is installed in the channel 526.

Figure 40:
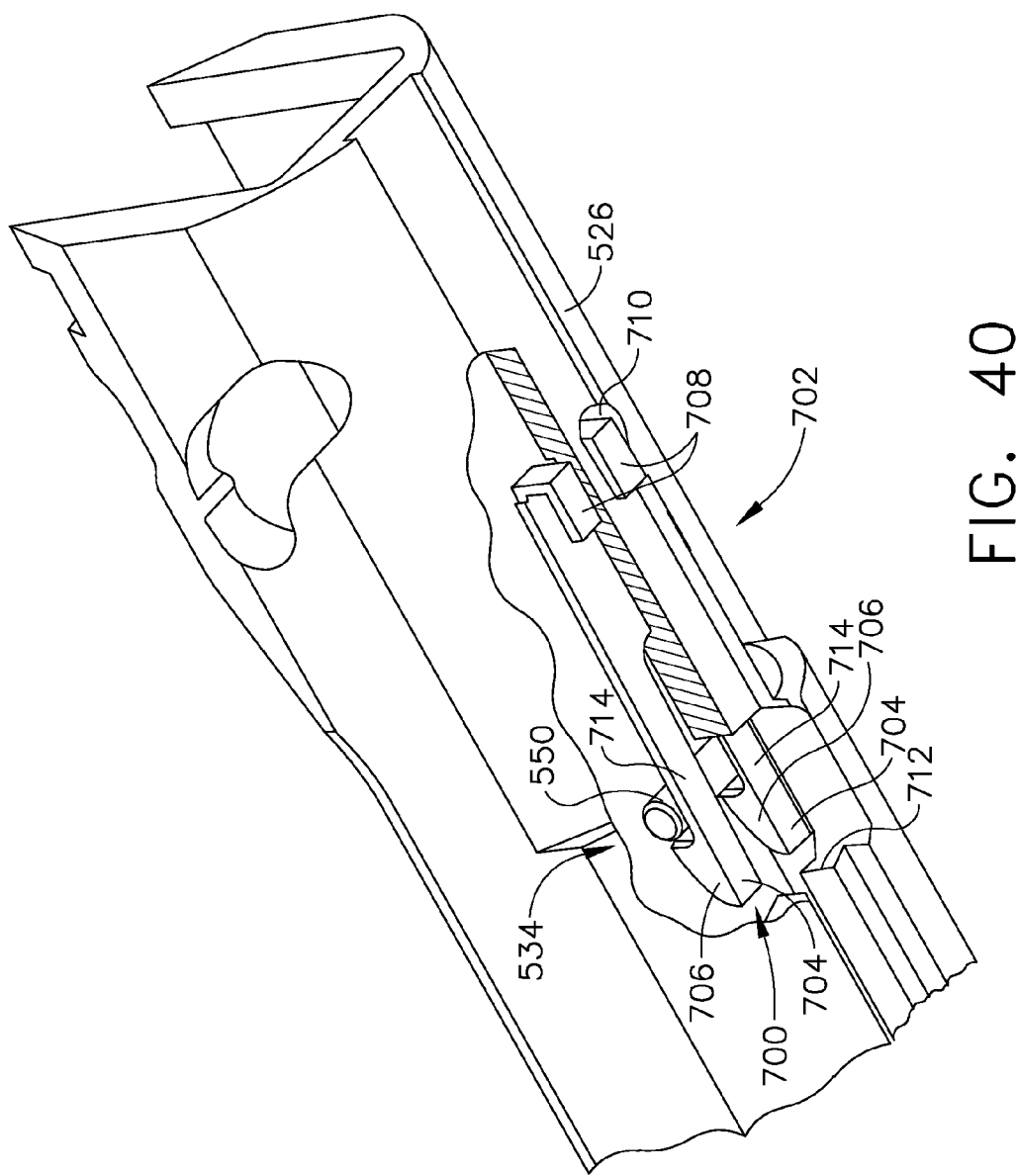

FIG. 40 depicts a blocking mechanism 702 according to another embodiment. The blocking mechanism 702, which is disclosed in U.S. Pat. No. 7,044,352 referenced above, includes a pair of hooks 704 having ramped ends 706 distally placed with regard to attachment devices 708. The attachment devices 708 are inserted through apertures 710 in the channel 526, thereby springedly attaching the hooks 704 to the channel 526. The ramped ends 706 lie above a hook recess 712 defined in the channel 526. Thus, when each ramped end 706 is contacted by the sled 536 of an unspent staple cartridge 538 (not shown in FIG. 40 the ramped ends 706 are depressed into the hook recess 712, thereby clearing the way for the middle pins 550 of the cutting instrument 534 to move distally through the firing drive slot 700 so that the staple cartridge 58 may be actuated. A thin shaft 714 coupling the attachment devices 708 respectively to the ramped end 706 of each hook 704 resiliently responds to absence of the sled 536, as depicted, wherein the ramped ends 706 return to impede the firing drive slot 700 to block the retracted middle pins 550 of the cutting instrument 534. Although two hooks 704 are shown, it will be appreciated that more or fewer hooks 704 may be used instead.

Figure 41:
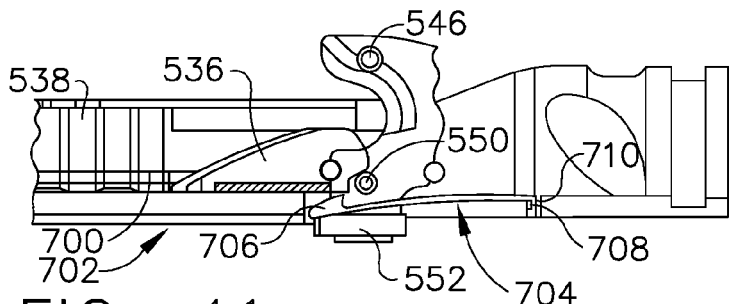
Figure 42:
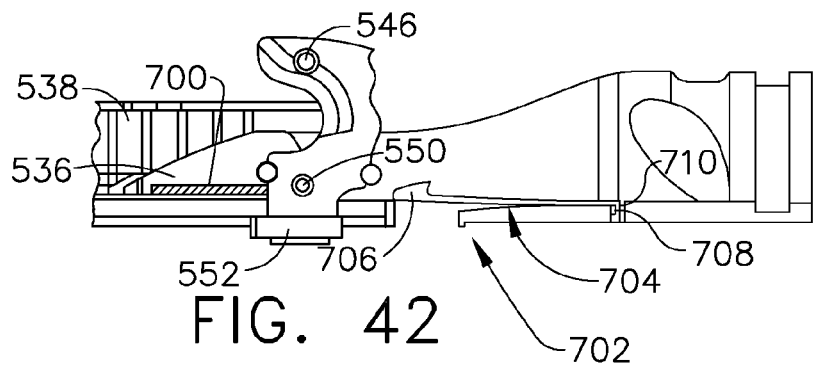

FIGS. 41-44 depict the sequence of operation of the hooks 704. In FIG. 41, the staple cartridge 538 is unspent so that the distally positioned sled 536 depresses the ramped ends 706 into the hook recess 712, allowing the middle pins 550 of the cutting instrument 534 to move distally through the firing drive slot 700 during firing, as depicted in FIG. 42. With the sled 536 and middle pins 550 distally removed with respect to the blocking mechanism 702, the ramped ends 706 resiliently raise out of the hook recess 712 to occupy the firing drive slot 700.

Figure 43:
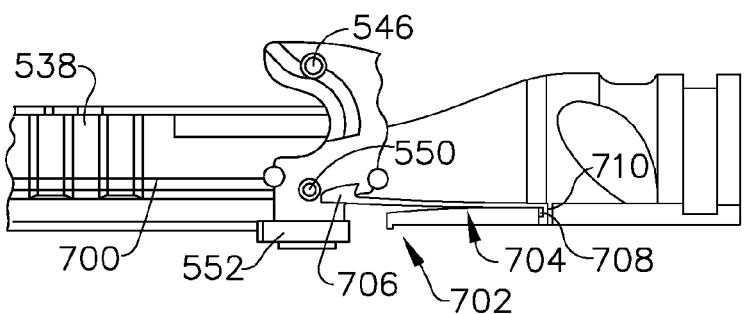
Figure 44:
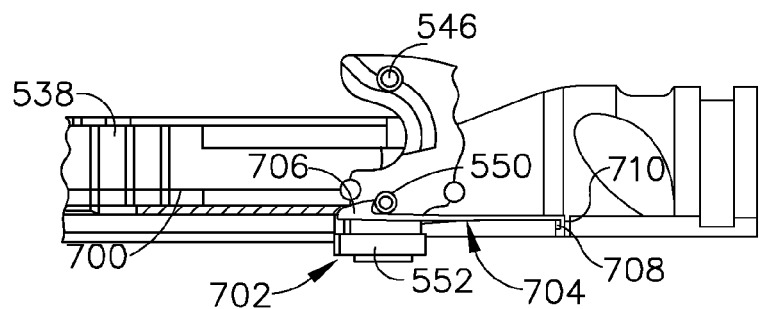

In FIG. 43, the cutting instrument 534 is being retracted to the point of contacting the ramped ends 706 of the hooks 704. Since the distal end of the ramped ends 706 is lower than the proximal part of the ramped ends 706, the middle pins 550 of the cutting instrument 534 ride over the ramped ends 706, forcing them down into the hook recess 712 until the middle pins 550 are past the ramped ends 706, as depicted in FIG. 44, wherein the ramped ends 706 resiliently spring back up to block the middle pins 550. Thus, the cutting instrument 534 is prevented from distal movement until an unspent staple cartridge 538 is installed in the channel 526.

Figure 45:
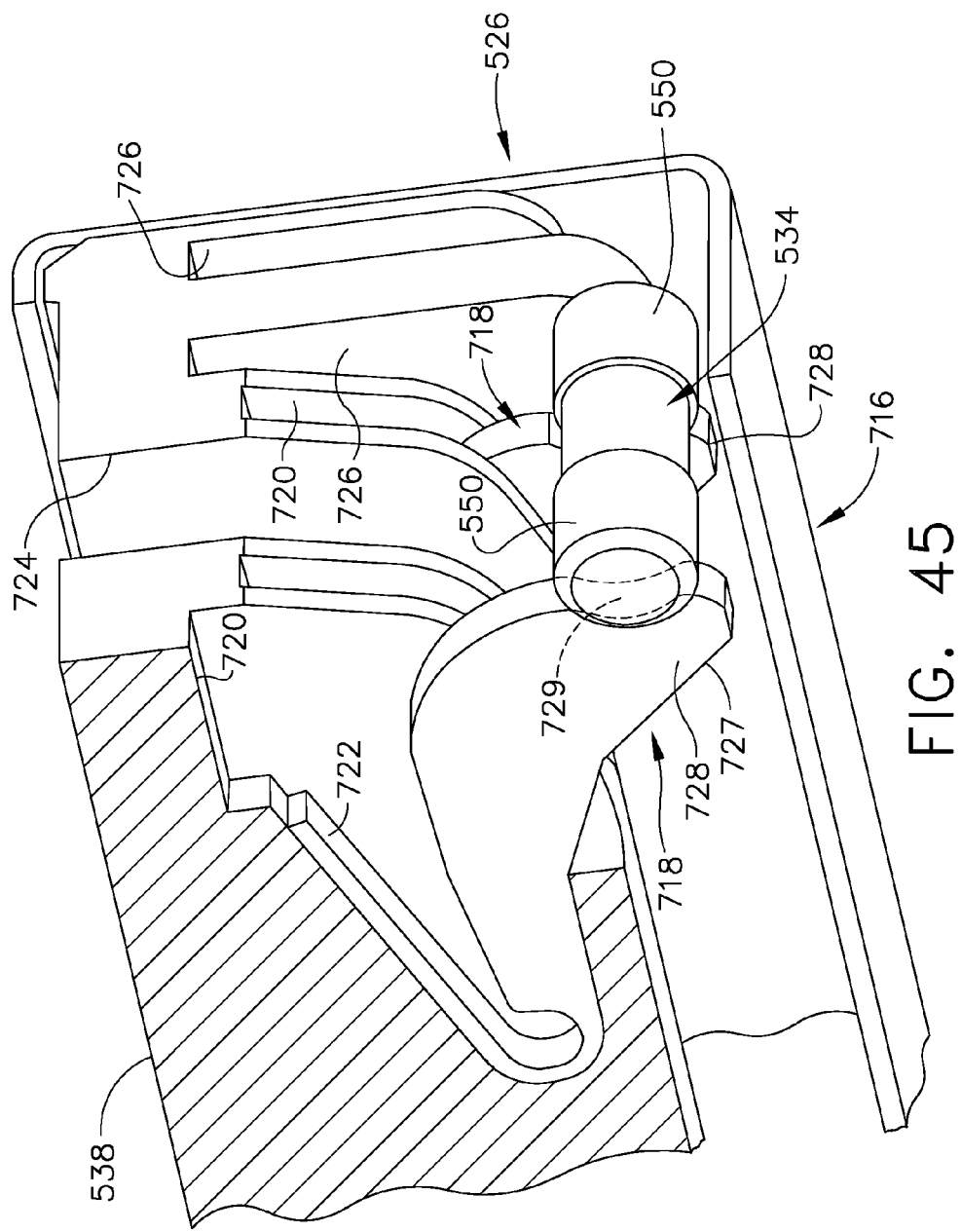

FIG. 45 depicts a blocking mechanism 716 according to yet another embodiment. The blocking mechanism 716 is disclosed in U.S. Pat. No. 6,988,649 entitled "SURGICAL STAPLING INSTRUMENT HAVING A SPENT CARTRIDGE LOCKOUT" to Shelton, I V et al., which is incorporated herein by reference. The blocking mechanism 716 is integrally formed with the staple cartridge 538 and includes proximally projecting blocking members 718 resiliently positioned above the sled 536 (not shown in FIG. 45). In particular, the blocking members 718 each reside within a downward and proximally opening cavity 720. Each blocking member 718 includes a leaf spring end 722 that is held within the cavity 720.

The cavities 720 are vertically aligned and spaced and parallel about a proximally presented vertical slot 724 in the staple cartridge 538 through which the cutting surface 556 (not shown in FIG. 45) passes. The staple cartridge 538 also includes slots 726 that longitudinally pass through the staple cartridge 538, being open from a portion of a proximal and underside of the staple cartridge 538 to receive the sled 536.

Each blocking member 718 has a deflectable end 728 having a ramped distal side 727 and blocking proximal side 729. The blocking members 718 are shaped to reside within their respective cavities 720 when depressed and to impede the distally moving middle pins 550 of the cutting instrument 734 when released.

Figure 46:
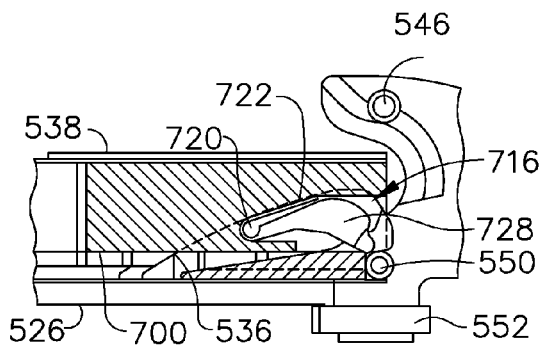

FIGS. 46-49 depict the blocking mechanism 716 sequentially as the instrument 510 is fired. In FIG. 46, an unspent staple cartridge 538 has been inserted into the channel 526 with the sled 536 depressing upward the deflectable ends 728 so that the firing drive slot 700 is unimpeded.

Figure 47:
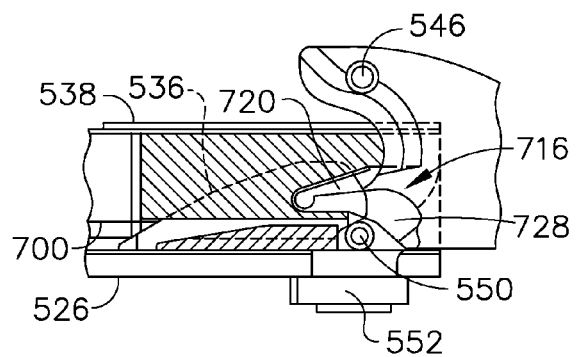

In FIG. 47, firing of the staple cartridge 538 has commenced, with the sled 536 and the middle pins 550 of the cutting instrument 534 having distally traversed past the deflectable ends 728, which then spring down into the firing drive slot 700.

Figure 48:
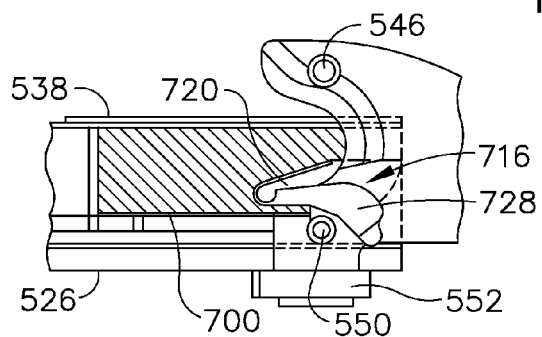

In FIG. 48, the staple cartridge 538 is now spent with the sled 536 fully driven distally and no longer depicted. The cutting instrument 534 is being retracted proximally. Since the deflectable ends 728 pivot from a more distal point, the middle pins 550 of the cutting instrument 534 are able to ride under the ramped distal sides 727 of the deflectable ends 728 during retraction, causing them to be depressed up, out of the firing drive slot 700.

Figure 49:
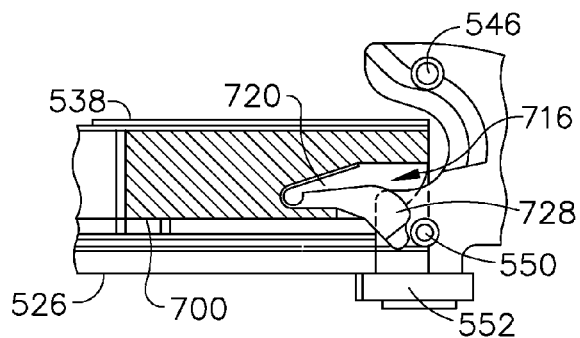

In FIG. 49, the cutting instrument 534 is fully retracted and the middle pints 550 now confront the blocking proximal sides 729 of the non-depressed (released) pair of deflectable ends 728 to prevent distal movement. The blocking mechanism 716 thereby remains activated until an unspent staple cartridge 538 is installed in the channel 526.

The blocking mechanisms 696, 702, 716 of the above-discussed embodiments are provided by way of example only. It will be appreciated that other suitable blocking mechanisms, such as blocking mechanisms disclosed in pending U.S. patent application Ser. No. 11/266,961 entitled "LOCKOUT MECHANISMS AND SURGICAL INSTRUMENTS INCLUDING SAME" to Ortiz et al., which is incorporated herein by reference, may be used instead.

FIG. 50 is a schematic diagram of an electrical circuit 731 of the instrument 510 according to various embodiments of the present application. In certain embodiments, the circuit 731 may be housed within the handle 512. In addition to the sensor 628, sensors 656, 658 (depicted as a normally-open limit switch and a normally-closed limit switch, respectively), the battery 604, and the motor 606, the circuit 731 may include a single-pole double-throw relay 730, a single-pole single-throw relay 732, a double-pole double-throw relay 734, a current sensor 736, a position sensor 738, and a current detection module 740. Relay 732, the current sensor 736, the position sensor 738, and the current detection module 740 collectively form a lockout circuit 741. As described below, the lockout circuit 741 operates to sense the current through the motor 606 and to interrupt the current based upon the sensed current, thus "locking out" the instrument 510 by disabling its operation.

As described above, sensor 628 is activated when an operator pulls in the firing trigger 524 after locking the closure trigger 522. When switch 656 is open (indicating that the cutting/stapling operation of the end effector 516 is not yet complete), coil 742 of relay 730 is de-energized, thus forming a conductive path between the battery 604 and relay 732 via a normally-closed contact of relay 730. Coil 744 of relay 732 is controlled by the current detection module 740 and the position sensor 738 as described below. When coil 744 is de-energized and coil 742 is de-energized, a conductive path between the battery 604 and a normally-closed contact of relay 734 is formed. Relay 734 controls the rotational direction of the motor 606 based on the states of switches 656, 658. When switch 656 is open and switch 658 is closed (indicating that the cutting instrument 534 has not yet fully deployed distally), coil 746 of relay 734 is de-energized. Accordingly, when coils 742, 744, 746 are collectively de-energized, current from the battery 604 flows through the motor 606 via the normally-closed contacts of relay 734 and causes the forward rotation of the motor 606, which in turn causes distal deployment of the cutting instrument 534 as described above.

When switch 656 is closed (indicating that the cutting instrument 534 has fully deployed distally), coil 742 of relay 730 is energized, and coil 746 of relay 734 is energized via a normally-open contact of relay 730. Accordingly, current now flows to the motor 606 via normally-open contacts of relays 730, 734, thus causing reverse rotation of the motor 606 which in turn causes the cutting instrument 534 to retract from its distal position and switch 656 to open. Coil 742 of relay 730 remains energized until limit switch 658 is opened, indicating the complete retraction of the cutting instrument 534.

The magnitude of current through the motor 606 during its forward rotation is indicative of forces exerted upon the cutting instrument 534 during its deployment. As described above, the absence of an unspent staple cartridge 538 in the channel 526 (e.g., the presence of a spent staple cartridge 538 or the absence of a staple cartridge 538 altogether) results in activation of the blocking mechanism 696, 702, 716 such that distal movement of the cutting instrument 534 is prevented. The resistive force exerted by the blocking mechanism 696, 702, 716 against the cutting instrument 534 causes an increase in motor torque, thus causing motor current to increase to a level that is measurably greater than that present during a cutting and stapling operation. Accordingly, by sensing the current through the motor 606, the lockout circuit 741 may differentiate between deployment of the cutting instrument 534 when an unspent cartridge 538 is installed in the channel 526 versus deployment of the cutting instrument 534 when an unspent cartridge 538 is absent from the channel 526.

The current sensor 736 may be coupled to a path of the circuit 731 that conducts current to the motor 606 during its forward rotation. The current sensor 736 may be any current sensing device (e.g., a shunt resistor, a Hall effect current transducer, etc.) suitable for generating a signal (e.g., a voltage signal) representative of sensed motor current. The generated signal may be input to the current detection module 740 for processing therein, as described below.

According to various embodiments, the current detection module 740 may be configured for comparing the signal generated by the current sensor 736 to a threshold signal (e.g., a threshold voltage signal) to determine if the blocking mechanism 696, 702, 716 has been activated. For a given instrument 510, a suitable value of the threshold signal may be empirically determined a priori by, for example, measuring the peak signal generated by the current sensor 736 when the cutting instrument 534 is initially deployed (e.g., over the first 0.06 inches of its distal movement) during a cutting and stapling operation, and when the cutting instrument 534 is deployed and encounters the activated blocking mechanism 696, 702, 716. The threshold signal value may be selected to be less than the peak signal measured when the blocking mechanism 696, 702, 716 is activated, but larger than the peak signal measured during a cutting and stapling operation.

In certain embodiments and as shown in FIG. 50, the current detection module 740 may comprise a comparator circuit 748 for receiving the threshold and current sensor 736 signals and generating a discrete output based on a comparison of the received signals. For example, the comparator circuit 748 may generate a 5 VDC output when the threshold signal is exceeded and a 0 VDC output when the threshold signal is not exceeded. The threshold signal may be generated, for example, using a suitable signal reference circuit (e.g., a voltage reference circuit) (not shown). The design and operation of the comparator circuit 748 and signal reference circuit are well known in the art and are not described further herein.

The result of the threshold and current sensor 736 signal comparison is primarily of interest during the initial deployment (e.g., during the first 0.06 inches of distal movement) of the cutting instrument 534. Accordingly, the current detection module 740 may limit the comparison based on the distal position of the cutting instrument 534 as indicated by the position sensor 738. The position sensor 738 may be any type of position sensing device suitable for generating a signal indicative of a distal position of the cutting instrument 534. In one embodiment and as shown in FIG. 50, for example, the position sensor 738 may be a normally-open Hall effect position switch 738 that is actuated based on its proximity to a magnet mounted on the ring 626. The position switch 738 may mounted within the handle 512 and operate such that when the distal position of the cutting instrument 534 (as indicated by the position of ring 626) is within a pre-determined distance (e.g., distal position <0.06 inches) of its proximal-most position, the position switch 738 is closed. Conversely, when the distal position of the cutting instrument 534 exceeds the predetermined distance (e.g., distal position >0.06 inches), the position switch 738 is opened. The position switch 738 may be connected in series with the output of the comparator circuit 748 to limit the comparison based on the position of the cutting instrument 534. In this way, if the threshold signal is exceeded when the distal position of the cutting instrument 534 is greater than pre-determined distance, the output of the position switch 738 will remain at 0 VDC (according to the example presented above), regardless of the result of the comparison. It will be appreciated that other types of position sensors 738 (e.g., mechanically-actuated limit switches, rotary potentiometers, etc.) may be used instead as an alternative to the Hall effect position switch 738 described above. Additionally, it will be appreciated that auxiliary contacts (not shown) of switch 658 may be used as an alternative to a separate position sensor 738. In embodiments in which the position sensor 738 does not include a switched output (e.g., when the position sensor 738 is a potentiometer or other analog-based position sensor), additional processing of the position sensor 736 output using, for example, a second comparator circuit, may be necessary.

As shown in FIG. 50, the output of the position switch 738 may be connected to coil 744 of relay 732. Driver circuitry (not shown) between the position switch 738 and the coil 744 may be provided if necessary. Accordingly, if the signal generated by the current sensor 736 exceeds the threshold signal (indicating activation of the blocking mechanism 696, 702, 716 due to the absence of an unspent staple cartridge 538), and the cutting instrument 534 is within the predetermined distance of its proximal-most position, coil 744 will be energized. This causes normally-closed switch of relay 732 to open, thereby interrupting current flow to the motor 606 and removing the resistive force exerted by the blocking mechanism 696, 702, 716 upon the cutting instrument 534. Importantly, because the blocking mechanism 696, 702, 716 need only apply a mechanical blocking force sufficient to cause the threshold signal to be exceeded, the physical stresses exerted by the blocking mechanism 696, 702, 716 are reduced in magnitude and duration compared to those that would be exerted if only conventional mechanical interlocks were used. Furthermore, because the interlock does not require electronic sensors in the end effector 516, instrument design is simplified.

FIG. 51 is a schematic diagram of an electrical circuit 749 of the instrument 510 according to another other embodiment of the present application in which a processor-based microcontroller 750 is used to implement functionality of the lockout circuit 741 described above. Although not shown for purposes of clarity, the microcontroller 750 may include components well known in the microcontroller art such as, for example, a processor, a random access memory (RAM) unit, an erasable programmable read-only memory (EPROM) unit, an interrupt controller unit, timer units, analog-to-digital conversion (ADC) and digital-to-analog conversion (DAC) units, and a number of general input/output (I/O) ports for receiving and transmitting digital and analog signals. The current sensor 736 and the position sensor 738 may be connected to analog and digital inputs, respectively, of the microcontroller 750, and the coil 744 of relay 732 may be connected to a digital output of the microcontroller 750. It will be appreciated that in embodiments in which the output of the position sensor 738 is an analog signal, the position sensor 738 may be connected to an analog input instead. Additionally, although the circuit 749 of FIG. 51 includes relays 730, 732, 734, it will be appreciated that in other embodiments the relay switching functionality may be replicated using solid state switching devices, software, and combinations thereof. In certain embodiments, for example, instructions stored and executed in the microcontroller 750 may be used to control solid state switched outputs of the microcontroller 750. In such embodiments, switches 656, 658 may be connected to digital inputs of the microcontroller 750.

FIG. 52 is a flow diagram of a process implemented by the microcontroller 750 according to various embodiments. At step 752, the microcontroller 750 receives the signal generated by the current sensor 736 via an analog input and converts the received signal into a corresponding digital current sensor signal.

At step 754, values of the digital current sensor signal are compared to a digital threshold value stored within the microcontroller 750. The digital threshold value may be, for example, a digitized representation of the threshold signal discussed above in connection with FIG. 50. If all values of the digital current sensor signal are less than the digital threshold value, the process terminates at step 756. If a value of the digital current sensor signal exceeds the digital threshold value, the process proceeds to step 758.

At step 758, the position sensor 738 input is processed to determine if the cutting instrument 534 is within the predetermined distance of its proximal-most position. If the cutting instrument 534 is not within the predetermined distance, the process is terminates at step 760. If the cutting instrument 534 is within the predetermined distance, the process proceeds to step 762.

At step 762, the digital output to corresponding to coil 744 is energized, thus causing the normally closed contacts of relay 732 to open, which in turn interrupts the current flow to the motor 606.

Although embodiments described above compare the magnitude of the current sensor signal (or a digitized version thereof) to a threshold signal or value, it will be appreciated that other metrics for analyzing the current sensor signal may additionally or alternatively be used to differentiate between deployment of the cutting instrument 534 when an unspent cartridge 538 is installed in the channel 526 versus deployment of the cutting instrument 534 when an unspent cartridge 538 is absent from the channel 526. For example, the current detection module 740 or the microcontroller 750 may be configured to determine derivative and/or integral characteristics of the current sensor signal for comparison to corresponding thresholds signals or values. Additionally, in certain embodiments the current sensor signal may be processed prior to its analysis using, for example, signal conditioners and/or filters implementing one or more filter response functions (e.g., infinite impulse response functions).

The various embodiments of embodiments of the present application have been described above in connection with cutting-type surgical instruments. It should be noted, however, that in other embodiments, the inventive surgical instrument disclosed herein need not be a cutting-type surgical instrument, but rather could be used in any type of surgical instrument including remote sensor transponders. For example, it could be a non-cutting endoscopic instrument, a grasper, a stapler, a clip applier, an access device, a drug/gene therapy delivery device, an energy device using ultrasound, RF, laser, etc. In addition, embodiments of the present application may be in laparoscopic instruments, for example. Embodiments of the present application also have application in conventional endoscopic and open surgical instrumentation as well as robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although embodiments of the present application have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method for preventing operation of a surgical instrument, the surgical instrument configured for removably receiving an expendable staple cartridge and comprising a moveable cutting instrument and a motor to actuate the cutting instrument in response to a current therethrough, the method comprising:
    mechanically blocking actuation of the cutting instrument by the motor in the absence of an unexpended staple cartridge in the instrument;
    detecting the current through the motor resulting from the blocked actuation of the cutting instrument; and
    interrupting the current through the motor based on the detected current.

2. The method of claim 1, comprising:
    sensing the motor current;
    generating a signal representative of the sensed motor current; and
    comparing the generated signal to a threshold signal.

3. The method of claim 2, comprising interrupting the current when the generated signal exceeds the threshold signal.

4. The method of claim 3, comprising interrupting the current based on a position of the cutting instrument.

5. The method of claim 4, wherein:
    the cutting instrument is located in an end effector of the surgical instrument, and wherein upon actuation the cutting instrument is for traversing the end effector from a proximal position to a distal position;
    mechanically blocking actuation of the cutting instrument comprises mechanically blocking actuation of the cutting instrument with a blocking mechanism in the end effector of the surgical instrument;
    detecting the current through the motor comprises detecting the current through the motor with a current sensor that is in a current path of the motor; and
    interrupting the current through the motor comprises opening a switch that is connected to the motor.

6. The method of claim 5, further comprising detecting a position of the cutting instrument in the end effector, and wherein interrupting the current through the motor comprises interrupting the current through the motor when generated signal exceeds the threshold signal and the cutting instrument is within a threshold distance from its proximal-most position.

* * * * *